(12) United States Patent
Smethurst et al.

(10) Patent No.: US 8,853,368 B2
(45) Date of Patent: Oct. 7, 2014

(54) HUMAN ANTIBODIES AGAINST HUMAN GLYCOPROTEIN VI AND THEIR USE

(75) Inventors: Peter Alexander Smethurst, Cambridge (GB); Willem Hendrik Ouwehand, Cambridge (GB); Richard William Farndale, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 2589 days.

(21) Appl. No.: 10/499,266

(22) PCT Filed: Dec. 18, 2002

(86) PCT No.: PCT/GB02/05755
§ 371 (c)(1),
(2), (4) Date: Jun. 23, 2005

(87) PCT Pub. No.: WO03/054020
PCT Pub. Date: Jul. 3, 2003

(65) Prior Publication Data
US 2006/0088531 A1 Apr. 27, 2006

(30) Foreign Application Priority Data
Dec. 20, 2001 (GB) .................... 0130543.2

(51) Int. Cl.
*C07K 16/28* (2006.01)
*A61K 39/00* (2006.01)

(52) U.S. Cl.
CPC ............ *C07K 16/28* (2013.01); *C07K 2317/565* (2013.01); *C07K 2317/56* (2013.01); *A61K 2039/505* (2013.01); *C07K 2317/622* (2013.01); *C07K 2317/34* (2013.01); *C07K 2317/21* (2013.01)
USPC ................................... 530/388.22

(58) Field of Classification Search
None
See application file for complete search history.

(56) References Cited

U.S. PATENT DOCUMENTS

| | | | | |
|---|---|---|---|---|
| 5,859,205 | A * | 1/1999 | Adair et al. ................. | 530/387.3 |
| 6,245,527 | B1 * | 6/2001 | Busfield et al. .............. | 435/69.1 |
| 6,989,144 | B1 * | 1/2006 | Busfield et al. .............. | 424/130.1 |
| 7,183,076 | B2 * | 2/2007 | Arathoon et al. ............ | 435/69.1 |

FOREIGN PATENT DOCUMENTS

| | | | |
|---|---|---|---|
| EP | 0 120 694 | A2 | 10/1984 |
| EP | 0 125 023 | A1 | 11/1984 |
| EP | 0 184 187 | A2 | 6/1986 |
| EP | 0 239 400 | A2 | 9/1987 |
| GB | 2 188 638 | A | 10/1987 |
| WO | 92/01047 | A1 | 1/1992 |
| WO | 93/11161 | A1 | 6/1993 |
| WO | 94/13804 | A1 | 6/1994 |
| WO | WO 9720932 | A1 * | 6/1997 |
| WO | 99/58572 | A1 | 11/1999 |
| WO | WO0100810 | | 1/2001 |
| WO | WO02080968 | | 10/2002 |

OTHER PUBLICATIONS

Vaughan et al., Nat Biotechnol. Mar. 1996;14(3):309-14.*
Janeway et al., Immunobiology, 5th Ed., Garland Science, pp. 94-105 (2001).*
Vajdos et al., J Mol Biol. Jul. 5, 2002;320(2):415-28.*
Modrau et al., Thromb Res. Dec. 1, 2001;104(5):309-15.*
Heldin et al., Physiol Rev. Oct. 1999;79(4):1283-316.*
Rodger Bick, N Engl J Med. Jul. 10, 2003;349(2):109-11.*
Eduardo Padlan, Mol Immunol. Feb. 1994;31(3):169-217.*
Portolano et al., J Immunol. Feb. 1, 1993;150(3):880-7.*
Nieswandt et al., J Exp Med. Feb. 19, 2001;193(4):459-69.*
Dorffler-Melly et al., Basic Res Cardiol. Dec. 2000;95(6):503-9.*
Ulrich et al., Circ Res. Apr. 13, 2007;100(7):979-91.*
Segel et al., Blood Cells Mol Dis. Oct. 2000;26(5):540-60.*
Gregory Lip, Cochrane Database of Systematic Reviews 2000, Issue 2.*
David Dawson, Am J Cardiol. Jun. 28, 2001;87(12A):19D-27D.*
The Merck Manual of Diagnosis and Therapy, Mark Beers and Robert Berkow, eds., Published by Merck Research Laboratories, 17th ed., 1999, pp. 923-924.*
'T Hart et al., Br J Rheumatol. Mar. 1998;37(3):314-23.*
Brown et al. (J Immunol. May 1, 1996;156(9):3285-91).*
Muller et al. 1998, Structure, 5, 1325-1338.*
Rudikoff et al., Proc. Natl. Acad. Sci. USA, 79: 1979-1983, Mar. 1982.*
Colman P. M. (Research in Immunology, 145:33-36, 1994).*
Nieswandt, Bernhard et al., "Expression and Function of the Mouse Collagen Receptor Glycoprotein VI is Strictly Dependent on Its Association with the FcRγ Chain," *J. Biol. Chem.* 275 (31):23998-24002, Aug. 4, 2000.
Qian, Ming et al., "Anti GPVI human antibodies neutralizing collagen-induced platelet aggregation isolated from a combinatorial phage display library," *Human Antibodies*, 11(3):97-105, 2002.

(Continued)

*Primary Examiner* — Zachary Skelding
(74) *Attorney, Agent, or Firm* — Seed IP Law Group PLLC

(57) ABSTRACT

Specific binding members directed to human glycoprotein VI (GPVI), in particular human antibodies, may employ the antibody VH and/or VL domain of the scFv fragment herein termed 10B12 or one or more complementarity determining regions (CDRs) of the 10B12 heavy chain variable (VH) and/or light chain variable (VL) domains, especially VH CDR3 in other antibody framework regions. Antibody molecules are provided with advantageous and unexpected properties, especially ability to inhibit collagen-induced platelet aggregation and the adhesion of platelets to Collagen-Related Peptide (CRP). Domain 1 of human GPVI is a primary target for the 10B12 antibody with these properties, and the epitope includes lysine 59.

13 Claims, 30 Drawing Sheets

(56) References Cited

OTHER PUBLICATIONS

Smethurst, Peter A., et al., "Identification of the collagen binding surface of human glycoprotein VI and functional blockade by a novel human recombinant antibody." *Blood*, 100(11):474, Nov. 16, 2002.
"A Guide to Polyacrylamide Gel Electrophoresis and Detection," Bulletin 6040 Rev A US/EG, 10-1558, 0512 Sig 1211, BioRad Laboratories, Inc., Hercules, CA (2011), 47 pages.
Bagshawe et al., "Antibody-Enzyme Conjugates Can Generate Cytoxic Drugs from Inactive Precursors at Tumor Sites," *Antibody, Immunoconjugates, and Radiopharmaceuticals* 4(4):915-922, 1991.
Barbas III, et al., "In vitro evolution of a neutralizing human antibody to human immunodeficiency virus type 1 to enhance affinity and broaden strain cross-reactivity," *Proc. Natl. Acad. Sci. USA* 91:3809-3813, Apr. 1994.
Bellavite et al., "A Colorimetric Method for the Measurement of Platelet Adhesion in Microtiter Plates," *Analytical Biochemistry* 216:444-450, 1994.
Bernatowicz et al., "Preparation of Peptide-Protein Immunogens Using N-Succinimidyl Bromoacetate as a Heterobifunctional Crosslinking Reagent," *Analytical Biochemistry* 155:95-102, 1986.
Bird et al., "Single-Chain Antigen-Binding Proteins," *Science* 242:423-426, Oct. 21, 1988.
Bonnerot et al., "syk protein tyrosine kinase regulates Fc receptor γ-chain-mediated transport to lysosomes," *The EMBO Journal* 17(16):4606-4616, 1998.
Chothia et al., "Structural Repertoire of the Human $V_H$ Segments," *J. Mol. Biol.* 227:799-817, 1992.
Clemetson, "Platelet Activation: Signal Transduction Via Membrane Receptors," *Thromb Haemost* 74(1):111-116, 1995.
Coller, "Anti-GPIIb/IIIa Drugs: Current Strategies and Future Directions," *Thromb Haemost* 86:427-443, 2001.
Cook et al., "The human immunoglobulin $V_H$ repertoire," *Immunology Today* 16(5):237-242, 1995.
de Bruin et al., "Selection of high-affinity phage antibodies from phage display libraries," *Nature Biotechnology* 17:397-399, Apr. 1999.
Furihata et al., "Variation in Human Platelet Glycoprotein VI Content Modulates Glycoprotein VI-Specific Prothrombinase Activity," *Arterioscler Thromb Vasc Biol* 21:1857-1863, 2001.
Gram et al., "In vitro selection and affinity maturation of antibodies from a naïve combinatorial immunoglobulin library," *Proc. Natl. Acad. Sci.* 89:3576-3580, Apr. 1992.
Griffiths et al., "Isolation of high affinity human antibodies directly from large synthetic repertoires," *The EMBO Journal* 13(14):3245-3260, 1994.
Hames, B. D. and Rickwood, D. (eds.), *Gel Electrophoresis of Proteins: A Practical Approach*, Second Edition, Oxford University Press, Walton Street, Oxford, 1990, 77 pages.
Harrison, "Review," *British Journal of Haematology* 111:733-744, 2000.
Hawkins et al., "Selection of Phage Antibodies by Binding Affinity: Mimicking Affinity Maturation," *J. Mol. Biol.* 226:889-896, 1992.
Heemskerk et al., "Collagen But Not Fibrinogen Surfaces Induce Bleb Formation, Exposure of Phosphatidylserine, and Procoagulant Activity of Adherent Platelets: Evidence for Regulation by Protein Tyrosine Kinase-Dependent $Ca^{2+}$ Responses," *Blood* 90(7):2615-2625, Oct. 1, 1997.
Holliger et al., ""Diabodies": Small bivalent and bispecific antibody fragments," *Proc. Natl. Acad. Sci. USA* 90:6444-6448, Jul. 1993.
Holliger et al., "Engineering bispecific antibodies," *Current Opinion in Biotechnology* 4:446-449, 1993.
Hu et al., "Minibody: A Novel Engineered Anti-Carcinoembryonic Antigen Antibody Fragment (Single-Chain FV-$C_H$3) Which Exhibits Rapid, High-Level Targeting of Xenografts," *Cancer Research* 56:3055-3061, Jul. 1, 1996.
Hughes-Jones et al., "Characterization of human blood group scFv antibodies derived from V gene phage-display library," *British Journal of Haematology* 88:180-186, 1994.

Huston et al., "Protein engineering of antibody binding sites: Recovery of specific activity in an anti-digoxin single-chain Fv analogue produced in *Escherichia coli*," *Proc. Natl. Acad. Sci. USA* 85:5879-5883, Aug. 1988.
Jandrot-Perrus et al., "Cloning, characterization, and functional studies of human and mouse glycoprotein VI: a platelet-specific collagen receptor from the immunoglobulin superfamily," *Blood* 96(5):1798-1807, Sep. 1, 2000.
Jennings et al., "Production of calmodulin-tagged proteins in Drosophila Schneider S2 cells: A novel system for antigen production and phage antibody isolation," *Journal of Immunological Methods* 316:75-83, 2006.
Jones et al., "Improved Methods for Building Protein Models in Electron Density Maps and the Location of Errors in these Models," *Acta Cryst* A47:110-119, 1991.
Kehrel et al., "Glycoprotein VI is a Major Collagen Receptor for Platelet Activation: It Recognizes the Platelet-Activating Quaternary Structure of Collagen, Whereas CD36, Glycoprotein IIb/IIIa, and von Willebrand Factor Do Not," *Blood* 91(2):491-499, Jan. 15, 1998.
Knight et al., "Collagen-platelet interaction: Gly-Pro-Hyp is uniquely specific for platelet Gp VI and mediates platelet activation by collagen," *Cardiovascular Research* 41:450-457, 1999.
Knight et al., "Identification in Collagen Type I of an Integrin $\alpha_2\beta_1$-binding Site Containing an Essential GER Sequence," *The Journal of Biological Chemistry* 273(50):33287-33294, Dec. 11, 1998.
Kunicki et al., "Hereditary Variation in Platelet Integrin $\alpha_2\beta_1$ Density is Associated With Two Silent Polymorphisms in the $\alpha_2$ Gene Coding Sequence," *Blood* 89(6):1939-1943, Mar. 15, 1997.
Kunicki et al., "Variability of Integrin $\alpha_2\beta_1$ Activity on Human Platelets," *Blood* 82(9):2693-2703, Nov. 1, 1993.
Lapierre et al., "The gel test: a new way to detect red cell antigen-antibody reactions," *Transfusion* 30:109-113, 1990.
Ledermann et al., "A Phase-I Study of Repeated Therapy with Radiolabelled Antibody to Carcinoembryonic Antigen Using Intermittent or Continuous Administration of Cyclosporin A to Suppress the Immune Response," *Int. J. Cancer* 47:659-664, 1991.
Marks et al., "By-passing Immunization: Building High Affinity Human Antibodies by Chain Shuffling," *Bio/Technology* 10:779-783, Jul. 1992.
Marks et al., "By-passing Immunization: Human Antibodies from V-gene Libraries Displayed on Phage," *J. Mol. Biol.* 222:581-597, 1991.
Montigiani et al., "Alanine Substitutions in Calmodulin-binding Peptides Result in Unexpected Affinity Enhancement," *J. Mol. Biol.* 258:6-13, 1996.
Moroi et al., "A Patient with Platelets Deficient in Glycoprotein VI That Lack Both Collagen-induced Aggregation and Adhesion," *J. Clin. Invest.* 84:1440-1445, Nov. 1989.
Neri et al., "Calmodulin as a Versatile Tag for Antibody Fragments," *Bio/Technology* 13:373-377, Apr. 1995.
Nicholls et al., "Protein Folding and Association: Insights From the Interfacial and Thermodynamic Properties of Hydrocarbons," *Proteins: Structure, Function, and Genetics* 11:281-296, 1991.
Nieswandt et al., "Expression and function of the mouse collagen receptor GPVI is strictly dependent on its association with the FcRγ-chain," JBC Papers in Press, Published on May 23, 2000 as Manuscript M003803200, Department of Molecular Oncology, General Surgery, University of Witten-Herdecke, Wuppertal, Germany, 21 pages.
Nieswandt et al., "Glycoprotein VI but not α2β1 integrin is essential for platelet interaction with collagen," *The EMBO Journal* 20(9):2120-2130, 2001.
Nieswandt et al., "Long-term Antithrombotic Protection by In Vivo Depletion of Platelet Glycoprotein VI in Mice," *J. Exp. Med.* 193(4):459-469, Feb. 19, 2001.
Onley et al., "Micromolar $Ca^{2+}$ Concentrations Are Essential for $Mg^{2+}$-dependent Binding of Collagen by the Integrin $\alpha_2\beta_1$ in Human Platelets," *The Journal of Biological Chemistry* 275(32):24560-24564, Aug. 11, 2000.
Plückthun, "Antibody Engineering: Advances from the Use of *Escherichia coli* Expression Systems," *Bio/Technology* 9:545-551, Jun. 1991.

(56) References Cited

OTHER PUBLICATIONS

Polgár et al., "Platelet Activation and Signal Transduction by Convulxin, a C-type Lectin from *Crotalus durissus* terrificus (Tropical Rattlesnake) Venom via the p62/GPVI Collagen Receptor," *The Journal of Biological Chemistry* 272(21):13576-13583, May 23, 1997.

Ponder et al., "Tertiary Templates for Proteins: Use of Packing Criteria in the Enumeration of Allowed Sequences for Different Structural Classes," *J. Mol. Biol.* 193:775-791, 1987.

Reff, "High-level production of recombinant immunoglobulins in mammalian cells," *Current Opinion in Biotechnology* 4:573-576, 1993.

Reiter et al., "Engineering antibody Fv fragments for cancer detection and therapy: Disulfide-stabilized Fv fragments," *Nature Biotechnology* 14:1239-1245, Oct. 1996.

Ridgway et al., "'Knobs-into-holes' engineering of antibody $C_H 3$ domains for heavy chain heterodimerization,"*Protein Engineering* 9(7):617-621, 1996.

Saelman et al., "Platelet Adhesion to Collagen Types I Through VIII Under Conditions of Stasis and Flow is Mediated by GPIa/IIa ($\alpha_2\beta_1$-Integrin)," *Blood* 83(5):1244-1250, Mar. 1, 1994.

Šali et al., "Evaluation of Comparative Protein Modeling by Modeller," *Proteins: Structure, Function, and Genetics* 23:318-326, 1995.

Santoso et al., "Association of the Platelet Glycoprotein Ia $C_{807}T$ Gene Polymorphism With Nonfatal Myocardial Infarction in Younger Patients," *Blood* 93(8):2449-2453, Apr. 15, 1999.

Schier et al., "Isolation of Picomolar Affinity Anti-c-erbB-2 Single-chain Fv by Molecular Evolution of the Complementarity Determining Regions in the Center of the Antibody Binding Site," *J. Mol. Biol.* 263:551-567, 1996.

Siljander et al., "Platelet Adhesion Enhances the Glycoprotein VI-Dependent Procoagulant Response: Involvement of p38 MAP Kinase and Calpain,"*Arterioscler Thromb Vasc Biol* 21:618-627, 2001.

Sixma et al., "A New Perfusion Chamber to Detect Platelet Adhesion using a Small Volume of Blood," *Thrombosis Research* 92:S43-S46, 1998.

Smethurst et al., "Identification of the primary collagen-binding surface on human glycoprotein VI by site-directed mutagenesis and by a blocking phage antibody," *Blood* 103(3):903-911, Feb. 1, 2004.

Stemmer, "Rapid evolution of a protein in vitro by DNA shuffling," *Nature* 370:389-391, Aug. 4, 1994.

Trill et al., "Production of monoclonal antibodies in COS and CHO cells," *Current Opinion in Biotechnology* 6:553-560, 1995.

van der Merwe et al., "Affinity and kinetic analysis of the interaction of the cell adhesion molecules rat CD2 and CD48," *The EMBO Journal* 12(13):4945-4954, 1993.

Vaughan et al., "Human Antibodies with Sub-nanomolar Affinities Isolated from a Large Non-immunized Phage Display Library," *Nature Biotechnology* 14:309-314, Mar. 1996.

Verkleij et al., "Simple Collagen-Like Peptides Support Platelet Adhesion Under Static But Not Under Flow Conditions: Interaction Via $\alpha 2\beta 1$ and von Willebrand Factor With Specific Sequences in Native Collagen is a Requirement to Resist Shear Forces," *Blood* 91(10):3808-3816, May 15, 1998.

Watson et al., "The Role of ITAM- and ITIM-coupled Receptors in Platelet Activation by Collagen," *Thromb Haemost* 86:276-288, 2001.

Ward et al., "Binding activities of a repertoire of single immunoglobulin variable domains secreted from *Escherichia coli*," *Nature* 341:544-546, Oct. 12, 1989.

\* cited by examiner

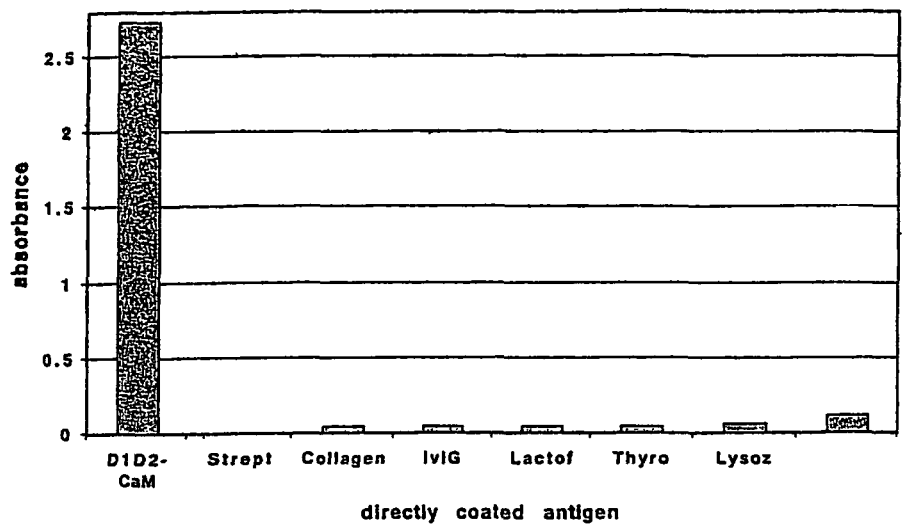
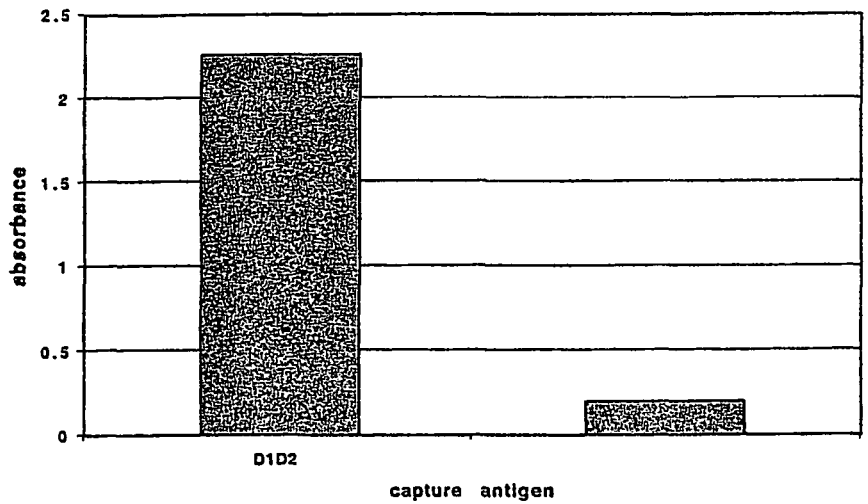
Figure 3

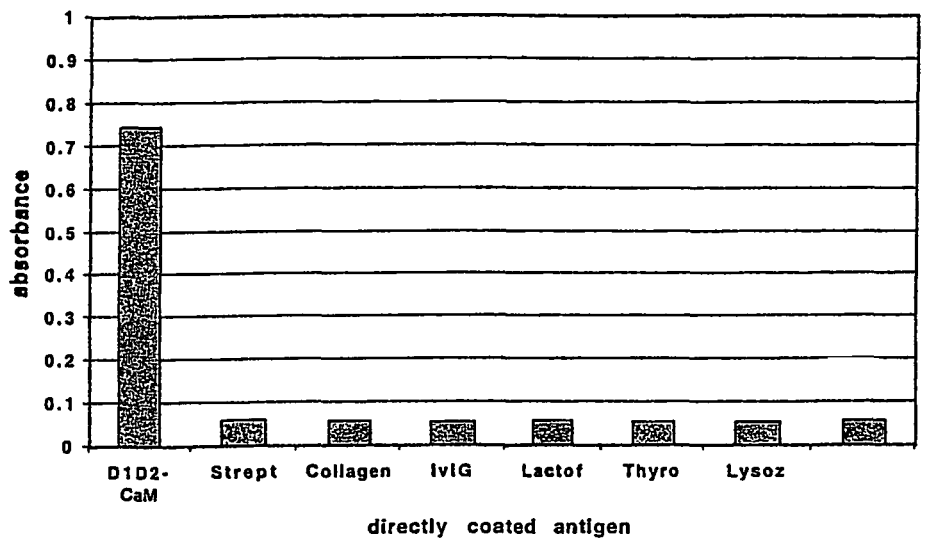
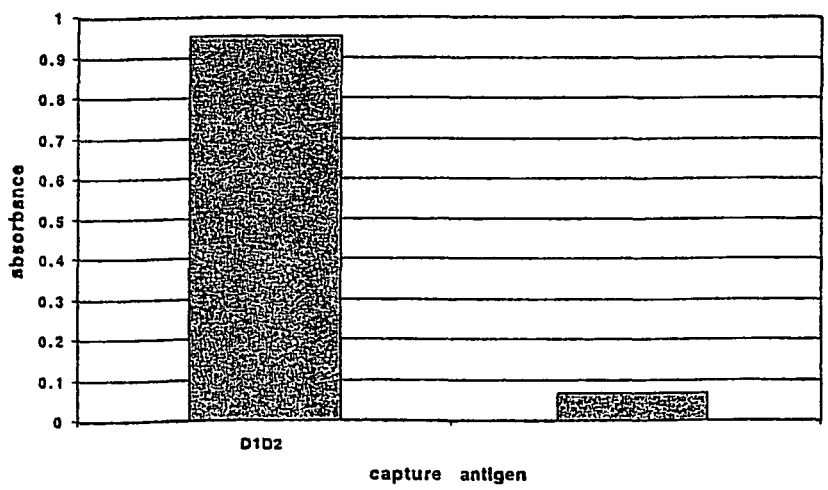
Figure 4

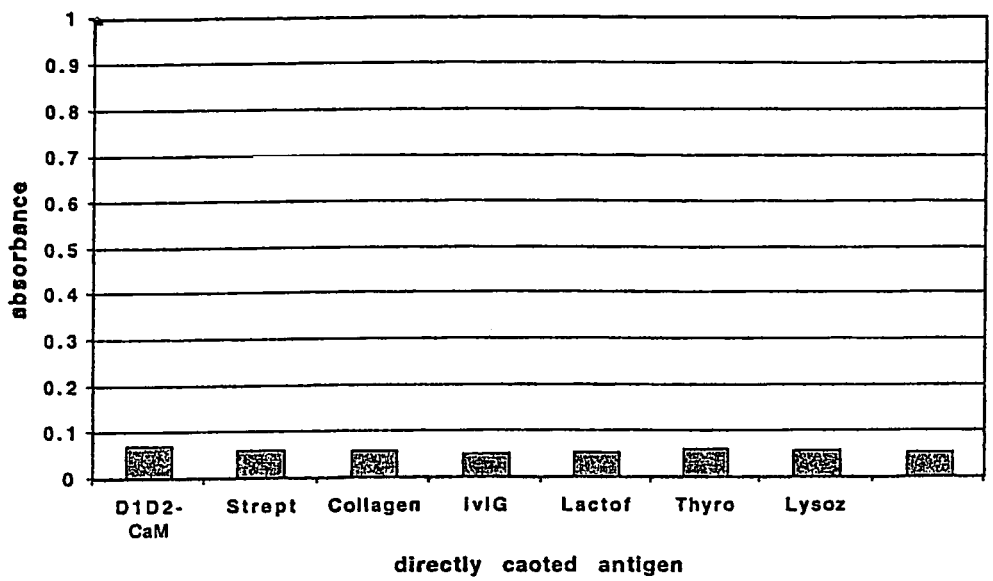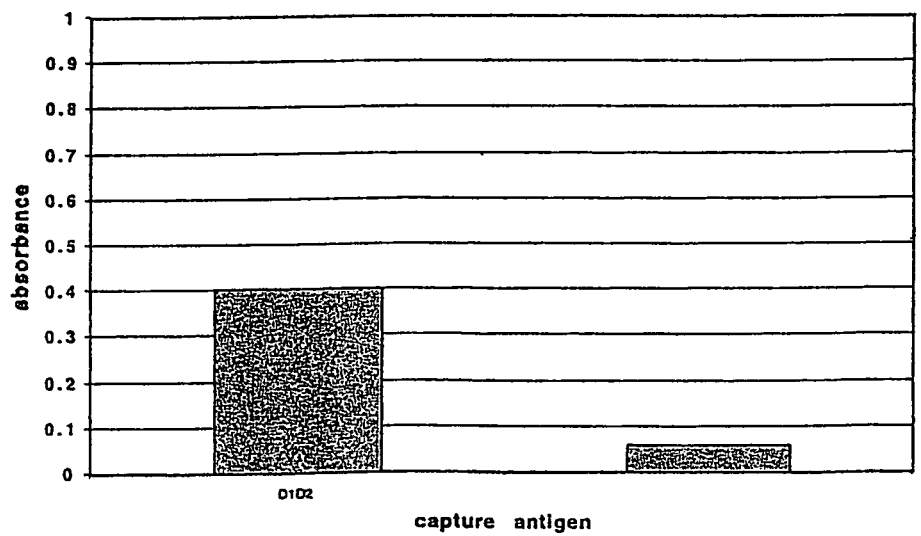
Figure 5

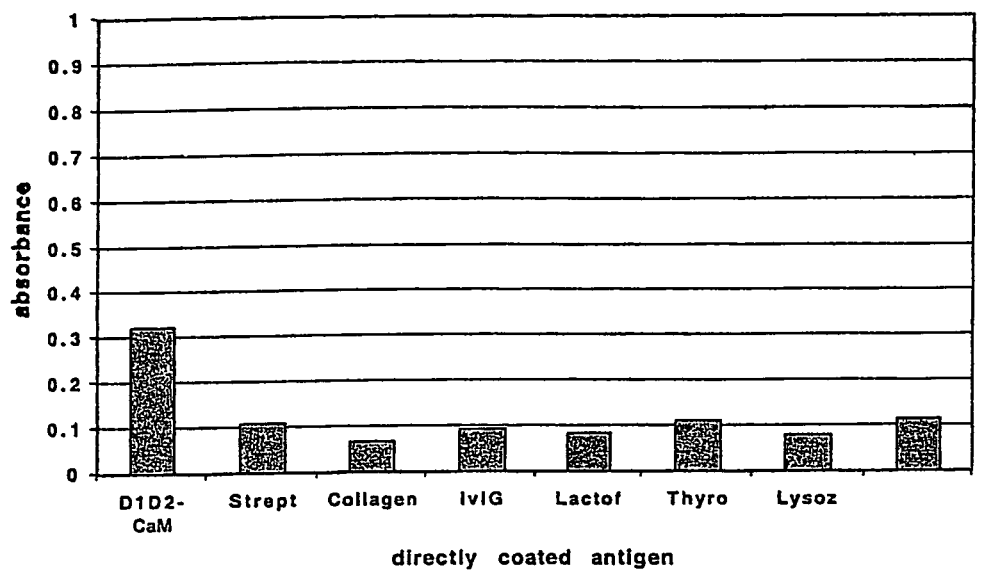
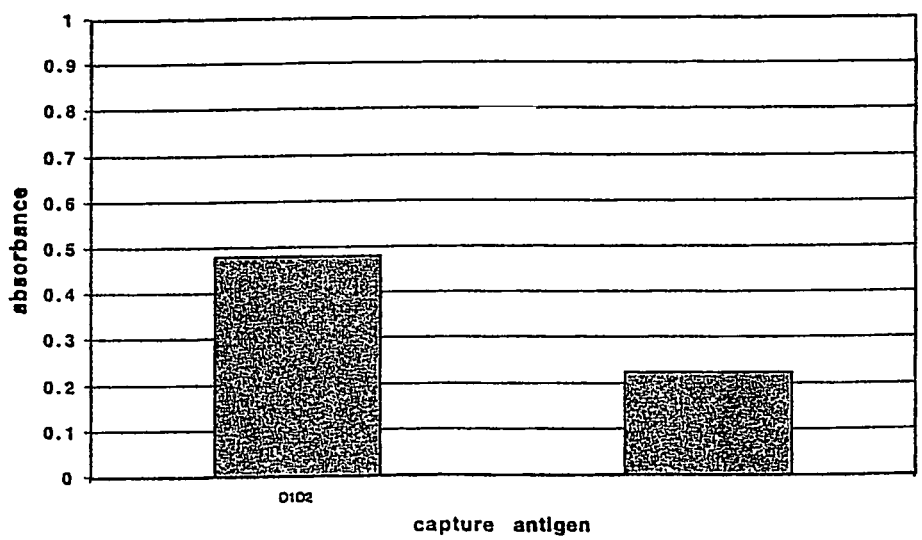
Figure 6

A.
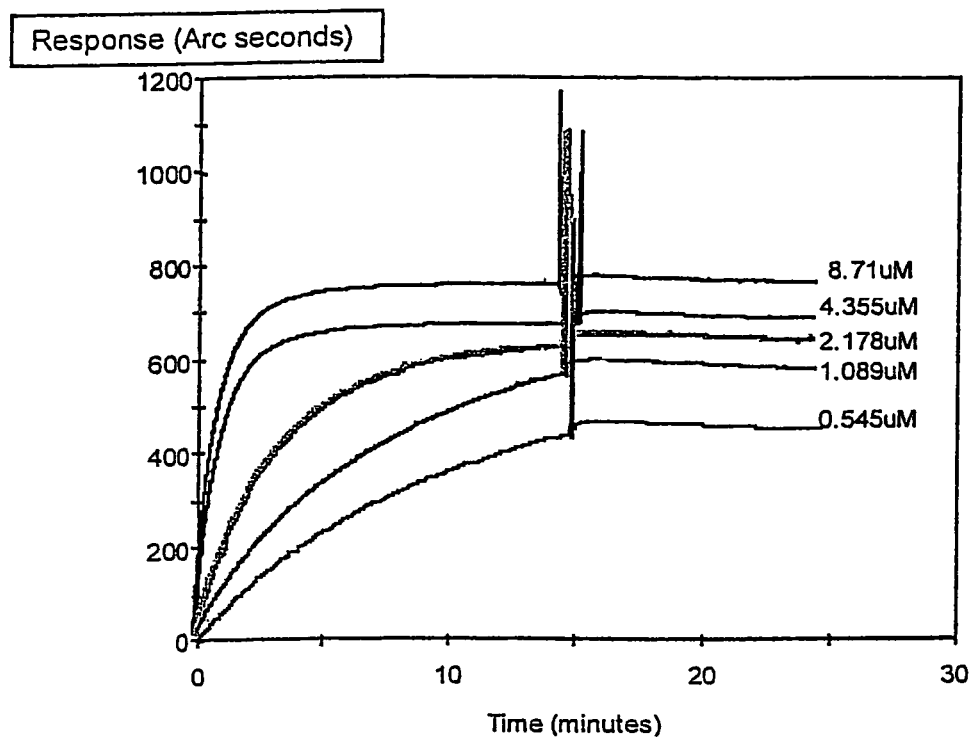
B.
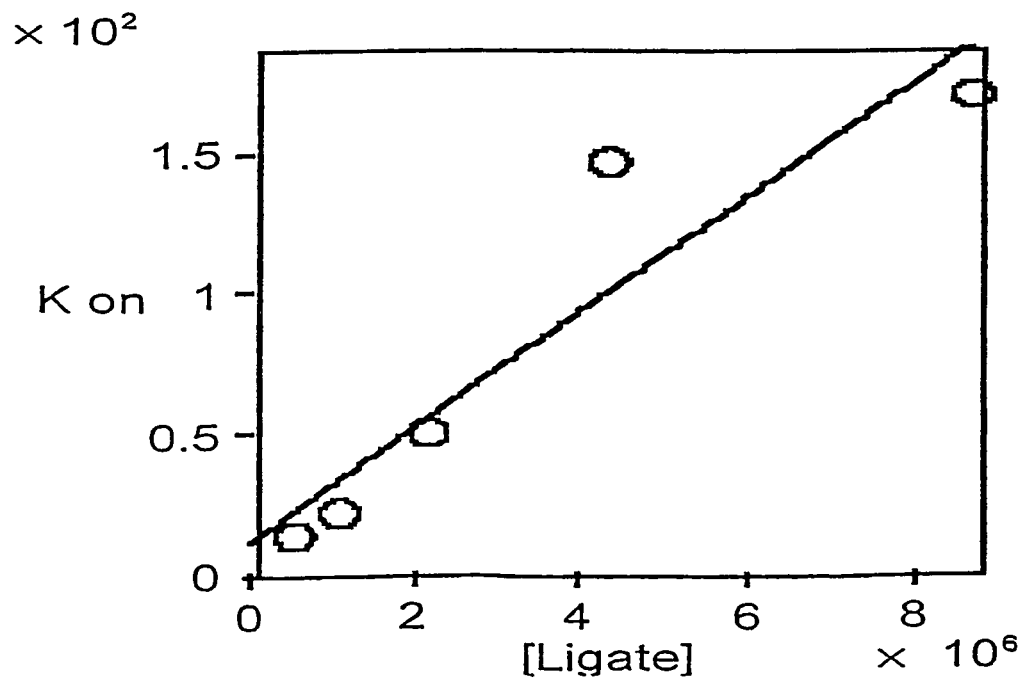
Figure 19 - A and B

C.
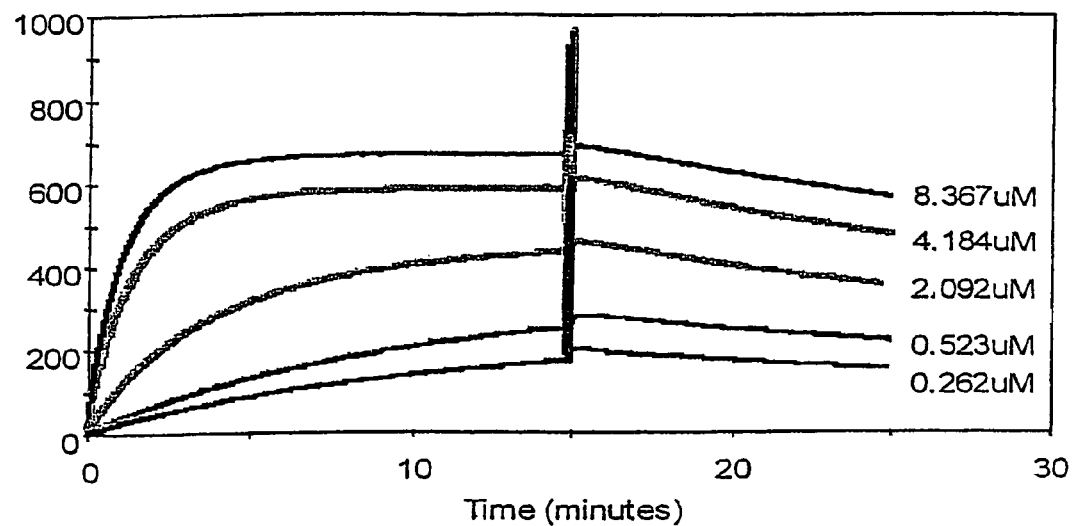
D.
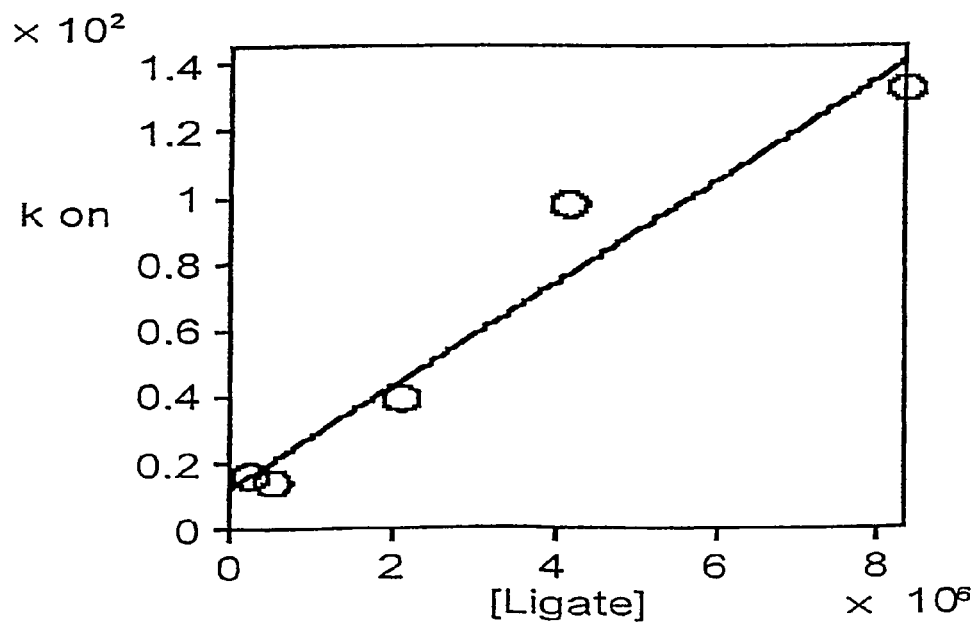
Figure 19 - C and D

```
                          SEQUENCE LISTING

<160> NUMBER OF SEQ IDS: 25

<210> SEQ ID NO 1
<211> LENGTH: 363
<212> TYPE: DNA
<213> ORGANISM: Homo sapiens

<400> SEQUENCE: 1
gaggtccagc tggtacagtc tgggggaggc gtggtccagc ctgggggtc cctgagactc      60 tcctgtgcag cgtctggatt caccttcagt agctatggca tgcactgggt ccgccaggct    120
ccaggcaagg gctggagtg gtggcattt atacggtatg atggaagtaa taaatactat     180
gcagactccg tgaagggccg attcaccatc tccagagaca attccaagaa cacgctgtat   240
ctgcaaatga acagcctgag agctgaggac acggctgtgt attactgtac ggacggatgg   300
gcagagatgg ctacaactga tgatgctttt gatatttggg gcagagggac aatggtcacc   360
gtc                                                                 363

<210> SEQ ID NO 2
<211> LENGTH: 121
<212> TYPE: PRT
<213> ORGANISM: Homo sapiens

<400> SEQUENCE: 2

Glu Val Gln Leu Val Gln Ser Gly Gly Gly Val Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Asp Gly Trp Ala Glu Met Ala Thr Thr Asp Ala Phe Asp Ile
        100                 105                 110

Trp Gly Arg Gly Thr Met Val Thr Val
        115                 120

<210> SEQ ID NO 3
<211> LENGTH: 321
<212> TYPE: DNA
<213> ORGANISM: Homo sapiens

<400> SEQUENCE: 3
gacatccaga tgacccagtc tccttccacc ctgtctgcat ctattggaga cagagtcacc     60
atcacctgcc gggccagtga gggtatttat cactggttgg cctggtatca gcagaagcca    120
gggaaagccc ctaaactcct gatctataag gcctctagtt tagccagtgg ggccccatca    180
aggttcagcg gcagtggatc tgggacagat ttcactctca ccatcagcag cctgcagcct    240
gatgattttg caacttatta ctgccaacaa tatagtaatt atccgctcac tttcggcgga    300
gggaccaagc tggagatcaa a                                              321

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Leu Glu Ile Lys
            100                 105

<210> SEQ ID NO 5
<211> LENGTH: 5
<212> TYPE: PRT
<213> ORGANISM: Homo sapiens

<400> SEQUENCE: 5

Ser Tyr Gly Met His
1               5

<210> SEQ ID NO 6
<211> LENGTH: 17
<212> TYPE: PRT
<213> ORGANISM: Homo sapiens

<400> SEQUENCE: 6

Phe Ile Arg Tyr Asp Gly Ser Asn Lys Tyr Tyr Ala Asp Ser Val Lys
1               5                   10                  15
Gly

<210> SEQ ID NO 7
<211> LENGTH: 14
<212> TYPE: PRT
<213> ORGANISM: Homo sapiens

<400> SEQUENCE: 7

Gly Trp Ala Glu Met Ala Thr Thr Asp Ala Phe Asp Ile
1               5                   10

<210> SEQ ID NO 8
<211> LENGTH: 11
<212> TYPE: PRT
<213> ORGANISM: Homo sapiens

<400> SEQUENCE: 8

Arg Ala Ser Glu Gly Ile Tyr His Trp Leu Ala
1               5                   10

<210> SEQ ID NO 9
<211> LENGTH: 7
<212> TYPE: PRT
<213> ORGANISM: Homo sapiens

<400> SEQUENCE: 9

Lys Ala Ser Ser Leu Ala Ser
1               5

<210> SEQ ID NO 10
<211> LENGTH: 7
<212> TYPE: PRT
<213> ORGANISM: Homo sapiens

<400> SEQUENCE: 10

Gln Gln Tyr Ser Asn Tyr Pro
1               5

<210> SEQ ID NO 11
<211> LENGTH: 369
<212> TYPE: DNA
<213> ORGANISM: Homo sapiens

<400> SEQUENCE: 11
caggtacagc tgcagcagtc aggggcagag gtgaaaaagc ccggggagtc tctgaagatc      60
tcctgtcagg cttctggata cagcttttcc agttactgga tcgcctgggt gcgccagatg     120
cccgggaaag cctggagtt gatggggatc atctatcctg gtgactctga tgccagatac     180
agcccgtcct tccaaggcca ggtcaccttc tcagccgaca gtccataaa caccgcctat     240
ttgcagtgga gcagcctgaa ggcctcggac accgccatgt attattgtgc gagacaaggg    300
aaaactggga gctactattt tggtgctttt gatgtctggg gccaagggac aatggtcacc     360
gtctcttca                                                             369

<210> SEQ ID NO 12
<211> LENGTH: 123
<212> TYPE: PRT
<213> ORGANISM: Homo sapiens

<400> SEQUENCE: 12

Gln Val Gln Leu Gln Gln Ser Gly Ala Glu Val Lys Lys Pro Gly Glu
1               5                   10                  15

Ser Leu Lys Ile Ser Cys Gln Ala Ser Gly Tyr Ser Phe Ser Ser Tyr
            20                  25                  30

Trp Ile Ala Trp Val Arg Gln Met Pro Gly Lys Gly Leu Glu Leu Met
        35                  40                  45

Gly Ile Ile Tyr Pro Gly Asp Ser Asp Ala Arg Tyr Ser Pro Ser Phe
    50                  55                  60

Gln Gly Gln Val Thr Phe Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Lys Thr Gly Ser Tyr Tyr Phe Gly Ala Phe Asp Val
            100                 105                 110

Trp Gly Gln Gly Thr Met Val Thr Val Ser Ser
        115                 120

<210> SEQ ID NO 13
<211> LENGTH: 330
<212> TYPE: DNA
<213> ORGANISM: Homo sapiens

<400> SEQUENCE: 13
cagtctgtgt tgacgcagcc gccctcaatg tctgcggccc caggacagaa ggtcaccatc      60
tcctgcactg gaaccagcag tgacgttggt ggttataact atgtctcctg gtaccaacag     120
cacccaggca aagcccccaa actcatgctt tttgaggtca gtcatcggcc ctcaggggtt     180
tctaatcgct tctctggctc caagtctgac aacacggcct ccctgaccat ctctgggctc     240
caggctgagg acgaggctga ttattactgc agttcatata caggcagcag cacttgggtg     300
ttcggcggag ggaccaaggt caccgtccta                                     330

<210> SEQ ID NO 14
<211> LENGTH: 110
<212> TYPE: PRT
<213> ORGANISM: Homo sapiens

<400> SEQUENCE: 14

Gln Ser Val Leu Thr Gln Pro Pro Ser Met Ser Ala Ala Pro Gly Gln
1               5                   10                  15

Lys Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Leu Phe Glu Val Ser His Arg Pro Ser Gly Val Ser Asn Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Asp Tyr Tyr Cys Ser Ser Tyr Thr Gly Ser
                85                  90                  95

Ser Thr Trp Val Phe Gly Gly Gly Thr Lys Val Thr Val Leu
            100                 105                 110

<210> SEQ ID NO 15
<211> LENGTH: 5
<212> TYPE: PRT

```
<213> ORGANISM: Homo sapiens

<400> SEQUENCE: 15

Ser Tyr Trp Ile Ala
1               5

<210> SEQ ID NO 16
<211> LENGTH: 17
<212> TYPE: PRT
<213> ORGANISM: Homo sapiens

<400> SEQUENCE: 16

Ile Ile Tyr Pro Gly Asp Ser Asp Ala Arg Tyr Ser Pro Ser Phe Gln
1               5                   10                  15

Gly

<210> SEQ ID NO 17
<211> LENGTH: 14
<212> TYPE: PRT
<213> ORGANISM: Homo sapiens

<400> SEQUENCE: 17

Gln Gly Lys Thr Gly Ser Tyr Tyr Phe Gly Ala Phe Asp Val
1               5                   10

<210> SEQ ID NO 18
<211> LENGTH: 14
<212> TYPE: PRT
<213> ORGANISM: Homo sapiens

<400> SEQUENCE: 18

Thr Gly Thr Ser Ser Asp Val Gly Gly Tyr Asn Tyr Val Ser
1               5                   10

<210> SEQ ID NO 19
<211> LENGTH: 7
<212> TYPE: PRT
<213> ORGANISM: Homo sapiens

<400> SEQUENCE: 19

Glu Val Ser His Arg Pro Ser
1               5

<210> SEQ ID NO 20
<211> LENGTH: 10
<212> TYPE: PRT
<213> ORGANISM: Homo sapiens

<400> SEQUENCE: 20

Ser Ser Tyr Thr Gly Ser Ser Thr Trp Val
1               5                   10

<210> SEQ ID NO 21
<211> LENGTH: 37
<212> TYPE: PRT
<213> ORGANISM: Artificial Sequence
<220> FEATURE:
<223> OTHER INFORMATION: Collagen-Related Peptide
<220> FEATURE:
<221> NAME/KEY: VARIANT
<222> LOCATION: 3, 6, 9, 12, 15, 18, 21, 24, 27, 30, 33, 36
<223> OTHER INFORMATION: Xaa = hydroxyproline

<400> SEQUENCE: 21

Gly Cys Xaa Gly Pro Xaa Gly Pro Xaa Gly Pro Xaa Gly Pro Xaa Gly
```

```
                1               5              10              15
Pro Xaa Gly Pro Xaa Gly Pro Xaa Gly Pro Xaa Gly Pro Xaa Gly Pro
                        20              25              30

Xaa Gly Cys Xaa Gly
        35

<210> SEQ ID NO 22
<211> LENGTH: 37
<212> TYPE: PRT
<213> ORGANISM: Artificial Sequence
<220> FEATURE:
<223> OTHER INFORMATION: GPP10

<400> SEQUENCE: 22

Gly Cys Pro Gly Pro Pro Gly Pro Pro Gly Pro Pro Gly Pro Pro Gly
 1               5              10              15

Pro Pro Gly Pro Pro Gly Pro Pro Gly Pro Pro Gly Pro Pro Gly Pro
                20              25              30

Pro Gly Cys Pro Gly
        35

<210> SEQ ID NO 23
<211> LENGTH: 17
<212> TYPE: DNA
<213> ORGANISM: Artificial Sequence
<220> FEATURE:
<223> OTHER INFORMATION: Primer LMB3

<400> SEQUENCE: 23
caggaaacag ctatgac                                              17

<210> SEQ ID NO 24
<211> LENGTH: 17
<212> TYPE: DNA
<213> ORGANISM: Artificial Sequence
<220> FEATURE:
<223> OTHER INFORMATION: Primer fd-seq1

<400> SEQUENCE: 24
gaattttctg tatgagg                                              17

<210> SEQ ID NO 25
<211> LENGTH: 17
<212> TYPE: DNA
<213> ORGANISM: Artificial Sequence
<220> FEATURE:
<223> OTHER INFORMATION: Primer pHEN-SEQ

<400> SEQUENCE: 25
ctatgcggcc ccattca                                              17
```

HUMAN ANTIBODIES AGAINST HUMAN GLYCOPROTEIN VI AND THEIR USE

The present invention relates to specific binding members directed to human glycoprotein VI (GPVI), in particular human antibodies against human GPVI. Preferred embodiments of the present invention employ the antibody VH and/or VL domain of the scFv fragment herein termed 10B12. Further preferred embodiments employ one or more complementarity determining regions (CDRs) of the 10B12 heavy chain variable (VH) and/or light chain variable (VL) domains, especially VH CDR3 in other antibody framework regions. The inventors have identified a number of antibody molecules with advantageous and unexpected properties, especially ability to inhibit collagen-induced platelet aggregation and the adhesion of platelets to Collagen-Related Peptide (CRP). The inventors have also found, contrary to expectations, that domain 1 of human GPVI is a primary target for the 10B12 antibody with these properties.

Collagen is the most potent of the constituents of the vascular subendothelial matrix which cause platelet activation at sites of injury. The proper platelet response to collagen involves the concerted action of several cell surface receptors. Glycoprotein (GP) Ib/IX/V binds von Willebrand Factor, a protein abundantly present in plasma which can also attach to collagen, to tether platelets at high shear. GPIaIIa ($\alpha 2 \beta 1$ integrin) is involved principally in firm adhesion of the platelets to collagen. There is increasing evidence that QPVI is the major receptor responsible for activation of platelets by collagen. The use of such GPVI-specific ligands as the triple-helical synthetic Collagen-Related Peptide (CRP) (Knight et al 1999) and the snake venom protein, convulxin (Polgar et al 1997), has enabled those aspects of the platelet response to collagen which are mediated by GPVI to be identified. These involve phosphorylation of the Fc receptor $\gamma$-chain, with which GPVI associates, leading to phosphorylation and activation of the haematopoietic cell tyrosine kinase, p72Syk, and phospholipase C (PLC) $\gamma 2$, to a rise in intracellular $Ca^{2+}$ and to exposure of a procoagulant cellular surface and microvesiculation (Watson et al 2001, Siljander et al 2001). These events stimulated by GPVI converge with signals caused by other ligands such as ADP or thrombin at the level of $Ca^{2+}$ signalling, culminating in the increased expression of the fibrinogen receptor GPIIbIIIa (integrin $\alpha IIb\beta 3$) and its affinity for its ligands.

CRP (GCO(GPO)$_{10}$GCOG (single letter amino acid code where O is hydroxyproline—SEQ ID NO. 21)) activates platelets via GPVI (Kehrel et al 1998) and supports GPVI-dependent platelet adhesion, whereas a closely-related compound GPP10. (GCP(GPP)$_{10}$GCPG—SEQ ID NO. 22), does not (Knight et al 1999). The ability of recombinant fragments of GPVI to selectively bind CRP instead of GPP10 is thus a good measure of functional integrity.

An important means of inhibiting platelet activation, to prevent formation of platelet-rich clots and to reduce the incidence of vessel re-occlusion, is to antagonise GPIIbIIIa function. This receptor undergoes a shape change that allows its ligand, plasma fibrinogen, to bind and platelets to aggregate. Abciximab (ReoPro™), the Fab fragment of a mouse/human chimeric antibody 7E3, inhibits the binding of fibrinogen to GPIIbIIIa and is clinically used to reduce reocclusion in patients undergoing percutaneous coronary intervention (including stent insertion and balloon angioplasty (Coller 2001) and in patients with unstable angina. The activation of GPIIbIIIa lies downstream of GPVI or other receptors for non-collagenous ligands such as adenosine diphosphate (ADP) or thrombin, so antagonists of GPIIbIIIa effectively block the final, common response of the platelet to numerous stimuli. However, there is potentially a role for earlier, more selective and specific inhibition of platelet responses. For instance, the response of platelets to exposure of the subendothelium may be dampened after vessel surgery, while maintaining the functional capacity of other pathways which may be necessary for normal haemostasis at sites distal from that of surgical intervention.

It has been shown recently by Nieswandt and colleagues that a rat monoclonal antibody JAQ1 against mouse GPVI prevents collagen-induced platelet aggregation in vitro (Nieswandt 2001a). A F(ab) fragment of the same antibody, when delivered as a single intra-peritoneal dose in vivo, also produces a long-term reduction in the sensitivity of platelets to collagen (Nieswandt 2001b). This effect of the antibody is distinct from its ability to inhibit directly the binding of collagen to the receptor and appears to deplete GPVI from the surface of circulating platelets which may involve receptor internalisation and degradation. For newly-formed platelets in treated mice it may be that the effect is on the level of the megakaryocyte, the bone marrow progenitor of the platelet. It is important to note that the effect of F(ab) fragments of JAQ1 was comparable with that of observed for whole IgG. It is unclear how monovalent fragments might promote receptor internalisation, but these may be crosslinked by murine antibodies recognising epitopes on the rat antibody fragments (anti-species reactivity). Such crosslinking would promote receptor clustering, which may be a prerequisite for internalisation of GPVI/FcR$\gamma$ as it is for other ITAM-containing receptors (Bonnerot et al, 1998). JAQ1 is specific for mouse GPVI and has only a low affinity for human GPVI.

It may not be necessary for an antibody (fragment) recognising GPVI to block collagen recognition in order to be clinically effective since it is the depletion, rather than antagonism, of GPVI which protects the mice from thrombogenic challenge. There is only 64% homology between mouse and human GPVI (with human GPVI containing additional cytoplasmic sequences available for signalling) (Jandrot-Perrus et al 2001) and an identical effect is unlikely in humans. It would be undesirable in humans for a platelet antagonist to promote GPVI clustering: a circumstance likely to presensitize if not directly activate platelets. It is known that around 6% of patients receiving Abciximab develop anti-chimeric antibody responses (Coller, 2001). Therefore, as well as blocking collagen recognition, for an antibody to be considered as an effective GPVI antagonist it should be human so that the chances of evoking an immune response are minimised.

The present inventors have provided for the first time and characterized six GPVI specific recombinant human single chain variable domain antibody fragments (scFv) obtained from two V (variable) gene phage display libraries. During the process of scFv selection, screening and characterisation, extensive use was made of recombinant fusion soluble receptor fragments corresponding to the Ig-like ectodomains of human GPVI (hGPVI) fused to the $Ca^{2+}$-binding protein calmodulin (CaM). The fragment of hGPVI used for the majority of this study comprised residues Q1-T185 of the mature protein (referred to as hD1D2). By comparison of the sequence of hGPVI with homologous regions of certain natural killer cell inhibitory receptors of known structure, the inventors suggested that hD1D2 forms two tandem Ig-like domains and contains the collagen-binding site of the receptor. The use of CaM as an affinity tag was described by Neri et al (1995). CaM binds $Ca^{2+}$ ions and undergoes a shape change that allows it to bind target peptides bearing structural similarity to certain auto-inhibitory loops within intracellular CaM-activated kinases. The development of a peptide (which we term N9A) which binds CaM with particularly high affinity in the presence of $Ca^{2+}$ was described by Montiagiani et al (1996). Removal of $Ca^{2+}$ ions by addition of chelating agents (such as EDTA) completely reverses this binding.

Antibody molecules provided herein and obtained by the inventors exhibit notably advantageous properties, as discussed further below, especially 10B12. These antibody molecules were obtained by a combination of techniques in a strategy designed by the inventors and not previously reported.

The strategy involved combination of:

single round of positive selection, with omission of the typical antigen-phage antibody dissociation step achieved by elution. Instead the antigen-phage antibody complex was eluted from the solid phase by chelating calcium thus removing the affinity of calmodulin for the N9A peptide. It has been shown by others (de Bruin et al, 1999) that standard methods of eluting phage from immobilised antigen may not be effective for some strong binders, hence a method of retrieval which circumvents this problem is more likely to recover higher affinity scFvs.

a single round of selection based on the ability of GPVI specific phage antibodies to displace recombinant GPVI from the collagen derived mini-ligand CRP. It has been demonstrated before that specific antibodies can be obtained by using displacement with "whole" antigen, "small peptides" (typically 20 amino acids or less) or haptens. However, the selection strategy employs, for the first time, first, triple-helical, inflexible oligopeptide which mimics the ligand collagen and is specifically recognised by the recombinant receptor; second, it is necessary for the phage antibody to "remove" this bound receptor from the ligand in order to be selected. Removal is achieved probably by preventing rebinding of recombinant receptor to ligand once dissociation has occurred. To the inventors knowledge this novel strategy has not been used by others to select a "phage antibody" which is able to block the binding of ligand to its receptor.

By using a system which requires the phage to dissociate the receptor from a pre-existing ligand-receptor complex, the inventors believed that the chances of obtaining a potent inhibitory antibody would be dramatically increased.

Apart from succeeding with their strategy, the inventors were also surprised to find that a GPVI-specific scFv (prototype scFv 10B12) able to inhibit collagen-induced platelet aggregation and the adhesion of platelets to CRP, has a significant number of its contact residues in domain 1 of human GPVI. It is concluded therefore that domain 1 is critical for collagen recognition, something that was not obvious previously. The remainder of contact residues for 10B12 may be in the region linking domains 1 and 2. In contrast, the GPVI-specific, non-inhibitory scFv (prototype scFv 1C3) does not bind to domain 1, but shares a significant number of its contact residues with murine GPVI.

The excellent specificity of scFv 10B12 for hGPVI with no obvious reactivity with any other human blood cell membrane antigens, with human immunoglobulins or with other human plasma proteins means that specific binding members with the properties of scFv 10B12 are highly advantagous for binding hGPVI in its physiological setting. As demonstrated herein, scFv 10B12 blocks the interaction of hGPVI with collagen, and allows for the development of a hGPVI antagonist. GPVI is thought to be unique to the platelet/megakaryocyte lineage (Jandrot-Perrus et al, 2000) and under normal circumstances in the body is activated only by collagen. The use of specific binding members according to the invention may thus be used to provide fine control over the activation by collagen only of platelets in flowing blood. Since other pathways may act to promote thrombus formation at sites distal to those of therapeutic intervention, the risk of inappropriate bleeding may be reduced. The human origin of the V domains minimises the risk for the formation of antibodies against the reagent giving it an advantage above currently available antibody-based platelet antagonists, like the chimaeric monoclonal antibody 7E3.

ScFv 1C3 also has excellent specificity for GPVI, with no obvious reactivity with any other human blood cell membrane antigens, with human immunoglobulins or with other human plasma proteins. As demonstrated herein, it does not block the interaction of hGPVI with collagen. It binds hGPVI in an independent and non-competitive manner to 10B12, providing indication that it has a completely distinct epitope to 10B12. This allows for specific binding members with properties of scFv 1C3 to be used as and in development of a specific marker for GPVI which does not antagonise its primary function of collagen recognition. ScFv 1C3 also recognises murine GPVI, therefore may be employed to detect mGPVI under appropriate conditions.

In some preferred embodiments of the present invention, a bivalent antibody molecule containing a binding domain with properties of scFv 10B12 and a binding domain with properties of scFv 1C3 may be constructed and employed; this may be used to provide a specific binding member with a higher affinity than each of the 10B12 and 1C3 scFvs alone. Such a bivalent antibody molecule may be used to block the interaction of hGPVI with collagen and may be used therapeutically.

Also, because separate epitopes are recognised by 10B12 and 1C3, these may be used to detect hGPVI when used in combination, for instance in vitro in ELISA, or in vivo in imaging studies.

Specific binding members according to the present invention are useful in binding to and preferably antagonising action of human GPVI, with therapeutic potential in various diseases and disorders in which GPVI plays a role. Exemplary diseases and disorders are discussed further below.

As noted with reference to 1C3, in other preferred embodiments, specific binding members bind to but do not antagonise action of human GPVI.

Figure 1:
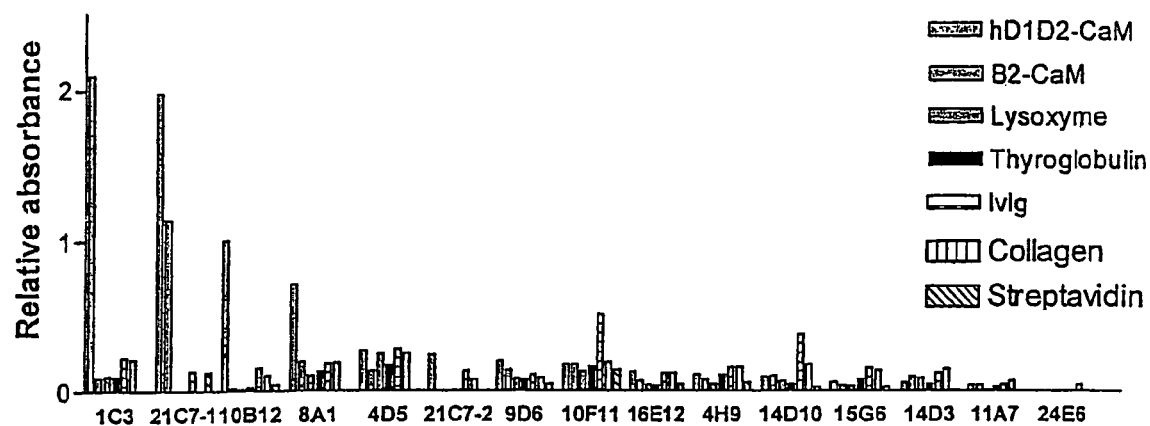
FIG. 1
Figure 1A:
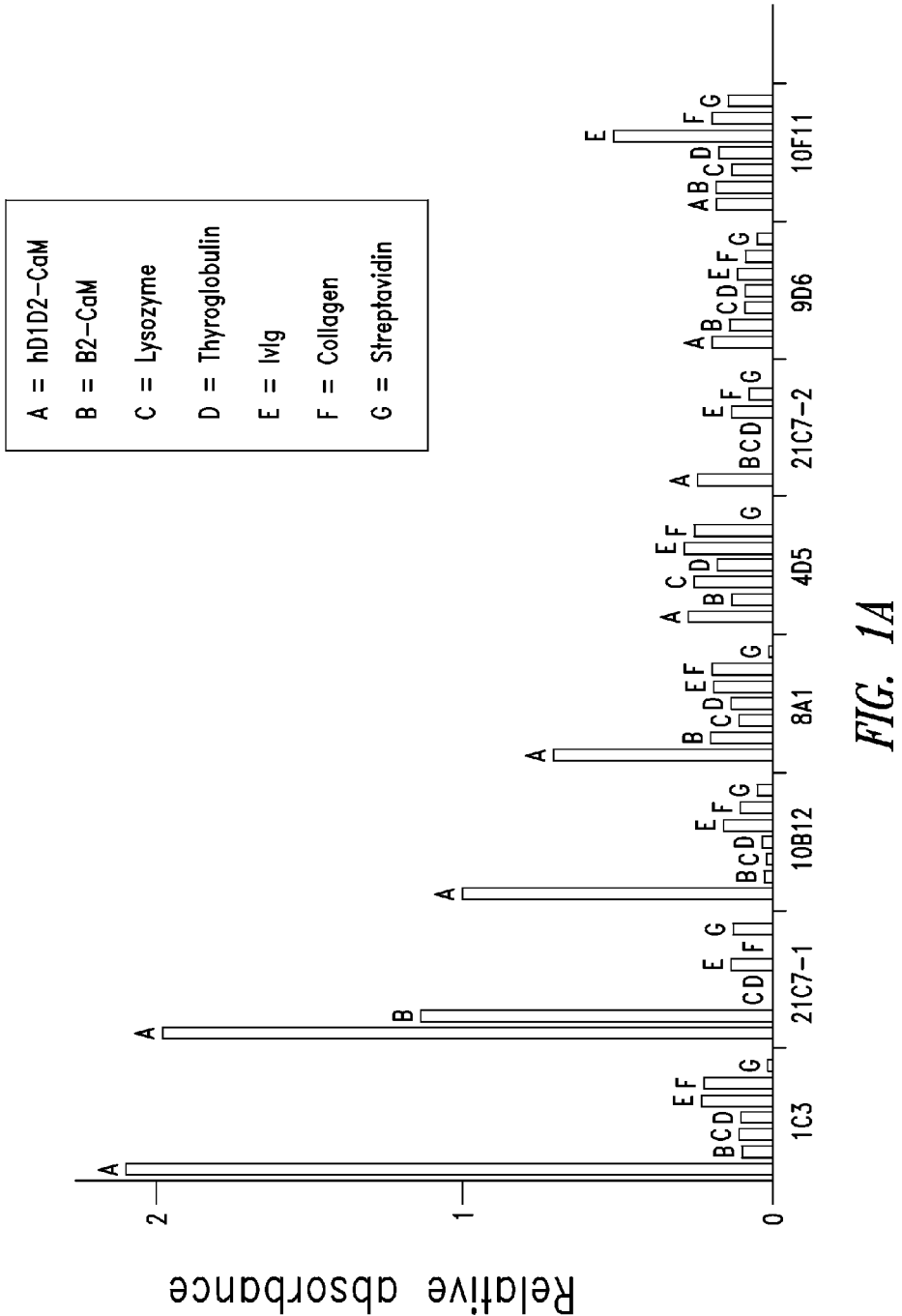
Figure 1B:
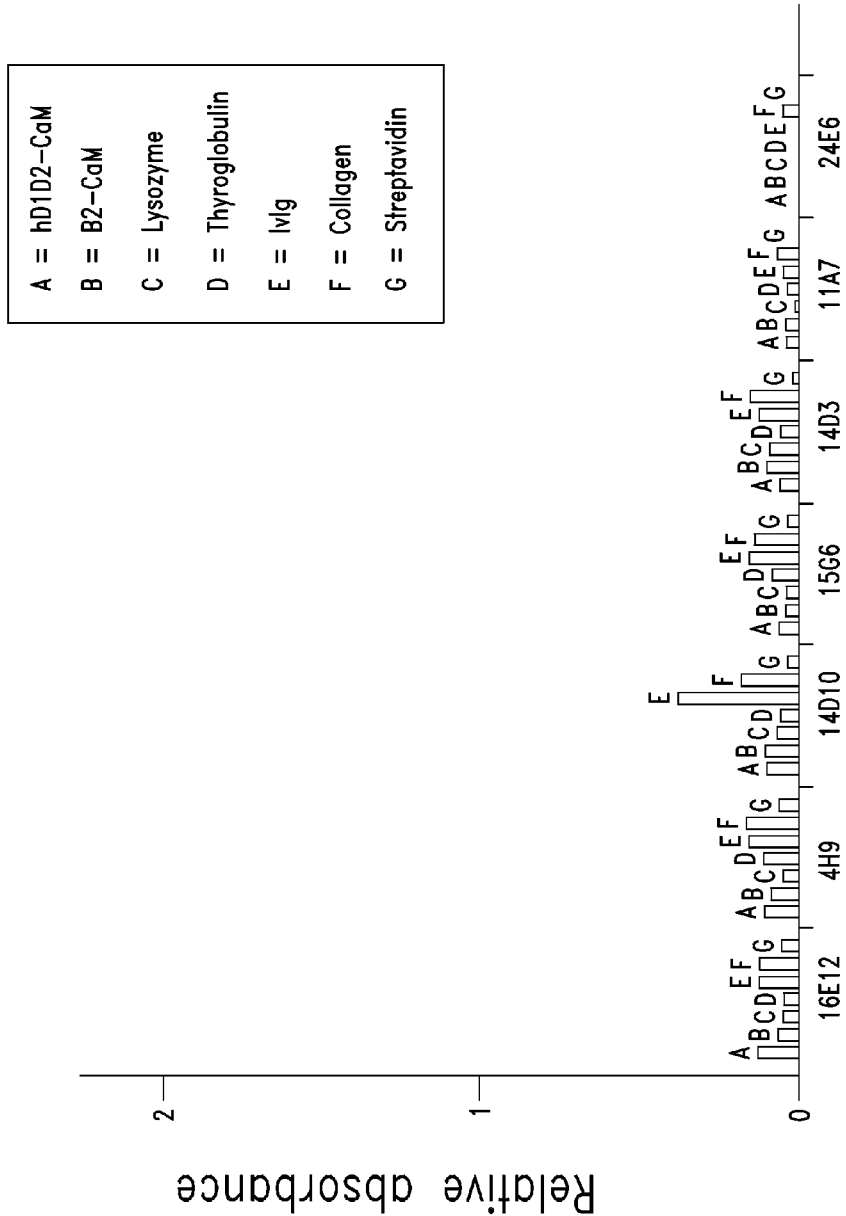

The scFvs (15 different clones) were expressed from their respective phagemid vector and tested as bacterial culture supernatants against various antigens in the direct ELISA. ScFv 10B12 was tested on each separate plate as triplicate against hD1D2-CaM (4 plates altogether) and also against plate. The relative absorbance was obtained by subtracting the reactivity of each supernatant with the uncoated plate alone from all other values with that supernatant, then dividing each value by that of scFv 10B12 against hD1D2-CaM. The absorbances for scFv 10B12 against hD1D2-CaM varied from 0.331 to 0.482 between the plates.

FIG. 2

The scFvs (15 different clones) were expressed from their respective phagemid vector and tested as bacterial culture supernatants against various antigens in the capture ELISA. ScFv 1C3 was tested on each separate plate as triplicate against hD1D2-CaM (4 plates altogether) and also against plate. The relative absorbance was obtained by subtracting the reactivity of each supernatant with the BSA-N9A-coated plate alone from all other values, then dividing each value by that of scFv 1C3 against hD1D2-CaM. The mean absolute absorbances for scFv 1C3 against hD1D2-CaM varied from 0.725 to 1.042 between the plates.

FIG. 3

ScFv 1C3 was expressed from the pUC119 vector and tested as bacterial culture supernatant, either in the direct ELISA (above) or the capture ELISA (below).—represents an uncoated plate in the direct ELISA and a BSA-N9A-coated plate in the capture ELISA.

FIG. 4

ScFv 10B12 was expressed from the pUC119 vector and tested as bacterial culture supernatant, either in the direct ELISA (above) or the capture ELISA (below).—represents an uncoated plate in the direct ELISA and a BSA-N9A-coated plate in the capture ELISA.

FIG. 5

ScFv 16E12 was expressed from the pUC119 vector and tested as bacterial culture supernatant, either in the direct ELISA (above) or the capture ELISA (below).—represents an uncoated plate in the direct ELISA and a BSA-N9A-coated plate in the capture ELISA.

FIG. 6

ScFv 8A1 was expressed from the pUC119 vector and tested as bacterial culture supernatant, either in the direct ELISA (above) or the capture ELISA (below).—represents an uncoated plate in the direct ELISA and a BSA-N9A-coated plate in the capture ELISA.

FIG. 7

The purified scFvs 10B12 and 1C3 were tested at 10 µg/ml for binding to human and mouse D1D2-CaM in the capture ELISA.

FIG. 8

The purified scFvs 10B12, 1C3 and 2F2 (anti-GPIIbIIIa) were tested at 10 µg/ml for binding to hD1-CaM, hD2-CaM or hD1D2-CaM in the capture ELISA

FIG. 9

The effect of bacterial culture supernatants, containing scFvs expressed from the pUC119 vector, on binding of hD1D2-CaM to Collagen-Related Peptide (CRP) was studied by ligand binding assay. hD1D2-CaM was used at two different concentrations: 1.0 and 2.5 µg/ml. hD1D2-CaM binding to CRP in the absence of scFvs was represented as 100%, or "uninhibited" binding at that concentration. Mean absolute absorbance values for hD1D2-CaM binding to CRP were 0.477 at 2.5 µg/ml and 0.260 at 1.0 µg/ml. A scFv recognising GPIIbIIIa, 2F2 was used as a negative control. Each bar represents the mean of triplicate wells+SEM.

FIG. 10

The effect of purified scFvs on binding of hD1D2-CaM to Collagen-Related Peptide (CRP) was studied by ligand binding assay. hD1D2-CaM binding to CRP in the absence of scFvs was represented as 100%, or "uninhibited" binding. Mean absolute absorbance value for hD1D2-CaM binding to CRP was 0.265. hD1D2-CaM was used at 10 µg/ml. A scFv recognising GPIIbIIIa, 2F2, was used as a negative control. Each point represents the mean of triplicate wells±SEM.

FIG. 11

The effects of purified scFvs 10B12, 1C3 and 2D4 (anti-HLA-A2/A28 and related structures) on platelet activation by collagen were assessed by platelet aggregometry in plasma. ScFvs or buffer were added to platelets (arrow A) and incubated for 5 minutes. Then collagen fibres (final concentration of 1 µg/ml) were added (arrow B). (a) ScFvs were added to 50 µg/ml (final); (b) 10B12 scFv was added to 10 µg/ml (final).

FIG. 12

The effects of purified scFv 10B12 on the response of platelets to agonists other than collagen were assessed by platelet aggregometry in plasma. 10B12 scFv was added at 10 µg/ml (final) and incubated for 5 minutes (arrow A) prior to addition of the agonists. ADP (at 30 µM final) or U46619 (at 1 µM final) were then added (arrow B). A further amount of U44619 was added (to 2 µM final) after a further 6 minutes (arrow C).

FIG. 13

The binding response (in arc.sec$^{-1}$) of purified scFvs to immobilised hD1D2-CaM was observed by biosensor. Arrows record the immobilisation of hD1D2-CaM, followed by two aliquots of 1C3 then three aliquots of 10B12, with both scFvs binding to saturation The experiment was repeated (cell 1 and cell 2).

FIG. 14

Binding to platelets of the purified scFv 10B12 or 1C3 or both added together (10B12+C3) at different concentrations was observed by flow cytometry. One donor platelet sample was used. The scFv 2D4 (anti-HLA-A2/A28 and related structures) was used as negative control. The donor sample was HLA-A2 negative (specifically HLA A1 A29 B8 B50). Each point represents the median fluorescence intensity of 10000 events.

FIG. 15

Binding of the purified scFvs 10B12 and 1C3 to platelets was studied with 6 different blood donors by flow cytometry. Donors D1-D4 were studied as fresh blood samples, whereas D5-D6 were recovered from cryopreservation before use. D5 was heterozygous (Leucine/Valine) for the polymorphism at amino acid 83 in mature human GP VI. The scFv 2D4 (anti-HLA-A2/A28 and related structures) was used as control. The HLA types of the donors D1-D4 were A1 A24 B8 B51, A2 B51, A1 A30 B51 B37 and A3 B7, respectively. Plt=untreated platelets; 9E10=platelets–scFv, +9E10+anti-mouse FITC; Fitc=platelets–scFv, –9E10, +anti-mouse FITC; 10B12, 1C3 and 2D4=platelets+corresponding scFv, +9E10, +anti-mouse FITC.

FIG. 16

The reactivity of the purified scFvs with granulocytes and lymphocytes was assessed by flow cytometry. Cells from two donors were prepared. These were both positive for HLA-A2/28 (or related structures). In the same experiment, the scFvs did react with platelets from each donor (data not shown here). ScFvs were used at 50 µg/ml.

FIG. 17

The binding of purified scFvs to immobilised hD1D2-CaM was observed by biosensor. Arrows record the immobilisation of hD1D2-CaM in both cells, followed by two aliquots of 10B12 to cell 1 and three aliquots of 1C3 to cell 2, to give saturation. An aliquot of 16E12 was added to each cell and the response observed.

FIG. 18

Binding of the purified scFv 1C3 (10 µg/ml) to platelets of 89 different donors was studied by flow cytometry. The median fluorescence intensity of 10000 events for each donor sample was obtained. The frequency of donors whose platelets had a given median fluorescence intensity is shown.

FIG. 19.

FIG. 19A: Fastplot figure of association/dissociation curves of different concentrations purified, monomeric scFv 1C3 binding to hD1D2-CaM observed by biosensor.

FIG. 19B: Fastfit figure showing $K_{on}$ vs. [scFv], used to calculate $K_D$ for 1C3. Data were obtained from the experiment shown in FIG. 19A.

FIG. 19C: Fastplot figure of association/dissociation curves of different concentrations purified, monomeric scFv 10B12 binding to hD1D2-CaM observed by biosensor.

FIG. 19D: Fastfit figure showing $K_{on}$ vs. [scFv], used to calculate $K_D$ for 10B12. Data were obtained from the experiment shown in FIG. 19C.

FIG. 20

The effects of different, purified antibodies (scFv 10B12 and monoclonal antibody 6F1 (recognising the I-domain of integrin α2)) on the adhesion of platelets to collagen was observed by the platelet adhesion assay. HBS=HEPES buffered saline, PD collagen 1 =pepsin digested, soluble collagen 1. Ethicon and GPP-GFOGER as described herein.

FIG. 21

The effects of different concentrations of purified scFv 10B12 on adhesion of platelets to CRP was observed by the platelet adhesion assay.

FIG. 22

After preincubation with hD1D2-His (at concentrations from 1 to 300 μg/ml), the binding of purified scFvs 1C3, 10B12 (at 20 μg/ml) to platelets was observed by flow cytometry. Each point represents the median fluorescence intensity of 10000 events.

FIG. 23

The effects of purified scFvs on adhesion and activation of platelets in whole blood was observed using a perfusion assay.

Blood obtained from 6 separate donors was drawn over collagen-coated coverslips in the presence of scFvs 10B12, 1C3 and 2D4 (anti HLA-A2/A28 and related structures) at 50 μg/ml. The surface area covered by adherent platelets was later quantified by image analysis, being expressed as a percentage of the total surface area sampled. At least twenty distinct fields were sampled from each coverslip. Bars represent the mean coverage of three separate coverslips. Donors 2 and 3 are positive for HLA-A2 and would be bound by scFv 2D4. Donors 4-6 are HLA-A2 negative and would not be bound by 2D4. The HLA type of Donor 1 is uncertain.

FIG. 24

Figure 24:
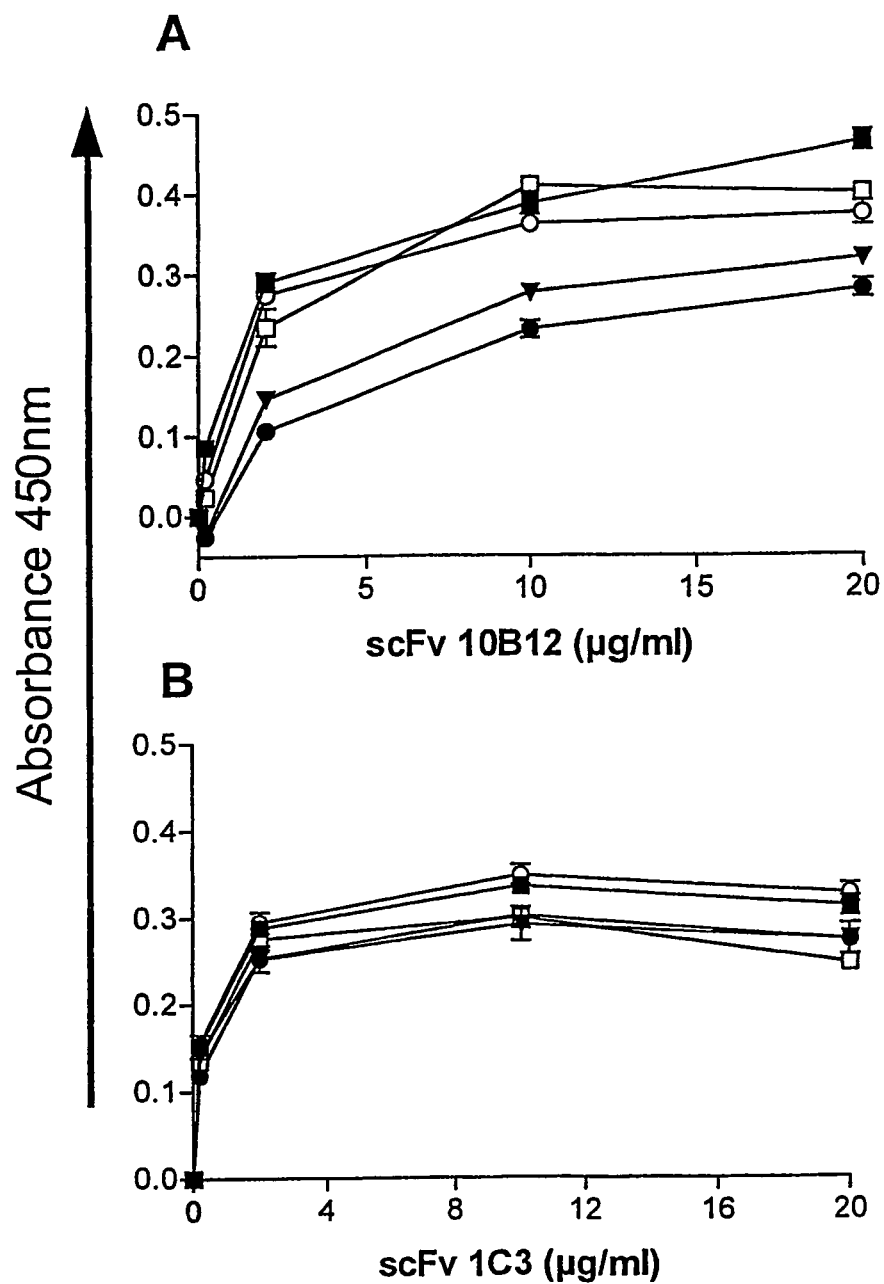

Binding of scFvs 10B12 and 1C3 to hD1D2 and mutants by ELISA. FIG. 24A: Binding of 10B12 to hD1D2 (closed squares), R117P (open squares), R166S (open circles), K59E (closed circles) and triple mutant (closed, inverted triangles).

FIG. 24B: Binding of 1C3 to the antigens as represented in FIG. 24A.

Points represent mean±SD of triplicate wells in one experiment, representative of two identical experiments.

FIG. 25

The effects of purified scFv 10B12 on the response of platelets to agonists other than collagen were assessed by platelet aggregometry in plasma. ScFv 10B12 was added at 50 μg/ml (final) and incubated for 5 minutes before addition of agonists. The samples were incubated for a further 5 minutes and the % aggregation recorded. Each bar represents the mean+SD for tests performed on 3 donors. The concentrations of agonist used were: Collagen fibres, (1 μg/ml), adenosine 5'-diphosphate (ADP) (5 μM), U46619 (5 μM), thrombin receptor activating peptide (TRAP) (10 μM), epinephrine (EPI) (4 μM).

FIG. 26

This shows the effect of increasing concentrations of 10B12 on the deposition of platelets under flow, measured as surface coverage (filled squares) or as phosphatidyl-serine (PS) expressing surface (open circles) The decline in surface coverage was not significant, whereas the reduction in PS-expression was statistically significant ($p<0.01$), indicating the capacity of 10B12 to inhibit collagen-stimulated procoagulant activity.

FIG. 27

This shows the effect of preincubation of blood with 10B12 (50 μg/ml) on the distribution of platelet aggregate sizes deposited on collagen fibres under flow.

Figure 27:
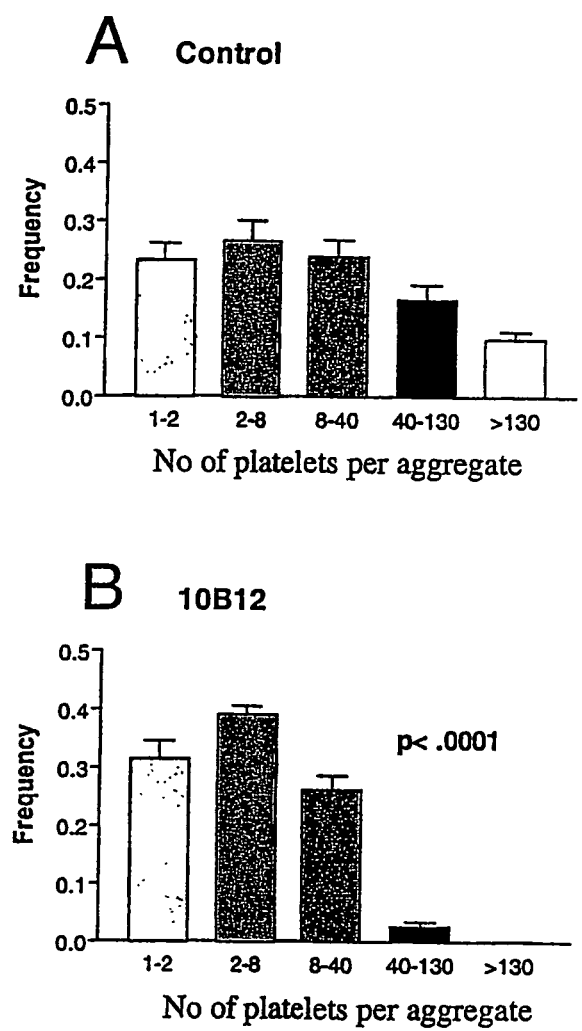

FIG. 27A shows data from Control collagen surfaces, figures beneath the histogram representing the number of platelets per category, whose frequency is shown on the y axis.

FIG. 27B shows data obtained after 10B12 treatment, which abolished the occurrence of large aggregates, shifting the distribution significantly towards single platelets.

The following sequences are disclosed herein:
SEQ ID NO. 1 10B12 VH encoding nucleotide sequence
SEQ ID NO. 2 10B12 VH amino acid sequence
SEQ ID NO. 3 10B12 VL encoding nucleotide sequence
SEQ ID NO. 4 10B12 VL amino acid sequence
SEQ ID NO. 5 10B12 VH CDR1 amino acid sequence
SEQ ID NO. 6 10B12 VH CDR2 amino acid sequence
SEQ ID NO. 7 10B12 VH CDR3 amino acid sequence
SEQ ID NO. 8 10B12 VL-CDR1 amino acid sequence
SEQ ID NO. 9 10B12 VL CDR2 amino acid sequence
SEQ ID NO. 10 10B12 VL CDR3 amino acid sequence
SEQ ID NO. 11 1C3 VH encoding nucleotide sequence
SEQ ID NO. 12 1C3 VH amino acid sequence
SEQ ID NO. 13 1C3 VL encoding nucleotide sequence
SEQ ID NO. 14 1C3 VL amino acid sequence
SEQ ID NO. 15 1C3 VH CDR1 amino acid sequence
SEQ ID NO. 16 1C3 VH CDR2 amino acid sequence
SEQ ID NO. 17 1C3 VH CDR3 amino acid sequence
SEQ ID NO. 18 1C3 VL CDR1 amino acid sequence
SEQ ID NO. 19 1C3 VL CDR2 amino acid sequence
SEQ ID NO. 20 1C3 VL CDR3 amino acid sequence
SEQ ID NO. 21 CRP (wherein 0 is hydroxyproline)
SEQ ID NO. 22 GPP10
SEQ ID NO. 23 primer LMB3
SEQ ID NO. 24 primer fd-seq1
SEQ ID NO. 25 primer PHEN-SEQ In one aspect, the present invention provides a specific binding member which binds human GPVI and which comprises the 10B12 VH domain (SEQ ID NO. 2) and/or the 10B12 VL domain (SEQ ID NO. 4)

Generally, a VH domain is paired with a VL domain to provide an antibody antigen binding site, although as discussed further below a VH domain alone may be used to bind antigen. In one preferred embodiment, the 10B12 VH domain (SEQ ID NO. 2) is paired with the 10B12 VL domain (SEQ ID NO. 4), so that an antibody antigen binding site is formed comprising both the 10B12 VH and VL domains. In other embodiments, the 10B12 VH is paired with a VL domain other than the 10B12 VL. Light-chain promiscuity is well established in the art.

One or more CDRs may be taken from the 10B12 VH or VL domain and incorporated into a suitable framework. This is discussed further below. 10B12 VH CDR's 1, 2 and 3 are shown in SEQ ID NO.'s 5, 6 and 7, respectively. 10B12 VL CDR's 1, 2 and 3 are shown in SEQ ID NO.'s 8, 9 and 10, respectively.

Variants of the VH and VL domains and CDRs of which the sequences ate set out herein and which can be employed in specific binding members for human GPVI can be obtained by means of methods of sequence alteration or mutation and screening. Such methods are also provided by the present invention.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1. Alterations may be made in one or more framework regions and/or one or more CDR's.

A specific binding member according to the invention may be one which competes for binding to antigen with any specific binding member which both binds the antigen and comprises a specific binding member, VH and/or VL domain disclosed herein, or VH CDR3 disclosed herein, or variant of any of these.

Competition between binding members may be assayed easily in vitro, for example using ELISA and/or by tagging a specific reporter molecule to one binding member which can be detected in the presence of other untagged binding member(s), to enable identification of specific binding members which bind the same epitope or an overlapping epitope.

Thus, a further-aspect of the present invention provides a specific binding member comprising a human antibody antigen-binding site which competes with 10B12 or 1C3 for binding to human GPVI.

Various methods are available in the art for obtaining antibodies against human. GPVI and which may compete with 10B12 or 1C3 for binding to human GPVI.

As noted, the epitope recognised by 10B12 contains residues in domain 1 of GPVI. 1C3 does not bind domain 1 and recognises an epitope that allows for its cross-reactivity between human and murine GPVI. The epitope of 10B12 is not that of 1C3.

In a further aspect, the present invention provides a method of obtaining one or more specific binding members able to bind the antigen, the method including bringing into contact a library of specific binding members according to the invention and said antigen, and selecting one or more specific binding members of the library able to bind said antigen.

The library may be displayed on the surface of bacteriophage particles, each particle containing nucleic acid encoding the antibody VH variable domain displayed on its surface, and optionally also a displayed VL domain if present.

Following selection of specific binding members able to bind the antigen and displayed on bacteriophage particles, nucleic acid may be taken from a bacteriophage particle displaying a said selected specific binding member. Such nucleic acid may be used in subsequent production of a specific binding member or an antibody VH variable domain (optionally an antibody VL variable domain) by expression from nucleic acid with the sequence of nucleic acid taken from a bacteriophage particle displaying a said selected specific binding member.

An antibody VH variable domain with the amino acid sequence of an antibody VH variable domain of a said selected specific binding member may be provided in isolated form, as may a specific binding member comprising such a VH domain.

Ability to bind human GPVI may be further tested, also ability to compete with 10B12 or 1C3 for binding to human GPVI. Ability to antagonise action of GPVI may be tested, as discussed further below.

A specific binding member according to the present invention may bind human GPVI with the affinity of 10B12 or 1C3.

A specific binding member according to the present invention may inhibit collagen-induced platelet aggregation and/or the adhesion of platelets to Collagen-Related Peptide (CRP) with the potency of 10B12.

Platelet adhesion to collagen and collagen-like molecules (including e.g. CRP and GFOGER-GPP) may be assessed under static conditions and/or under conditions of flow, e.g. where whole blood is perfused over a collagen-coated surface, such that shear rate experienced by platelets compares to that experienced in human circulation, for example a shear rate of $1600$ $s^{-1}$.

In a static adhesion assay, a platelet suspension is incubated without agitation in wells pre-coated with a collagen-like molecule. In this case direct adhesion of platelets to CRP, entirely via GPVI, can be observed.

In a perfusion assay for assessment under conditions of flow, whole blood may be caused to flow over a surface pre-coated with such collagen like molecules, such that the shear rate experienced by the platelets in contact with that surface is comparable with that which would be experienced in the human arterial circulation. Under these conditions direct adhesion via GPVI cannot occur (Verkleij et al 1998), therefore adhesion is through other receptors, in particular $\alpha2\beta1$. The effect of GPVI blockade with anti-GPVI antibody molecule is therefore to suppress platelet activation, a necessary prerequisite for adhesion via other receptors.

A most pronounced effect of GPVI blockade in this system may be observed under the conditions used in the perfusion assay described herein (with reference to FIG. 23), in particular with respect to the type of collagen used (human type III) and the shear rate employed ($1600s^{-1}$).

Binding affinity and neutralisation potency of different specific binding members can be compared under appropriate conditions.

Figure 26:
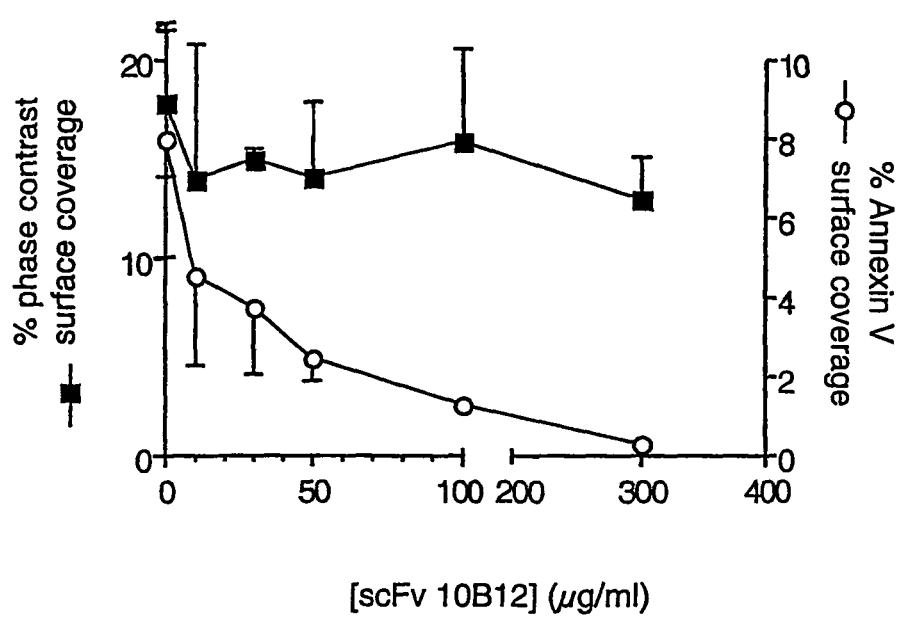

A specific binding member according to the present invention may inhibit the expression of procoagulant activity on the extracellular surface of platelets exposed to collagen, for instance when adhering to a collagen-containing surface. Procoagulant activity may be represented by phosphatidyl serine exposure, which can be measured by the binding of Annexin-V, for instance in the advance perfusion assay described herein with reference to FIG. 26.

In addition to antibody sequences, a specific binding member according to the present invention may comprise other amino acids, e.g. forming a peptide or polypeptide, such as a folded domain, or to impart to the molecule another functional characteristic in addition to ability to bind antigen. Specific binding members of the invention may carry a detectable label, or may be conjugated to a toxin or enzyme (e.g. via a peptidyl bond or linker).

In further aspects, the invention provides an isolated nucleic acid which comprises a sequence encoding a specific binding member, VH domain and/or VL domain according to the present invention, and methods of preparing a specific binding member, a VH domain and/or a VL domain of the invention, which comprise expressing said nucleic acid under conditions to bring about production of said specific binding member, VH domain and/or VL domain, and recovering it.

Specific binding members according to the invention may be used in a method of treatment or diagnosis of the human or animal body, such as a method of treatment (which may include prophylactic treatment) of a disease or disorder in a human patient which comprises administering to said patient an effective amount of a specific binding member of the invention. Conditions treatable in accordance with the present invention include those discussed elsewhere herein.

A further aspect of the present invention provides nucleic acid, generally isolated, encoding an antibody VH variable domain and/or VL variable domain disclosed herein.

Another aspect of the present invention provides nucleic acid, generally isolated, encoding a VH CDR or VL CDR sequence disclosed herein, especially a VH CDR selected from SEQ ID NO.'s 5, 6 and 7 or a VL CDR selected from SEQ ID NO.'s 8, 9 and 10, most preferably 10B12 VH CDR3 (SEQ ID NO. 7).

A further aspect provides a host cell transformed with nucleic acid of the invention.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and specific binding members comprising a VH and/or VL domain are provided as further aspects of the present invention.

A method of production may comprise a step of isolation and/or purification of the product.

A method of production may comprise formulating the product into a composition including at least one additional component, such as a pharmaceutically acceptable excipient.

These and other aspects of the invention are described in further detail below.

Terminology

Specific Binding Member

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

Antibody Molecule

This describes an immunoglobulin whether natural or partly or wholly synthetically produced. The term also covers any polypeptide or protein comprising an antibody binding domain. Antibody fragments which comprise an antigen binding domain are such as Fab, scFv, Fv, dAb, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody molecule" should be construed as covering any specific binding member or substance having an antibody antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising a scFv joined to a CH1 domain may also be made (S. Hu et al, Cancer Res., 56, 3055-3061, 1996).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against GPVI, then a library can be made where the other arm is varied and an antibody of appropriate specificity selected. Bispecific whole antibodies may be made by knobs-into-holes engineering (J. B. B. Ridgeway et al, Protein Eng., 9, 616-621, 1996).

Antigen Binding Domain

This describes the part of an antibody molecule which comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). Preferably, an antigen binding domain comprises an antibody light chain variable region (VL) and an antibody heavy chain variable region (VH).

Specific

This may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

Typically, specificity may be determined by means of a binding assay such as ELISA employing a panel of antigens, e.g. as disclosed herein with reference to FIG. 1. A specific binding member according to the present invention may recognise GPVI on cells of the platelet/megakaryocyte lineage, and not other human blood cells, in particular granulocytes, lymphocytes and erythrocytes. Reactivity of a specific binding member according to the invention with human platelets may be abolished by competition with recombinant GPVI.

Specificity may also be confirmed by means of comparison between the effective inhibitory dose in a collagen-binding assay such as platelet aggregometry conducted in plasma or whole blood perfusion and saturable binding of washed platelets in flow cytometry. Results obtained for 10B12, for example, show comparable effective inhibitor doses indicating that other blood constituents had no significant effect on the binding of 10B12 to hGPVI.

Comprise

This is generally used in the sense of include, that is to say permitting the presence of one or more features or components.

Isolated

This refers to the state in which specific binding members of the invention, or nucleic acid encoding such binding members, will generally be in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, amino acid substitutions may be made in the CDR and/or VH or VL domain.

The structure for carrying a CDR of the invention will generally be of an antibody heavy or light chain sequence or substantial portion thereof in which the CDR is located at a location corresponding to the CDR of naturally occurring VH and VL antibody variable domains encoded by rearranged immunoglobulin genes. The structures and locations of immunoglobulin variable domains may be determined by reference to (Kabat, E. A. et al, Sequences of Proteins of Immunological Interest. 4th Edition. US Department of Health and Human Services. 1987, and updates thereof, now available on the Internet (http://immuno.bme.nwu.edu or find "Kabat" using any search engine).

Preferably, a CDR amino acid sequence substantially as set out herein is carried as a CDR in a human variable domain or a substantial portion thereof. The VH CDR3 sequences substantially as set out herein represent preferred embodiments of the present invention and it is preferred that each of these is carried as a VH CDR3 in a human heavy chain variable domain or a substantial portion thereof.

Variable domains employed in the invention may be obtained from any germ-line or rearranged human variable domain, or may be a synthetic variable domain based on consensus sequences of known human variable domains. A CDR sequence of the invention (e.g. CDR3) may be introduced into a repertoire of variable domains lacking a CDR (e.g. CDR3), using recombinant DNA technology.

For example, Marks et al (*Bio/Technology*, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer (*Nature*, 1994, 370:389-391), who describes the technique in relation to a β-lactamase gene but observes that the approach may be used for the generation of antibodies.

A further alternative is to generate novel VH or VL regions carrying a CDR-derived sequences of the invention using random mutagenesis of one or more selected VH and/or VL genes to generate mutations within the entire variable domain. Such a technique is described by Gram et al (1992, *Proc. Natl. Acad. Sci.*, USA, 89:3576-3580), who used error-prone PCR.

Another method which may be used is to direct mutagenesis to CDR regions of VH or VL genes. Such techniques are disclosed by Barbas et al, (1994, *Proc. Natl. Acad. Sci., USA*, 91:3809-3.813) and Schier et al (1996, *J. Mol. Biol.* 263:551-567).

All the above described techniques are known as such in the art and in themselves do not form part of the present invention. The skilled person will be able to use such techniques to provide specific binding members of the invention using routine methodology in the art.

A further aspect of the invention provides a method for obtaining an antibody antigen-binding domain specific for human GPVI antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations for to identify a specific binding member or an antibody antigen binding domain specific for human GPVI and optionally with one or more of preferred properties, preferably ability to inhibit collagen-induced platelet aggregation and/or the adhesion of platelets to Collagen-Related Peptide (CRP), or ability to specifically detect GPVI without inhibiting such collagen recognition. Said VL domain may have an amino acid sequence which is substantially as set out herein.

An analogous method may be employed in which one or more sequence variants of a VL domain disclosed herein are combined with one or more VH domains.

A further aspect of the invention provides a method of preparing a specific binding member specific for human GPVI, which method comprises:
(a) providing a starting repertoire of nucleic acids encoding a VH domain which either include a CDR3 to be replaced or lack a CDR3 encoding region;
(b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;
(c) expressing the nucleic acids of said product repertoire;
(d) selecting a specific binding member specific for a GPVI; and
(e) recovering said specific binding member or nucleic acid encoding it.

Again, an analogous method may be employed in which a VL CDR3 of the invention is combined with a repertoire of nucleic acids encoding a VL domain which either include a CDR3 to be replaced or lack a CDR3 encoding region.

Similarly, one or more, or all three CDRs may be grafted into a repertoire of VH or VL domains which are then screened for a specific binding member or specific binding members specific for GPVI.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more details below.

Although in a preferred aspect of the invention specific binding members comprising a pair of VH and VL domains are preferred, single binding domains based on either VH or VL domain sequences form further aspects of the invention. It is known that single immunoglobulin domains, especially VH domains, are capable of binding target antigens in a specific manner.

In the case of either of the single chain specific binding domains, these domains may be used to screen for complementary domains capable of forming a two-domain specific binding member able to bind GPVI.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting-two-chain specific binding member is selected in accordance with phage display techniques such as those described in that reference. This technique is also disclosed in Marks et al, ibid.

Specific binding members of the present invention may further comprise antibody constant regions or parts thereof. For example, a VL domain may be attached at its C-terminal end to antibody light chain constant domains including human Cκ or Cλ chains, preferably Cλ chains. Similarly, a specific binding member based on a VH domain may be attached at its C-terminal end to all or part of an immunoglobulin heavy chain derived from any antibody isotype, e.g. IgG, IgA, IgE and IgM and any of the isotype sub-classes, particularly IgG1 and IgG4. IgG4 is preferred. Fc regions such as Δnab and Δnac as disclosed in WO99/58572 may be employed.

Specific binding members of the invention may be labelled with a detectable or functional label. Detectable labels include radiolabels such as $^{131}$I, or $^{99}$Tc, which may be attached to antibodies of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin.

Specific binding members of the present invention are designed to be used in methods of diagnosis or treatment in human or animal subjects, preferably human.

Accordingly, further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

Clinical indications in which an anti-GPVI antibody may be used to provide therapeutic benefit include any condition in which collagen recognition by GPVI has pathological consequences, for example in cardiovascular conditions such as thrombosis, including for example arterial thrombosis occurring in blood vessel wall disease (e.g. coronary artery thrombosis, which causes myocardial infarction). Similar thrombotic processes may occur in other serious conditions at diverse anatomical locations, for instance in the cerebral vasculature, leading to stroke, or in the peripheral extremities. In the latter case for instance, patients with intermittent claudication may be treated. Antibody-mediated blockade of GPVI may be used and be beneficial during therapeutic procedures which induce damage to the blood vessel wall, for instance vascular surgery. Examples of vascular surgery may include, but are not limited to, coronary artery bypass grafting, balloon angioplasty and stenting. In other, unrelated disease processes, circulating platelets may be exposed to collagens where they may contribute to local thrombotic effects and to the inflammatory processes which ensue. An example of the latter occurs in hepatitis where the hepatic circulation is compromised by the disease. In addition diseases of generalised platelet activation such as thrombocytopenic purpura and haemolytic uraemic syndrome and other clinical conditions with disseminated intravascular coagulation may be ameliorated. Furthermore multi-organ damage because of arterial insufficiency in patients with homozygous sickle disease may be beneficially affected by inhibiting the activation of platelets via GPVI. Similarly kidney damage by platelet and fibrin disposition on the glomerular membrane and other conditions such as micro-angiopathic vasculitides may be treated by antibody-mediated GPVI blockade.

Anti-GPVI treatment in accordance with the present invention may be used to provide clear benefit for patients with cardiovascular disease, especially those who have undergone corrective vessel surgery or angioplasties with or without stenting. Anti-GPVI treatment may be given by injection (e.g. intravenously) or by local delivery methods (e.g. pre-coating of stents or other indwelling devices). Anti-GPVI may be delivered by gene-mediated technologies. Alternative formulation strategies may provide preparations suitable for oral or suppository route. The route of administration may be determined by the physicochemical characteristics of the treatment, by special considerations for the disease, to optimise efficacy or to minimise side-effects.

GPVI deficiency is only associated with a mild bleeding phenotype in humans (Moroi et al, 1989) and mice (Nieswandt et al 2001b), and GPVI has limited cellular distribution. This allows for anti-GPVI treatment highly suitable for use in combination treatments, where a significant synergistic effect is likely. For example, platelet activation by primary stimuli such as collagen binding to GPVI may be powerfully amplified by products or factors secreted from the platelet during the activation process, or produced at the platelet surface after activation. Thus, more complete inhibition of platelet function may be achieved by blockade of GPVI together with antagonism of the amplification processes. Agents useful for this purpose might include inhibitors of the thromboxane pathway such as aspirin, inhibitors of the ADP pathway such as clopidogrel or ADP receptor antagonists, and inhibitors of thrombin such as heparin or hirudin.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; see Ledermann J. A. et al. (1991) Int. J. Cancer 47: 659-664; Bagshawe K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 0.5 mg-1.0 g, and this may be administered as a bolus intravenously. Other modes of administration include intravenous infusion over several hours, to achieve a similar total cumulative dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

A further mode of administration employs precoating of, or otherwise incorporation into, indwelling devices, for which the optimal amount of antibody will be determined by means of appropriate experiments.

An antibody molecule in some preferred embodiments of the invention is a monomeric fragment, such as F(ab) or scFv. Such antibody fragments may have the advantage of a relatively short half life and less risk of platelet activation, which may be caused by receptor clustering. Clustering which gives rise to platelet activation could be either of GPVI molecules or of GPVI with FcγRII molecules, for instance.

If a whole antibody, is used, it is preferably in a form that is unable to activate and/or destroy platelets. The IgG4 isotype or alternatively "designer" isotypes derived from the IgG1 backbone (novel Fc gene constructs WO99/58572, Clark, Armour, Williamson) are preferred choices. Smaller antibody fragments may be used, such as F(ab')2. In addition, whole antibodies or fragments (e.g. F(ab')2 or diabodies) with dual epitope specificity (e.g. for the epitopes recognised by scFv 10B12 and/or scFv 1C3) may be used. Although such an embodiment may promote receptor clustering, a high association rate to individual receptors may rule out this problem.

Specific binding members of the present invention will usually be administered in the form of a pharmaceutical composition, which may comprise at least one component in addition to the specific binding member.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may include a stent or other indwelling device.

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. asprin, paracetamol, ibuprofen or ketoprofen) or opiates such as morphine, or anti-emetics.

The present invention provides a method comprising causing or allowing binding of a specific binding member as provided herein to GPVI. As noted, such binding may take place in vivo, e.g. following administration of a specific binding member, or nucleic acid encoding a specific binding member, or it may take place in vitro, for example in ELISA, Western blotting, immunocytochemistry, immuno-precipitation or affinity chromatography.

In employing 10B12 and 1C3 for the detection of GPVI as disclosed herein, use may be made of the ability of each scFv to bind independently to GPVI. This capacity may be employed, for instance, to produce a signal only when both scFvs bind to GPVI (e.g. by fluorescent resonance energy transfer or by sandwich ELISA where one scFv is used to capture GPVI and the other is used to detect GPVI). It may also be employed to produce a cumulative signal (e.g. where both scFvs are attached to the same reporter molecule and GPVI is immobilised by another means).

The amount of binding of specific binding member to GPVI may be determined. Quantitation may be related to the amount of the antigen in a test sample, which may be of diagnostic interest.

The reactivities of antibodies on a sample may be determined by any appropriate means. Radioimmunoassay (RIA) is one possibility. Radioactive labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of a specific binding member as above for measuring antigen levels in a competition assay, that is to say a method of measuring the level of antigen in a sample by employing a specific binding member as provided by the present invention in a competition assay. This may be where the physical separation of bound from unbound antigen is not required. Linking a reporter molecule to the specific binding member so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of antigen directly, by employing a specific binding member according to the invention for example in a biosensor system.

The mode of determining binding is not a feature of the present invention and those skilled in the art are able to choose a suitable mode according to their preference and general knowledge.

The present invention further extends to a specific binding member which competes for binding to GPVI with any specific binding member which both binds the antigen and comprises a V domain including a CDR with amino acid substantially as set out herein or a V domain with amino acid sequence substantially as set out herein. Competition between binding members may be assayed easily in vitro, for example by tagging a specific reporter molecule to one binding member which can be detected in the presence of other untagged binding member(s), to enable identification of specific binding members which bind the same epitope or an overlapping epitope. Competition may be determined for example using ELISA or flow cytometry.

A competition reaction may be used to select one or more specific binding members such as derivatives of 10B12 and 1C3, which may have one or more additional or improved properties.

This is analogous to the selection method for 10B12 in accordance with the invention, except that GPVI is not eluted from its mini-ligand but from an antibody molecule. This may be important as it should yield a greater proportion of daughter antibodies which directly compete with the parent. Indeed such daughter antibodies as are selected may have a greater affinity for the antigen than the parent (allowing for enhancements in avidity which may result from the display of more than one antibody molecule per phage). Current methods of selecting for "daughter" phage antibodies of improved affinity include:

i) using concentrations of (labelled) target antigen lower than the dissociation constant of the original parent antibody
ii) using excess unlabelled target antigen as a competitor as demonstrated in Hawkins et al (1992). However, they do not necessarily specify that the "improved" antibody must displace/occupy the same epitope as the parent. Incorporating the elution step should yield a higher proportion of daughter antibodies which do displace the parent. Daughter antibodies selected in this way may bind a very similar epitope to the parent antibody, but with a greater affinity.

In testing for competition a peptide fragment of the antigen may be employed, especially a peptide including an epitope of interest. A peptide having the epitope sequence plus one or more amino acids at either end may be used. Such a peptide may be said to "consist essentially" of the specified sequence. Specific binding members according to the present invention may be such that their binding for antigen is inhibited by a peptide with or including the sequence given. In testing for this, a peptide with either sequence plus one or more amino acids may be used.

Specific binding members which bind a specific peptide may be isolated for example from a phage display library by panning with the peptide(s).

The present invention further provides an isolated nucleic acid encoding a specific binding member of the present invention. Nucleic acid includes DNA and RNA. In a preferred aspect, the present invention provides a nucleic acid which codes for a CDR or VH or VL domain of the invention as defined above.

The present invention also provides constructs in the form of plasmids, vectors, transcription or expression cassettes which comprise at least one polynucleotide as above.

The present invention also provides a recombinant host cell which comprises one or more constructs as above. A nucleic acid encoding any CDR, VH or VL domain, or specific binding member as provided itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression a VH or VL domain, or specific binding member may be isolated and/or purified using any suitable technique, then used as appropriate.

Specific binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NS0 mouse melanoma cells, YB2/0 rat myeloma cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of a specific binding member, see for recent reviews, for example Ref, M.E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992.

The disclosures of Sambrook et al. and Ausubel et al. are incorporated herein by reference.

Thus, a further aspect of the present invention provides a ghost cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

Aspects and embodiments of the present invention will now be illustrated by way of example with reference to the following experimentation.

Materials and Methods

Reagents

Two phage display libraries were used: one generated by Marks (Marks et al, 1991) and one obtained from Cambridge Antibody Technology (CaT; Vaughan et al, 1996). Both V gene libraries were of non-immune origin and have been previously described. A calmodulin-binding peptide which we refer to as N9A (described by Montiagiani et al, 1996) was synthesized. N9A-conjugated BSA was prepared by the method of Bernatowicz and Matsueda (1986): the BSA-N9A was dialysed into 100 mM NaCl, 50 mM Na-Borate at pH 8.3 and stored at −20° C., at 19 mg/ml (BCA assay; Perbio, Chester, UK). N9A-conjugated peroxidase (HRP) was prepared by mixing N9A peptide with polymerised, maleimide-activated peroxidase (Sigma: P-1834) dissolved in PBS, pH 7.4. Then 1 mg peroxidase was added to 4.5 nmoles peptide and allowed to react overnight at 4° C. The remaining maleimide groups were blocked with 2-mercaptoethanol. The HRP—N9A was then separated by desalting column, eluting in PBS, pH 7.4. To this was added NDSB-201 (0.5 M final; Calbiochem-Novabiochem; Nottingham, UK:) and thimerosal (0.02% final; Sigma). The mixture was then stored at −20° C.

The recombinant ectodomains of hGPVI comprised residues Q1-T185 of the mature protein (referred to as hD1D2). Two fusion proteins were generated which contained hD1D2, one "hD1D2-His" comprising a his-tag, and the other "hD1D2-CaM" comprising a calmodulin tag. A similar protein, containing the recombinant ectodomains of murine GPVI (comprising residues Q1-L185; termed mD1D2-CaM) was generated. Also, the two domains of hD1D2 were expressed as separate fusion proteins. hD1-CaM comprised residues 1-89, whereas hD2-CaM comprised residues 87-185 of mature hGPVI. Each of these proteins was expressed and purified to homogeneity.

scFv—Selection, Isolation and Expression

Two methods of phage antibody selection were used. Both methods were designed by the inventors: phage antibody was not eluted from the complex but the CaM-antigen-phage antibody complex was removed from the solid phase by chelation of free calcium ions. Phages were selected on recombinant fusion protein hD1D2-CaM.

Antibody Phage Selection—Binding in Solution then Capture

The first method involved mixing recombinant antigen (hD1D2-CaM) with phage (from the Marks library) in free solution, allowing phage antibodies to bind antigen then retrieving this complex by $Ca^{2+}$-dependent attachment to immobilised BSA-N9A. Non binding phages were removed by washing in the presence of $Ca^{2+}$ ions, then phage-hD1D2-CaM complexes were eluted with EDTA. Eluted phages were expanded by transforming bacteria. Three rounds of phage selection were performed before bacterial colonies were screened for scFvs with GPVI binding capacity.

The method in more detail: Phage were prepared from the two non-immune libraries as previously described (Marks et al, 1991) and resuspended in Tris-buffered saline (TBS; 150 mM NaCl, 50 mM Tris-HCl, pH 7.4; TBS) to a final concentration of approximately $10^{12}$ pfu/ml. An immunotube (Nunc) was coated with BSA-N9A at 5 µg/ml (in 50 mM Na-Borate, pH 8.3) overnight at 4° C. and blocked with 2% non-fat milk powder in TBS for 1 h at 37° C. Then 500 µl of phage was added to 3.5 ml of TBS with 0.1% Tween-20 and 1 mM $CaCl_2$ (TBS-TCa) containing 0.5 µg/ml hD1D2-CaM and 3% BSA. The mixture was incubated for 1 h before being transferred to the immunotube. The tube was then incubated for 1 h at room temperature (RT) with rotation to ensure complete capture of hD1D2-CaM by the immobilised BSA-N9A. The immunotube was then washed 10 times with TBS-TCa, followed by 10 times in TBS-Ca (without Tween). The hD1D2-CaM and any specifically bound phage was released from BSA-N9A by washing the immunotube twice with T13S and 10 mM EDTA with 200 µl and then 800 µl for 10 minutes. These washes were pooled and phage recovered by infection of *E. Coli* strain TG1. From the Marks library, three successive rounds of selection were performed by the above method, giving rise to M3B clones: Marks/$3^{rd}$ round/Method B. This gave rise to scFvs described as 1C3, 8A1, 16E12 and 4H9 among other scFvs.

Antibody Phage Selection—Competition with Ligand then Capture

The second method of phage selection involved two rounds. The Vaughan library was used. The first round was performed by method B above using the approach of elution. The resultant selection was termed C1B: CaT/$1^{st}$ round/Method B. For the second round propagated phages from round 1 were incubated with hD1D2-CaM already bound to CRP. Any phages with the ability of displacing hD1D2 from CRP would thus form a soluble complex which was retrieved by capture of hD1D2-CaM on the solid phase by BSA-N9A. These captured antigen-phages were eluted by chelation of calcium and bacteria transformed followed by clone screening for GPVI binding scFvs. Here only two rounds of phage selection were performed: one positive selection on antigen and the second based on displacement of receptor from its ligand.

The method in more detail: An immunotube was coated with BSA-N9A and blocked as before. Parallel, 96-well plates (Immulon 2, Dynex Technologies, Ashford, Middlesex, UK) were coated with 100 µl of CRP at. 10 µg/ml in 0.01 M acetic acid overnight at 4° C. All subsequent steps were performed at RT. Plates were blocked by incubation with 200 µl of blocking buffer (TBS and 5% BSA, pH 7.4) for at least 30 min. The wells were washed three times with 200 µl of adhesion buffer (TBS and 0.1% BSA). Then 100 µl of hD1D2-CaM (at 20 µg/ml) was added to each well and incubated for 2 h. The wells were washed four times with 200 µl of adhesion buffer to remove unbound hD1D2-CaM. Then 100 µl of C1B phage was added to the wells and incubated for 2 h. The contents of these wells were added to the immunotube containing immobilised BSA-N9A and incubated for 30 min to capture any hD1D2-CaM eluted from CRP by the phage. The immunotube was then washed by filling 20 times with adhesion buffer and the hD1D2-CaM released by TBS with 10 mM EDTA as before. Phage were recovered by infection of *E. Coli* strain TG1. This competitive method of selection was termed Method C. This was used as the second round for C1B, the resulting selection was termed C1B2C. This gave rise to clones 10B12, 4D5, 21C7-1 and 21C7-2. This method was successful in isolating a scFv able to inhibit various physiological platelet responses to collagen, as discussed further below.

Rescue of Phagemid Antibodies after Selection

After each round of selection, the eluted phage were added to 10 ml of *E. Coli* strain TG1, grown in 2TY to mid-log phase growth ($A_{600nm}$=0.5-0.8). These were incubated for 30 minutes at 37° C., without shaking. The culture was then centrifuged at 1000 g for 10 minutes and the supernatant discarded. The pellet containing the infected TG1 was resuspended in the remaining fluid, plated out onto TYAG plates and grown overnight at 37° C. If a further round of selection was to be performed, the plates were scraped and all the colonies mixed together in 10 ml 2TY. 100 µl of this mixture was used to innoculate 25 ml 2TY with 100 µg/ml ampicillin and 1% glucose (2TYAG) and the culture grown to mid-log phase. Helper phage (VSCM13) were then added to a final concentration of $5 \times 10^9$/ml and the culture incubated for 30 minutes at 37° C. The culture was then centrifuged at 1000 g for 10 minutes and the supernatant discarded. The pellet was resuspended in 25 ml prewarmed 2TY+100 µg/ml ampicillin and 50 µg/ml kanamycin (2TYAK) and incubated overnight at 30° C. with shaking. The culture was then centrifuged, using two consecutive spins in fresh tubes, at 10,800 g for 15 minutes per spin. The supernatant (containing the rescued phage) was mixed with 0.3 volumes of 2.5M NaCl, 20% glycerol and incubated on ice for 1 hour. The mixture was again spun with two consecutive spins in the same tube at 10,800 g for 15 minutes per spin. The supernatant was completely removed and the pellet resuspended in 2 ml TBS. This was spun at 11,500 g for 10 minutes to remove any traces of remaining bacteria. The supernatant, representing the purified, rescued phage was decanted and stored at 4° C. until required.

Isolation of TG1 Clones and Expression of scFv Antibodies from Phagemid Clones

For the final round of selection, colonies were picked from TYAG plates into 96-well plates containing 100 µl of 2TYAG per well. The plates were incubated with shaking, overnight at 37° C. 100 µl per well of 20% glycerol in 2TYA was then added and the plates stored at −70° C. At a later date, plates containing 100 µl 2TYAG were inoculated by 96-well transfer device from these frozen glycerol stocks. The clones were grown overnight then used to inoculate another set of plates containing 200 µl induction medium (2TY with 100 µg/ml ampicillin and 0.1% glucose). After growing the clones for 6 h at 37° C., 25 µl of 9 mM isopropyl β-D-thiogalactoside (IPTG) was added into each well and the clones grown overnight at 30° C. to induce soluble scFv expression. The plates were centrifuged at 1000 g for 40 min to obtain a clear supernatant, used in the ELISA screening assays.

The clones were screened (as bacterial culture supernatants) by capture ELISA to detect scFvs recognising hD1D2-CaM. Clones identified reacting positively in this initial screening were then used to inoculate new plates containing 100 µl per well of growth medium and were grown. A sample was subjected to PCR screening and digestion with BstN1 enzyme. Where colonies from the same positive clone had different digestion patterns, both phagemid preparations were DNA sequenced. Where both colonies gave the same digestion pattern, one was selected as representative.

Induction of cultures from phagemid clones was also performed to obtain larger volumes (10 ml) for further testing, as described herein.

Screening for Positive Clones Against GPVI
PCR Screening and DNA Fingerprinting of Clones Phagemid clones were screened for the presence of a scFv insert of the correct size by PCR amplification using primers LMB3 (CAG GAA ACA GCT ATG AC—SEQ ID NO. 23) and fd-seq1 (GAA TTT TCT GTA TGA GG—SEQ ID NO. 24), the size of the amplicon being analysed by agarose gel electrophoresis. A further portion of each product from the above reaction was digested with BstN1 enzyme (Marks et al, 1991) and restriction fragment length polymorphism patterns analysed by agarose gel electrophoresis.

Capture ELISA to Detect scFv Recognising hD1D2-CaM

For the capture ELISA, 96-well plates (Maxisorp, Nunc) were coated overnight at 4° C. with 50 μl BSA-N9A at 5 μg/ml in 50 mM Na-Borate (pH 8.3). The wells were washed, blocked by incubation for 30 min at 37° C. and washed twice again with 200 μl TBS-TCa. hD1D2-CaM in TBS-TCa at 5 μg/ml (in 50 μl) was incubated for 30 min at RT. After washing the wells four times with 200 μl TBS-TCa, 100 μl of the bacterial supernatant was incubated for 2 h at RT. After washing for four times, 100 μl HRP-labelled 9E10 monoclonal antibody at 0.2 μg/ml (Roche, Lewes, UK) was incubated for 30 min at RT. After washing the wells six times, 100 μl of KPL 1-component substrate (Dynex Technologies, Middlesex UK) was added. After 20 min the reaction was terminated with 50 μl of 0.5 M $H_2SO_4$. The absorbances were read at 450 nm with no plate blank.

Direct ELISA to Detect scFv Recognising hD1D2-CaM and other Antigens

For the direct ELISA, 96-well plates (Maxisorp, Nunc) were coated overnight at 4° C. with 50 μl streptavidin, mouse IgG, lactoferrin, thyroglobulin, lysozyme, bovine type 1 collagen, hD1D2-CaM or the individual domains of GPVI (D1-CAM and D2-CAM) with 50 μl per well at 5 μg/ml in 50 mM Na-Borate (pH 8.3). The wells were washed once with 200 μl TBS-TCa, then blocked by incubation with 200 μl TBS-TCa for 30 minutes at 37° C. and washed twice again with 200 μl TBS-TCa. Hundred μl of induced bacterial culture supernatant was then incubated in the wells for 2 hrs at RT. After washing the wells four times with 200 μl TBS-TCa, 100 μl of the bacterial supernatant was incubated for 2 hrs at RT. After washing for four times, 100 μl HRP-labelled 9E10 monoclonal antibody at 0.2 μg/ml was incubated for 30 min at RT. After washing the wells six times, 100 μl of KPL 1-component substrate was added. After approximately 20 min the reaction was terminated with 50 μl of 0.5 M $H_2SO_4$. The absorbances were read at 450 nm with no plate blank.

Red Cell Agglutination

Papainised $R_1{}^wR_1$ red cells (Reagents Laboratory, National Blood Service, East Anglia centre) were diluted to 0.8% in Cell Stab buffer (DiaMed, Cressier sur Morat, Switzerland). Into the upper reservoir of a NaCl Gelcard (Diamed; La pierre et al (1990)), 50 μl cell suspension was placed. Firstly, 50 μl purified scFv (at either 1 or 10 μg/ml, diluted in Cell Stab buffer) was added to 50 μl of 9E10 monoclonal antibody culture supernatant (60 μg/ml) to promote cross-linking of scFvs. Then 50 μl of the mixture was carefully mixed with the cells in the gelcard and incubated for 15 minutes at RT. The cards were then centrifuged according to the manufacturer's instructions and any agglutination of cells was recorded. Later on, the purified scFvs were tested against two different panel red cells, i.e. R1R1 and R2R2.

Purification and Expression of Positive Clones

Subcloning of the scFvs into pUC and Purification

The scFv cassettes of positive clones with promising characteristics and distinct V gene sequences were subcloned into the vector pUC119-Sfi/Not-His6 (as described in Griffiths et al (1994), except that an Sfi I site was present in place of the Xba I site) using *E. Coli* strain TG1 as host. After recloning the V genes were sequenced to verify the nucleotide sequences.

Small Scale Expression of scFvs in Bacterial Culture Supernatant

A distinct circular colony was used to innoculate 3 ml growth medium (2TY and 100 μg/ml ampicillin and 1% glucose). This was grown overnight, with shaking at 37° C. before being diluted approximately 1/100 in 10 ml induction medium (2TY and 100 μg/ml ampicillin and 0.1% glucose). These cultures were maintained at 37° C., with shaking until an OD 600 nm=0.5-0.8 was achieved. IPTG was then added to a final concentration of 1 mM. The cultures were maintained at 30° C. overnight, with shaking, and then centrifuged at 1000 g for 30 min to obtain a clear supernatant. This was apsirated, filtered (0.2 μm) into a fresh tube and stored at 4° C.

Large Scale Expression and Purification of scFvs

A distinct circular colony was used to innoculate 50 ml growth medium (2TY and 100 μg/ml ampicillin and 1% glucose). This was grown overnight, with shaking at 37° C. before being diluted approximately 1/200 in induction medium (2TY and 100 μg/ml ampicillin and 0.1% glucose; several volumes of 500 ml in 2 l flasks). These cultures were maintained at 30° C., with shaking for 4 h. IPTG was then added to a final concentration of 1 mM. The cultures were maintained at 30° C. overnight, with shaking, and then centrifuged at 4000 g for 10 min to obtain a bacterial pellet. This pellet was then resuspended in ice-cold periplasmic buffer containing 20% sucrose, 30 mM Tris-HCl and 1 mM EDTA, pH 7.5 and incubated on ice for a minimum of 20 min. The mixture was centrifuged again at 6000 g for 10 min and the supernatant (called the "periplasmic extract") retained. The pellet was resuspended in ice-cold 5 mM $MgSO_4$ and incubated on ice for a minimum of 20 min. The mixture was then centrifuged, along with the periplasmic extract at 18,500 g for 60 min. The supernatant was then dialysed extensively versus 0.5 M NaCl, 50 mM Sodium phosphate, pH 7.5 (IMAC buffer), at 4° C. Imidazole was then added to 25 mM and the dialysate was filtered (Stericup 0.2 μm filter, Millipore). A HiTrap Chelating column (Amersham Pharmacia Biotech, Amersham, UK) was then charged with $Ni^{2+}$ ions according to the manufacturer's instructions. This column was equilibrated with 4-6 column volumes of IMAC buffer containing 100 mM Imidazole at pH 7.5 (equilibration buffer). The filtered dialysate from above was then passed through the column and the column was then washed with 6-10 column volumes of equilibration buffer. The scFvs were eluted from the column by passing through elution buffer containing 250 mM imidazole in IMAC, pH 7.5.

This eluate, which contained highly purified scFv, was then desalted into 150 mM NaCl, 10 mM HEPES, pH 7.2 (HBS) either by dialysis or by gel filtration chromatography. Dialysis was performed on essentially pure scFv. Gel filtration chromatography was performed as described below, except that the peaks representing both dimeric and monomeric scFv were pooled together. In this way, no bias from the inherent oligomerisation state of the scFv was introduced and scFv prepared by dialysis and gel filtration could be compared directly. For all assays in which purified scFvs were used, including epitope mapping studies by biosensor, the scFvs were prepared in this way.

The purity of scFv was monitored at each stage by subjecting samples to reducing SDS-PAGE on a 3%/15% discontinuous gel in a Mini Protean system (BioRad, Hemel Hempstead, UK) according to the method of Hames (1990). Protein quantitation was made by BCA assay kit (Perbio, Chester, UK) with reference to a standard curve of 0.0625-2 mg/ml BSA.

Purification of Monomeric scFv

For biosensor studies to determine the affinity of scFvs for hD1D2, certain fractions containing purified scfv were pooled and concentrated using Centricon 10 concentrators (Amicon, Beverley. MA) then subjected to gel filtration using a Superose 12 column attached to an AKTA purifier 10 (AP-Biotech, Amersham, UK) with 150 mM NaCl, 10 mM HEPES, pH 7.2 (HBS) as eluant. Gel filtration was performed to remove the dimeric portion of scFv and any additional contaminants.

The scFv separated into two peaks; a small peak eluting before a much larger peak. Under identical conditions, the elution volumes for the peaks were compared against the migration of standards (Combithek, Boehringer Mannheim). The elution volume for the smaller, early peak was 13.2 ml (around the size expected for a scFv dimer of 58 kDa), just after the elution volume for albumin (68 kDa, 12.9 ml). The elution volume for latter, larger peak was 14.8, close to the elution volume for chymotrypsin (25 kDa, 15.2 ml). For affinity measurements on the biosensor only protein eluting in the latter peak (monomeric scFv) was used. No contaminating proteins were observed in this sample, when applied to SDS-PAGE.

DNA Sequencing

Purified double-stranded phagemid DNA was used as template for sequencing within the BigDye Terminator Cycle Sequencing Ready Reaction kit according to the manufacturers instructions (PE/Applied Biosystems, Warrington, UK). The primers LMB3 (SEQ ID NO. 23) and pHEN-SEQ (CTA TGC GGC CCC ATT CA —SEQ ID NO. 25) were used, while the analysis was run with the Applied Biosystems 373 DNA sequencer. The nucleotide sequences of the clones were analysed with MacVector 6.5.3 (Oxford Molecular Group) and compared for homology with germline V-gene sequences in the online Vbase directory, the DNAPLOT (Sequence alignment software in the V Base database, http://www.mrc-cpe.cam.ac.uk; Cook and Tomlinson, 1995). The VH and VL genes were aligned to their most homologous germline genes and the mutation rates (number of replacements) were calculated. For calculations, the 18 nucleic acids of both genes in the 5'-end were not considered (imprinted by the primers). For the VH gene, also the last 6 nucleotides were not considered in the analysis, because of being contained in the DJ and VH gene recombination and 'N' additions region. Amino acid annotation was according to Kabat (Kabat et al, 1991).

Flow Cytometry

The purified scFvs were tested for reactivity with platelets with the immunofluorescence test. Platelet rich plasma (PRP) was freshly prepared from EDTA-anticoagulated blood by centrifugation at 1400 rpm for 10 min, and PRP corresponding to $5\times10^5$ platelets (counted by Sysmex K1000 Milton Keynes, UK) was transferred into a 96-well plate (Dynex, Microtiter). The platelets were washed twice in buffer (PBS with 10 mM EDTA of pH 6.8 and 0.25% BSA) by centrifugation at 3000 g for 6 min. The platelets were resuspended in 150 µl purified scFv at 100 µg/ml and incubated for 1 h at RT. After washing with 200 µl buffer, the platelets were resuspended in 100 µl 9E10 Mab (at 30 µg/ml) and incubated for 1 h at RT. The platelets were then washed once, resuspended in 50 µl of a 1:20 dilution of fluorescein isothiocyanate (FITC)-conjugated goat anti-mouse IgG (Dako, Cambridge, Uk) and incubated for 30 min at RT in the dark. After a final wash, platelets were resuspended in 200 µl buffer and the fluorescence intensities of 10,000 events were analysed using a flow cytometer (Coulter XL, Luton UK). The median fluorescence intensity was recorded on a logarithmic scale.

When studying saturation of platelets with the purified scFvs, platelets were freshly prepared from EDTA-anticoagulated whole-blood by washing twice in buffer. Then 50 µl of platelets $10^7$/ml (corresponding to $5\times10^5$ platelets) was dispensed into the wells of a 96-well plate. The platelets were washed twice and resuspended with 150 µl purified scFv at varying concentrations (from 0.01 to 500 µg/ml) for 1 h at RT. When studying the expression levels of GPVI on platelets in different individuals scFv 1C3 was used at 10 µg/ml concentration. Platelets were isolated from fresh blood samples except in two cases platelets were recovered from cryopreserved stocks. In one of these two donors GPVI was encoded by the "wild type" GPVI allele whilst in the other, one of the alleles carried a low frequency single nucleotide polymorphism replacing the L at position 83 by a V.

The inhibition of scFv binding to platelets by soluble D1D2 was studied by flow cytometry. The purified scFv 1C3 or 10B12 at the concentration 20 µg/ml was incubated with D1D2-His at different concentrations (from 1 to 300 µg/ml) in total volume of 150 µl for 15 min at RT. Then 50 µl of platelets $10^7$/ml (corresponding to $5\times10^5$ platelets) freshly prepared from EDTA anticoagulated whole blood, by washing twice in buffer, was dispensed into the wells of a 96-well plate containing 150 µl of the scFv-hD1D2 mixture, and incubated for 1 h at RT. The protocol was then completed as described above.

Ligand Binding Assay: the scFv Inhibiting the Interaction of hD1D2-CaM with Collagen Related Peptide (CRP)

Any effects of scFvs on the interaction of hD1D2-CaM with CRP (GCO(GPO)$_{10}$GCOG, single letter amino acid code where O is hydroxyproline—SEQ ID NO. 21) or GPP10 (GCP(GPP)$_{10}$GCPG—SEQ ID NO. 22) were tested using the following assay. 96-well plates (Immulon 2, Dynex Technologies, Ashford, Middlesex, UK) were coated with 100 µl of CRP at 10 µg/ml in 0.01 M acetic acid for 1 h at 20° C. or 4° C. overnight. All subsequent steps were performed at 20° C. The wells coated with CRP were blocked by incubation with 200 µl of blocking buffer (TBS containing 5% BSA, pH 7.4) for 30 min. Then the wells were washed three times with 200 µl of adhesion buffer (TBS and 0.1% BSA, pH 7.4). Meanwhile 20 µl of hD1D2-CaM at 5 or 12.5 µg/ml (0.1 or 0.25 µg total) was preincubated with 180 µl bacterial supernatant (containing scFvs) or the purified scFv over a wide range of concentrations and added to each well. After incubation for 2 h, the wells were washed three times with 200 µl of adhesion buffer to remove unbound hD1D2-CaM. The wells were incubated with 100 µl HRP—N9A at (0.16 µg/ml) in adhesion buffer for 30 min. After washing the wells five times with 200 µl of adhesion buffer, 100 µl of substrate was added. The reaction was terminated after several minutes and the absorbance measured, using no plate blank. The mean absolute absorbance value from wells where hD1D2-CaM/scFv was replaced by adhesion buffer was regarded as "background" and was subtracted from all other values. This was typically 0.05-0.06. The mean absorbance value for hD1D2-CaM binding to CRP (in the absence of scFvs) was then set to 100% and referred to as "uninhibited binding" (mean absolute absorbance values are shown in each legend). The values for binding in the presence of scFvs were expressed as a percentage of this. In each assay, the binding of hD1D2-CaM to the control peptide GPP10 was indistinguishable from background, indicating that CRP was being specifically recognised by hD1D2-CaM.

Biosensor: Epitope Mapping and Affinity Measurement

Binding studies and affinity measurements were conducted using a resonant mirror biosensor (Iasys, Thermolabsystems, Cambridge, UK). Using this system, one protein (the ligand)

was immobilised to the mirrored surface of the cell of a cuvette. The cell contains a stirred volume of buffer to which aliquots of a second protein (the ligate) are then added. If the ligate binds or dissociates from the immobilised ligand, these changes are detected optically and give a reading in arc.sec−1 in real time. A linear relationship has been found to exist between the mass of the protein and the arc.sec−1 response observed (De Merwe 1993). Here, BSA-N9A was covalently immobilised to a carboxymethyldextran surface using the manufacturer's instructions. The machine was then primed with TBS-TCa. A stirring speed of 100, cuvette temperature of 25° C. and reaction volume per cell of 50 μl were used in all experiments unless otherwise indicated. At the start of an experiment, a recombinant CaM-containing fusion protein (e.g. hD1D2-CaM) was added to a cell, resulting in its non-covalent, $Ca^{2+}$-dependent immobilisation to N9A. Several washes with TBS-TCa were made to remove unbound material from the cell. Then typically the wells were filled with 45 μl buffer to which was added further volumes of purified scFv (e.g. 5 μl) in HBS. The binding of scFv was measured in arc.sec$^{-1}$. The binding curves were analysed either by recording response at equilibrium versus time (for epitope mapping studies) or by calculating the initial rates of binding at different scFv concentrations using FastFit software (for affinity measurements).

Aggregometry

Platelet-rich plasma (PRP) was obtained from fresh citrated whole blood of healthy donors by centrifuging at 190 g for 12 minutes. Platelet-poor plasma (PPP) was prepared from PRP by centrifuging at 3000 g for 10 minutes. To determine platelet aggregation, light transmission in PRP (250 μl) was measured and recorded on a Chrono-Log 490-4D four channel aggregometer (Labmedics Ltd, Stockport, Cheshire, UK) at 37° C. over 15 min and was expressed as arbitrary units with 100% transmission adjusted with platelet poor plasma. Platelets were incubated for 5 minutes with purified scFv with no effect before aggregation was induced by addition of agonist. Agonists were Fibrillar collagen type 1 (Ethicon Corp, 1 μg/ml; 2.5 μl of 100 μg/ml in 250 μl of PRP), adenosine diphosphate (ADP; 30 μM) or U46619 (2 μM). The scFvs were studied at different concentrations (10 to 50 μg/ml).

Reactivity of the scFvs with Granulocytes and Lymphocytes by Immunofluorescence Assay The purified scFvs were tested for reactivity with granulocytes and lymphocytes using lysed whole blood in a flow cytometric assay. Briefly, an aliquot of whole EDTA anticoagulated blood containing $0.5 \times 10^6$ leukocytes (counted by Sysmex K1000, Milton Keynes, UK) was added to a 75×12 mm tube. The red cells were lysed by the addition of an ammonium chloride solution. The remaining leukocytes were washed twice and 150 μl of scFv added at a concentration of 50 μg/ml. After incubation for 1 h at RT, the cells were washed and incubated with 9E10 mAb for 1 h at RT. After washing, FITC-conjugated anti-mouse Ig (Dako, Cambridge, UK) was added and incubated for 30 min. The cells were washed once and subsequently analysed by flow cytometry. The median fluorescence intensity was recorded on a logarithmic scale.

Platelet Adhesion Assay: the scFv Inhibiting the Interaction of Platelets with Collagen and Related Molecules In order to test the effects of scFvs on the interaction of platelets with collagen and related molecules the following assay was performed. Immulon 2 96-well plates were coated for 1 h at 20° C. or overnight at 4° C. with 100 μl per well of fibrillar type I collagen, monomeric type I collagen, GFOGER-GPP or CRP at 10 μg/ml in 0.01 M acetic acid. PRP was prepared from fresh whole blood after spinning for 12 min at 200 g. 10% (v/v) and ACD buffer (39 mM citric acid, 75 mM tri-sodium citrate.$2H_2O$, 135 mM D-glucose, pH 4.5) and prostaglandin $E_1$ ($PGE_1$; 0.28 μM final concentration) were added and the PRP was spun for 10 min at 700 g. The platelet pellet was resuspended in 5 ml of buffer (5.5 mM D-glucose, 128 mM NaCl, 4.26 mM $Na_2HPO_4.2H_2O$, 7.46 mM $NaH_2PO_4.2H_2O$, 4.77 mM tri-sodium citrate.$2H_2O$, 2.35 mM citric acid, 0.35% w/v BSA, pH 6.5). $PGE_1$ was added as before and the platelets were spun for 10 min at 700 g. Platelets were resuspended to $10^8$ platelets/ml in adhesion buffer (50 mM Tris, 140 mM NaCl, 0.1% w/v BSA, pH 7.4), treated with 2 mM magnesium chloride and purified scFvs and allowed to rest for 15 min at room temperature.

Ligand-coated wells were blocked by incubation with 200 μl of blocking buffer (50 mM Tris, 140 mM NaCl, 5% w/v BSA, pH 7.4) for 30 min. The wells were washed three times with 200 μl of adhesion buffer, then 50 μl of platelet suspension ($10^7$ platelets in total) was added to each well and left for 1 h at 20° C. The wells were emptied and washed three times with 200 μl of adhesion buffer to remove non-adherent platelets. Adherent platelets were lysed by incubation for 1 h with 150 μl per well of lysis buffer (0.07 M tri-sodium citrate, 0.3 M citric acid, 0.1% v/v Triton X-100, 5 mM p-nitrophenyl phosphate). The reaction was terminated by the addition of 100 μl of 2 M NaOH to each well. Adhesion was measured calorimetrically as the absorbance of the p-nitrophenol product at 405 nm in a Maxline Emax microplate reader (Molecular Devices Ltd., Crawley, UK). Values were corrected for background by subtraction of readings from BSA-coated wells. In agreement with others, the relationship between platelet number and $A_{405}$ is linear up to 3.0 absorbance units and in a typical experiment, adhesion to CRP results in $A_{405}$~1.2±0.4, which corresponds to adhesion of ~25% of the cells applied.

Perfusion Chamber Studies: Platelet Adhesion and Aggregation on Collagen Surface Blood was collected from specific HLA-A2 positive and negative donors at the Bloedbank, NZW, Utrecht, The Netherlands. The blood was anticoagulated with 20 U/ml (final) of low molecular weight heparin (Fragmin, Pharmacia, Stockholm) and used within 8 hours of collection.

Thermanox™ coverslips (Nunc, Naperville Ill.) were soaked overnight with 80% ethanol, rinsed thoroughly with distilled water and air-dried. Human placental collagen type III (Sigma) was solubilised in 0.05M acetic acid and sprayed onto coverslips.

For perfusion studies, the blood was drawn through a mini chamber as described by Sixma et al., 1998. The tube containing the blood sample and the mini-chamber device were at 37° C. The blood was preincubated for 10 minutes with each scFv (at 50 μg/ml final) before the start of each perfusion. As the blood is drawn into this chamber, it enters a slit 0.1 mm deep and 2 mm wide. A coverslip has been clamped in place so that this represents the upper surface of the slit. Blood was drawn through at a constant rate using a Harvard infusion pump (pump 22, model 2400-004, Harvard, Natick, Mass.), corresponding to a shear rate of 1600 s$^{-1}$ at the surface of the coverslip. The perfusion time was 5 minutes. This was followed by prewarmed HBS (containing the relevant scFv at 10 μg/ml), to rinse the coverslips. Each perfusion was carried out in triplicate, using 3 minichambers connected to one volume of blood.

After each perfusion, the coverslips were removed from the minichambers, rinsed with HBS, then fixed in 0.5% glutaraldehayde in PBS, dehydrated in methanol and stained with May-Grünwald/Giemsa as previously described.

Platelet adhesion was quantified using a light microscope (Leitz Diaplan) under high power (400× magnification) fitted with a CCD camera and attached to a computer equipped with Optimas 6.0 image analysis software. A minimum of 20 distinct fields per coverslip were sampled to calculate a mean surface coverage which was expressed as a percentage of the total surface area sampled. Three separate coverslips treated with the same blood sample were analysed in this way, and an overall mean+SD was thus derived for each scFv treatment on each donor blood sample.

Advanced Perfusion Studies: Platelet Adhesion, Thrombus Formation and Procoagulant Expression on Collagen Surface Measured in Real Time Materials used for this particular study were Fibrillar type-I collagen. (Horm) from equine tendon was purchased from Nycomed (Munich, Germany). High molecular weight heparin was from Sigma (St. Louis, Mo., USA) and H-Phe-Pro-Arg chloromethyl ketone (PPACK) was from Calbiochem (La Jolla, Calif., USA).

Annexin V (Apoptest) labelled with Oregon Green 488 (OG488) was obtained from Molecular Probes (Eugene, Oreg., USA).

Blood from healthy laboratory personnel was collected in 40 μM PPACK in 1/10 volume of PBS, supplemented hourly with 10 μM PPACK. Subjects had not taken medication during the previous two weeks. Platelet counts were determined with a Coulter counter (Coulter Electronics, Hialeah, Fla., USA).

Whole blood perfusion experiments were performed essentially as described for mouse blood (Nieswandt et al 2001, EMBO J. (2001) 20, 2120-30). Briefly, glass coverslips (24×60 mm) were coated with collagen fibres (12.5 μg/cm$^2$) and blocked with Hepes buffer containing 1% BSA and 1% glucose. The blood was placed in a syringe and perfused over the coverslip through a transparent 50 μm deep chamber using a pulse-free pump, at a shear rate of 1000 s$^{-1}$ for 4 min (Billy et al. (1997) Blood Coagul Fibrinolysis, 8, 168-174.). Blood was either used untreated or was incubated for 15 min prior to perfusion with various concentrations of scFv 10B12.

Microscopic phase-contrast and/or fluorescent images from fluo-3 were recorded in real-time using a Visitech digital imaging system (Sunderland, UK) equipped with two intensified, CCD cameras (Heemskerk et al. (1997) Blood, 90, 2615-2625.). After perfusion, flow chambers were rinsed with Hepes buffer pH 7.45 supplemented with 1 U/ml heparin and 2 mM CaCl$_2$ at the same flow rate for 4 min. Phase contrast and fluorescent images were collected with a 40×UV-transparent objective and 15-20× image magnification. Exposure of phosphatdyl serine was detected by 5 min post-incubation of the slide with 100 μl of Hepes/CaCl$_2$ buffer containing OG488-labeled Annexin V (1 μg/ml). Antibodies and antagonists were also added to the rinsing buffer and the Annexin V incubation at the original concentrations.

Surface area coverage from phase-contrast images was analysed using Image-Pro software version 4.1 (Silverspring, Md., USA). Area coverage by platelets staining with OG488-annexin V was determined with Quanticell software (Visitech). Distribution of aggregate sizes in phase contrast images was measured using Leica QWin image analysis software (Leica Imaging Systems, Cambridge, UK).

Figure 2:
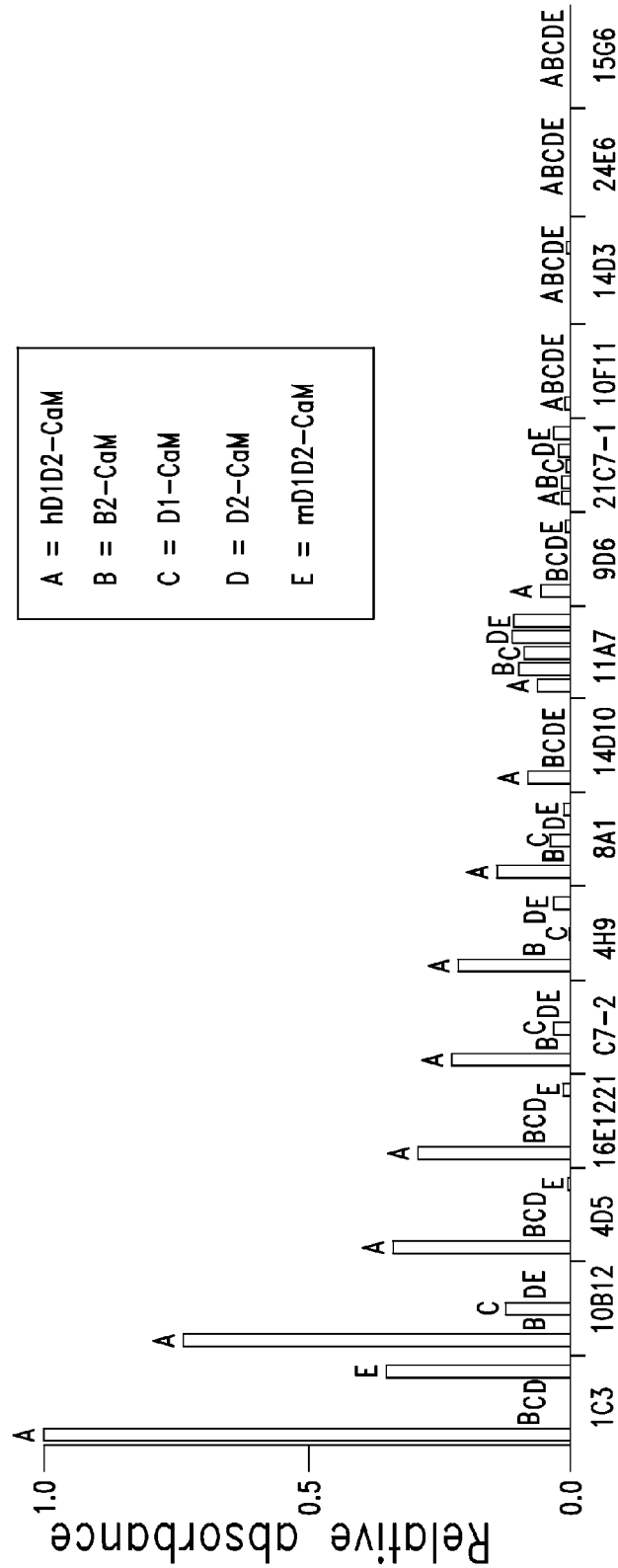

Results
Reactivity of Selected Clones by ELISA scFvs were expressed from the fifteen clones and bacterial supernatants tested against a panel of non-related antigens by ELISA. When tested against a panel of directly coated antigens, seven of the fifteen scFvs were positive on hD1D2 (clones 1C3, 21C7-1, 10B12, 8A1, 4D5, 21C7-2, 9D6), of which four reacted strongly (1C3, 21C7-1, 10B12, 8A1). Four of these (21C7-1, 4D5, 21C7-2, 9D6) showed cross-reactivity with other directly coated antigens (FIG. 1). ScFv 21C7-1 recognised the other CaM-containing protein in this antigen panel; the scFv B2-CaM. Therefore, 21C7-1 may recognise a shared epitope. However, this epitope appears to be lost upon capture by N9A peptide, as it is unreactive against B2-CaM in the capture ELISA (FIG. 2). One of the antigens was polyvalent immunoglobulin G, a preparation derived from the pooled plasma of over 5,000 donors. Two scFvs (10F11 and 14D10) showed a marked reactivity to this antigen preparation. The inventors assume that such interactions were based on idiotype anti-idiotype interactions and that such interactions may not be uncommon for scFvs. The remaining three strong binders showed negligible cross-reactivity.

When BSA-N9A is used to capture antigens to the solid phase in a Ca$^{2+}$-dependent manner, it is assumed that the protein is free to adopt its native conformation, with each surface accessible to solvent. Under these conditions, nine of the scFvs (1C3, 10B12, 4D5, 16E12, 2-1C7-2, 4H9, 8A1, 14D10 and 9D6) recognised hD1D2 specifically, compared to the scFv B2-CaM (FIG. 2). Three scFvs (4D5, 16E12, 4H9) which showed little or no reactivity with directly coated hD1D2 were able, quite strongly, to recognise hD1D2 captured under these conditions.

Presumably the epitopes recognised by these scFvs are strictly conformation-dependent. A further two scFvs, (14D10 and 9D6) also showed specific reactivity under these conditions, but reacted very weakly. Indeed the reactivity of scFv 9D6 was considered so weak that no further studies were performed on it. scFv 1C3 recognised murine D1D2 also, indicating that its epitope is composed of residues which are largely conserved between human and mouse GPVI. ScFv 10B12, on the other hand, was found not to react with murine D1D2, but showed some reactivity towards hD1, expressed as an isolated domain as a CaM-fusion protein.

Figure 7:
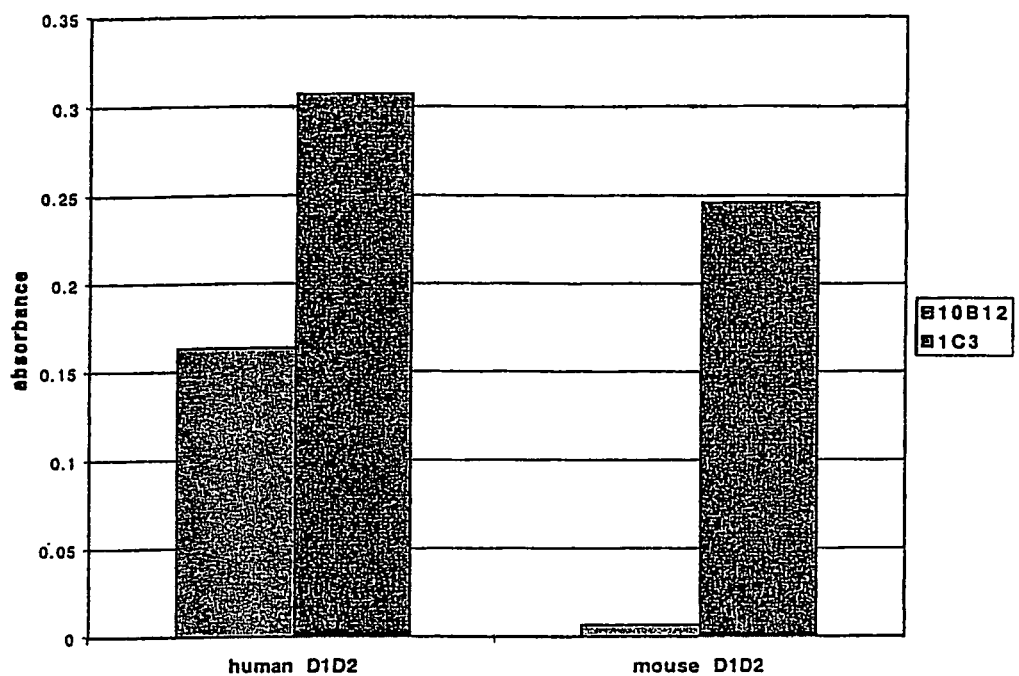
Figure 8:
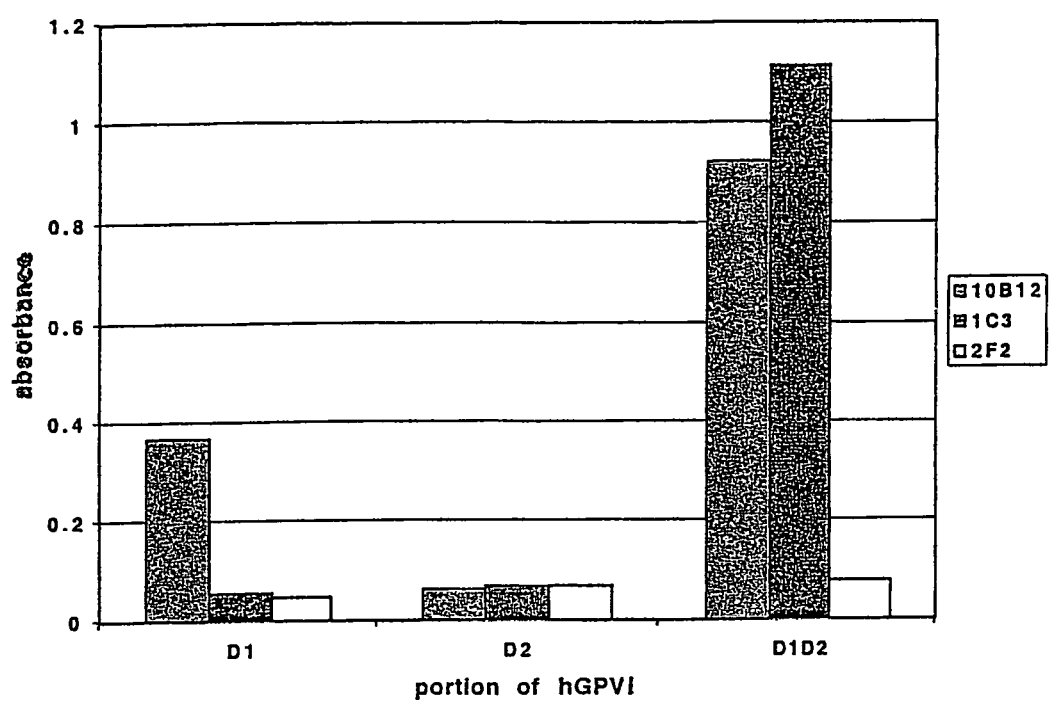

The V gene cassettes of 4 clones (1C3, 10B12, 16E12, 8A1) were re-cloned into pUC-119. ScFv expressed from the pUC vector retained specific binding to hD1D2-CaM in the capture ELISA. The four scFvs did not show any reactivity against other antigens (FIGS. 3-6). The two most strongly reactive scFvs (1C3 and 10B12), were tested, this time as purified scFvs, for their reactivity against hD1D2, murine D1D2 (mD1D2) (FIG. 7) and the separate Ig-like domains of hGPVI (hD1 and hD2) (FIG. 8). These experiments confirmed that scFv 1C3 but not 10B12 binds murine D1D2, while 10B12 weakly binds hD1. These results confirmed those previously obtained with non-purified scFvs expressed in bacterial supernatants of the original phagemid vector (FIG. 2).

Capacity to Inhibit Binding of hD1D2-CaM to CRP

In both adhesive and activation assays platelets show high selectivity, via GPVI, for GPO- over GPP-sequences (Knight et al 1999). hD1D2-CaM binds CRP specifically and does not bind to GPP10 (the control peptide lacking hydroxyproline). hD1D2 is therefore recognising a similar structure to native GPVI. Inhibitors of the interaction of this recombinant protein with CRP are likely to inhibit the recognition of CRP by platelets (via native GPVI) also.

Figure 9:
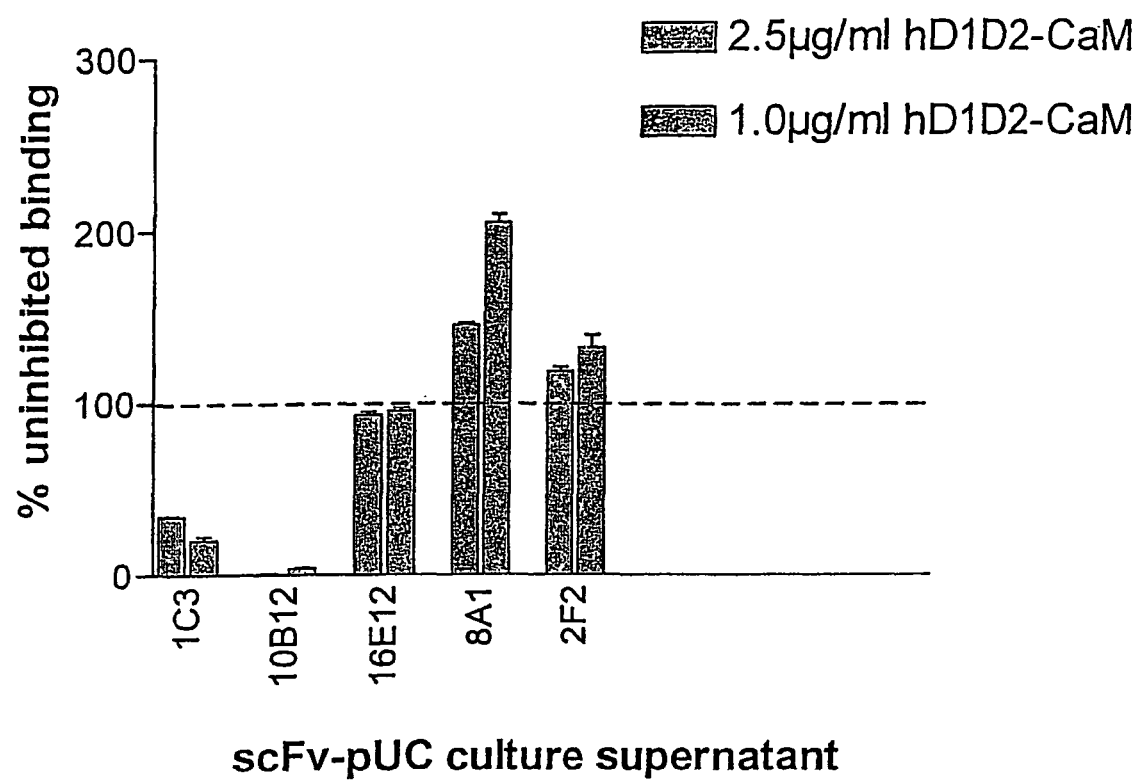

The ability of scFvs to inhibit this binding was tested in two stages: as bacterial supernatants and as purified scFvs. The binding assay was performed as described already above. When bacterial supernatant was used, scFv 10B12 produced effective inhibition of hD1D2 binding to CRP (FIG. 9). In this unpurified form, scFv 1C3 also produced a marked degree of inhibition in this assay, which was reduced by increasing the dose of hD1D2 (i.e. as the ratio of scFv 1C3 to hD1D2 was decreased). ScFv 16E12 was inert in this assay and scFv 8A1 enhanced the interaction, an effect which increased as the hD1D2 concentration was lowered (i.e. the ratio of scFv 8A1 to hD1D2 was increased). The control scFv, 2F2 (recognising another platelet receptor GPIIbIIIa) also showed a mild enhancement of the interaction under these conditions (FIG. 9).

Figure 10:
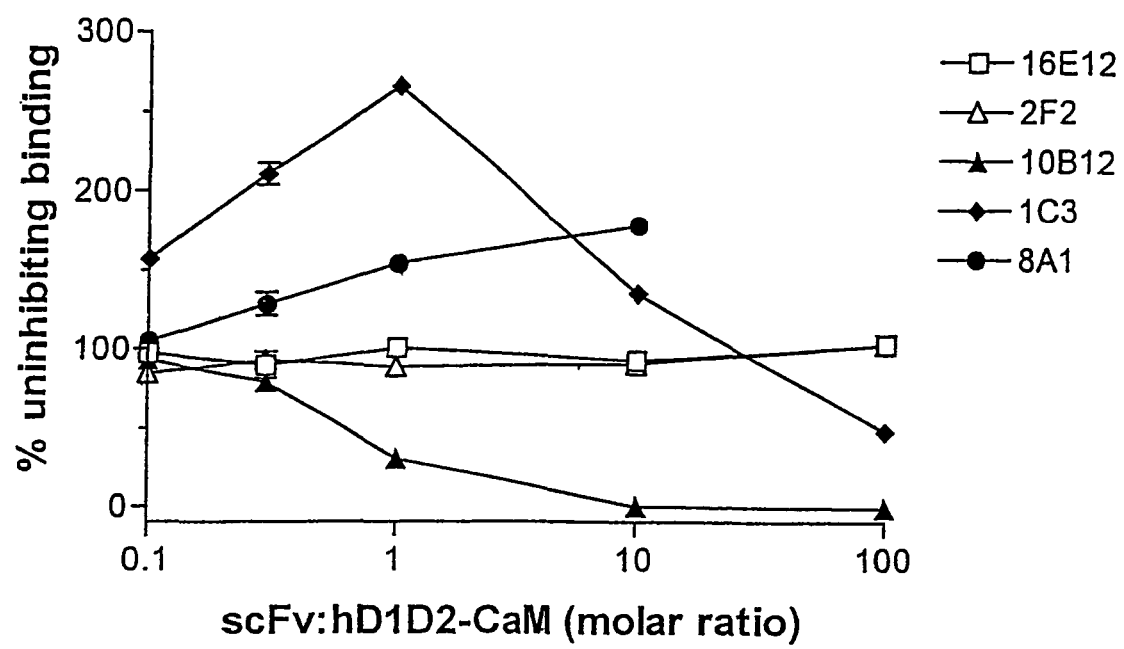
Figure 11:
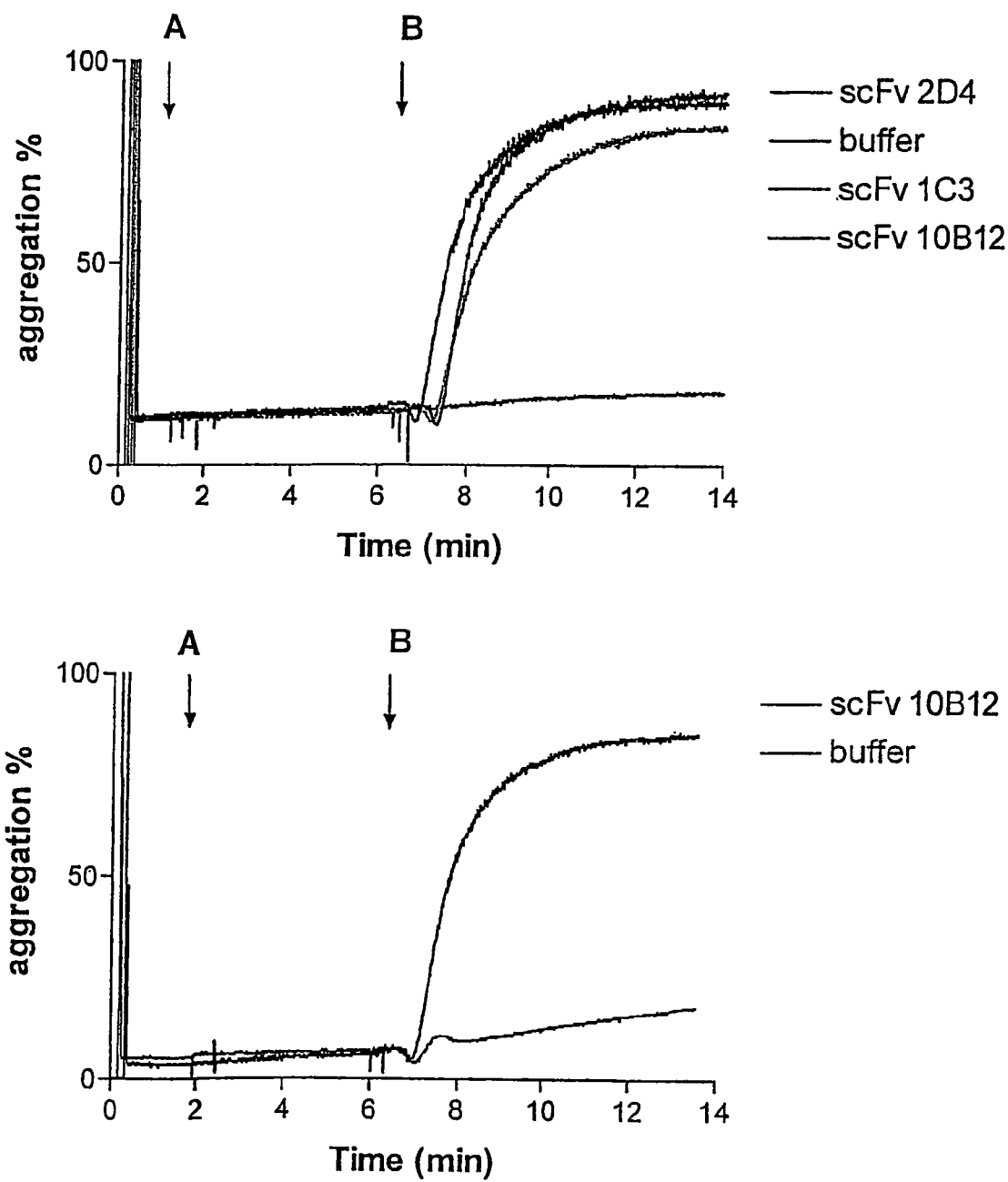
Figure 13:
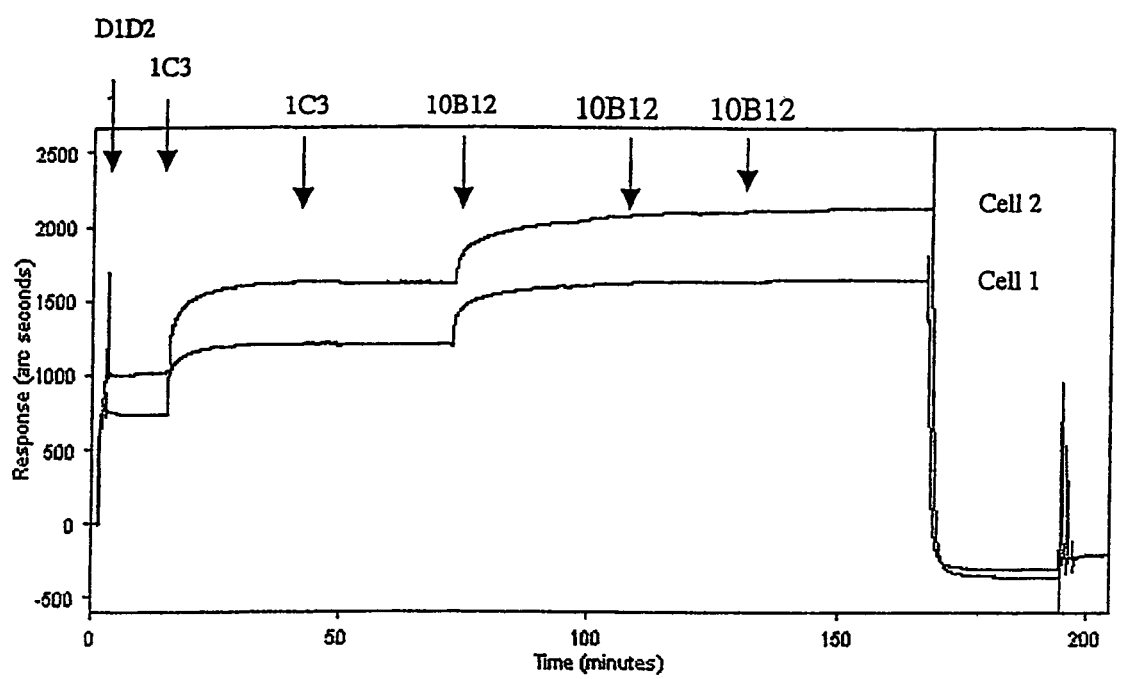

Subsequently, the effect of purified scFvs on the interaction of hD1D2-CaM with CRP was measured (FIG. 10). Once again, binding of hD1D2-CaM to CRP was specific, since no binding was observed to the control peptide GPP10. Purified scFvs were pre-incubated with hD1D2-CaM at different molar ratios (calculated using molecular weights: hD1D2-CaM, 38 kDa and scFv, 28 kDa) before addition to the peptide-coated, blocked wells. The specific binding of hD1D2-CaM to CRP was inhibited by scFv 10B12 in a dose-dependent manner, confirming the results obtained with the non-purified scFv (FIG. 9). Anti-GPVI scFv 16E12 and the negative control scFv 2F2 were both inert. Both scFv 8A1 and scFv 1C3 produced a dose dependent enhancement of binding of hD1D2 to CRP. For 1C3 this result was in contrast with the result obtained with the unpurified scFv. The enhanced binding is possibly explained by the effect of the dimeric scFvs which are present in the purified scFv preparations. Dimeric scFvs which recognise an epitope other than the collagen binding site may cross-link hD1D2, enhancing its avidity for CRP. The inventors consider the data obtained with the purified scFv 1C3 as more reliable and consistent with the results of other experiments. For instance, scFv 1C3 has little or no inhibitory effect on collagen-induced platelet aggregation (FIG. 11) and scFv 1C3 targets an epitope distinct from that recognised by scFv 10B12 (FIG. 13).

Binding of scFvs to Blood Cells
Binding to Platelets by Flow Cytometry

Figure 14:
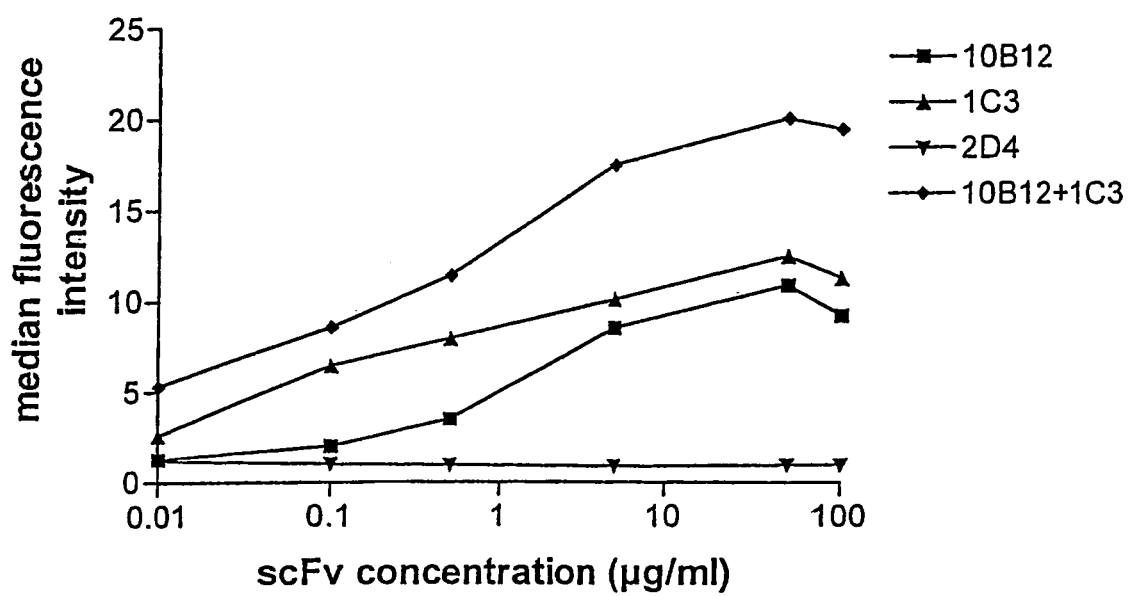

The reactivity of purified scFvs 1C3 and 10B12 with freshly isolated platelets from normal donors was assessed by flow cytometry. A dose dependent binding of the scFvs was observed. Saturation at around 50 µg/ml produced a similar maximum fluorescence intensity for both (FIG. 14). ScFv 1C3 produced plateau fluorescence at a slightly lower concentration than 10B12. This is in concordance with the slightly higher affinity (FIG. 19) of scFv 1C3. When both scFv were used simultaneously to stain platelets across the same concentration range, increased fluorescence intensities were observed, indicating that binding to platelets of scFvs 10B12 and 1C3 is non-competitive (FIG. 14). Biosensor studies confirmed that the scFvs 1C3 and 10B12 bind in a non-competitive manner to hD1D2 (FIG. 13).

Figure 15:
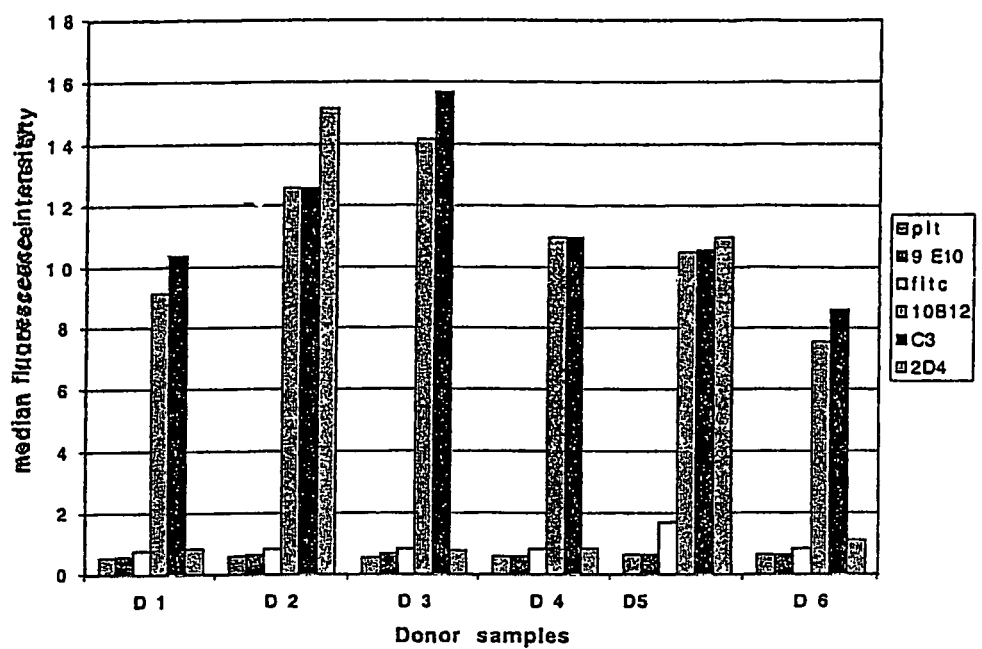

In addition, freshly isolated platelets from 4 donors were incubated with the purified scFvs 10B12 and 1C3 at 50 µg/ml concentration (FIG. 15). Platelets from two additional donors (5 and 6) were tested. These platelets were recovered from cryopreserved aliquots. Donor 5 was unique in the sense that this donor is heterozygous LV for amino acid 83 in domain 1 of hGPVI. There is a positive correlation between the fluorescence intensities produced by either scFv confirming that the same target antigen is being recognised.

Variation in Expression of GPVI on Platelets

Figure 18:
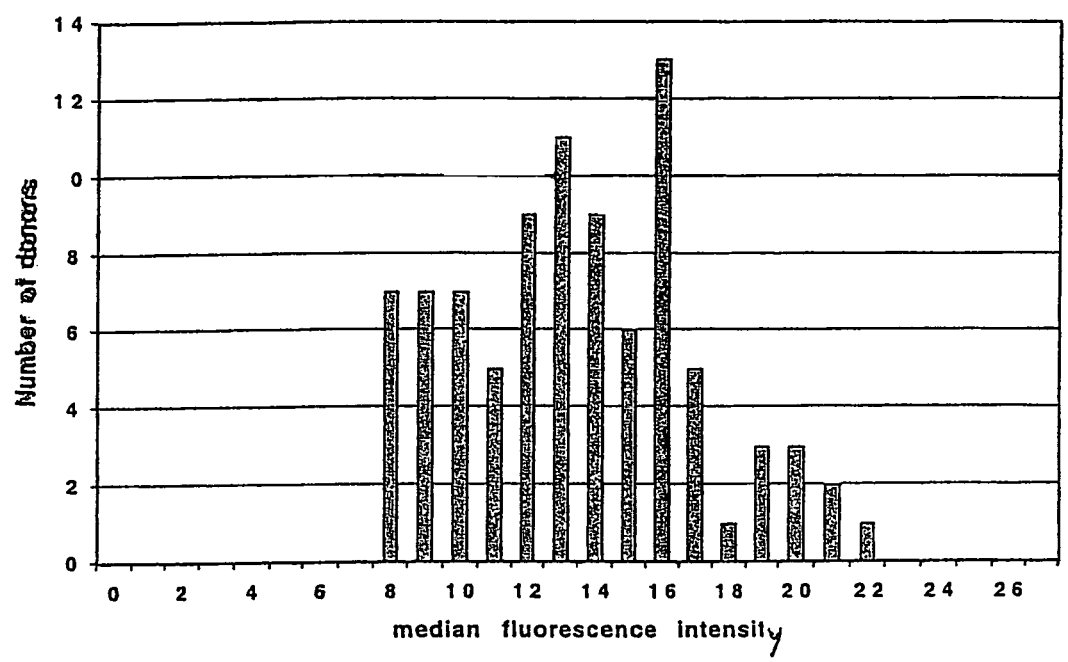

Purified scFv 1C3 at saturating level was used to study the variation in membrane expression of GPVI by flow cytometry on the platelets of 89 individuals (FIG. 18). A two-fold variation in binding of scFv 1C3 to platelets was observed. Recently, using a ligand blotting assay with labelled convulxin, Furihata and colleagues have shown a five-fold difference between donors for GPVI content, which correlated strongly with platelet procoagulant activity produced in response to convulxin (Furihata et al 2001). The relationship between surface and total expression of GPVI is unknown. One explanation why donors vary more in their total cellular content of GPVI than in surface expression level might be to preserve a consistent level of sensitivity to collagen with this activatory receptor. There appears to be a greater variation in surface expression level of GPIaIIa (up to 10-fold; Kunicki et al, 1993 and 19). High GPIaIIa expression (associated with a polymorphism in the GPIa gene: a thymidine replacing a cytosine at position 807) is a risk factor for cardiovascular disease (Santoso et al, 1999). Whether the variation in GPVI expression between individuals is of pathological significance is not yet known.

Binding to Leucocytes by Flow Cytometry

Figure 16:
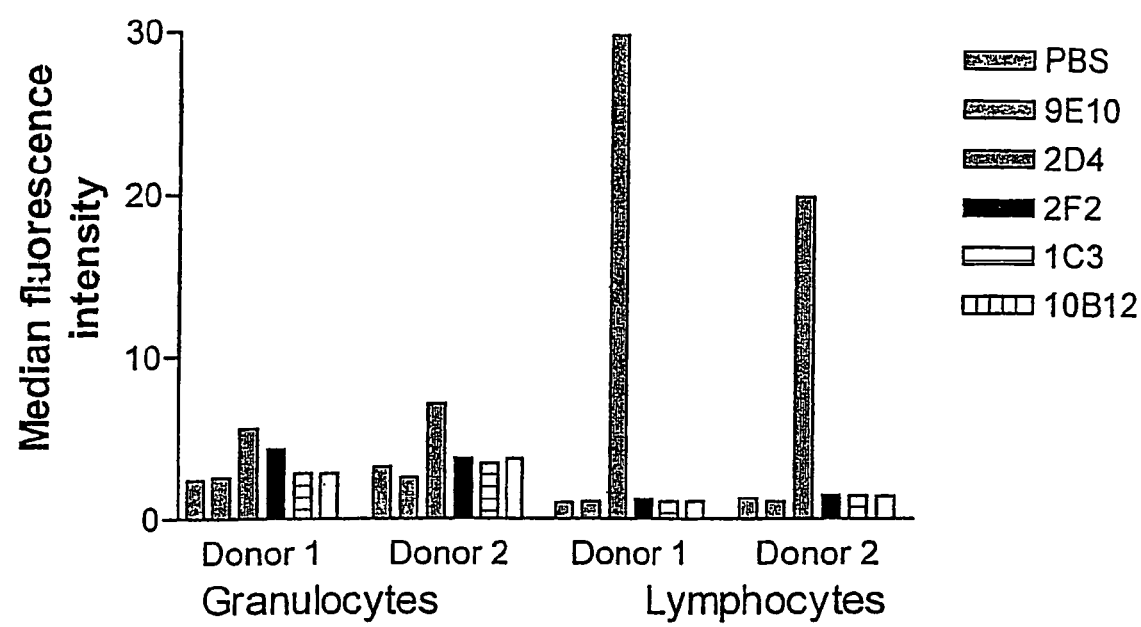

The binding of the scFvs to granulocytes and lymphocytes was studied by flow cytometry. Neither scFv 10B12 nor 1C3 showed significant binding to either of these cells (FIG. 16).

Binding to Erythrocytes by Haemagglutination Test

No agglutination of human red blood cells by the purified scFvs 10B12 and scFv 1C3 was observed (FIG. 19) using the gel card system. A control scFv FOG-1, recognising the RhD antigen (Hughes-Jones et al, 1994), did agglutinate RhD positive cells.

Figure 22:
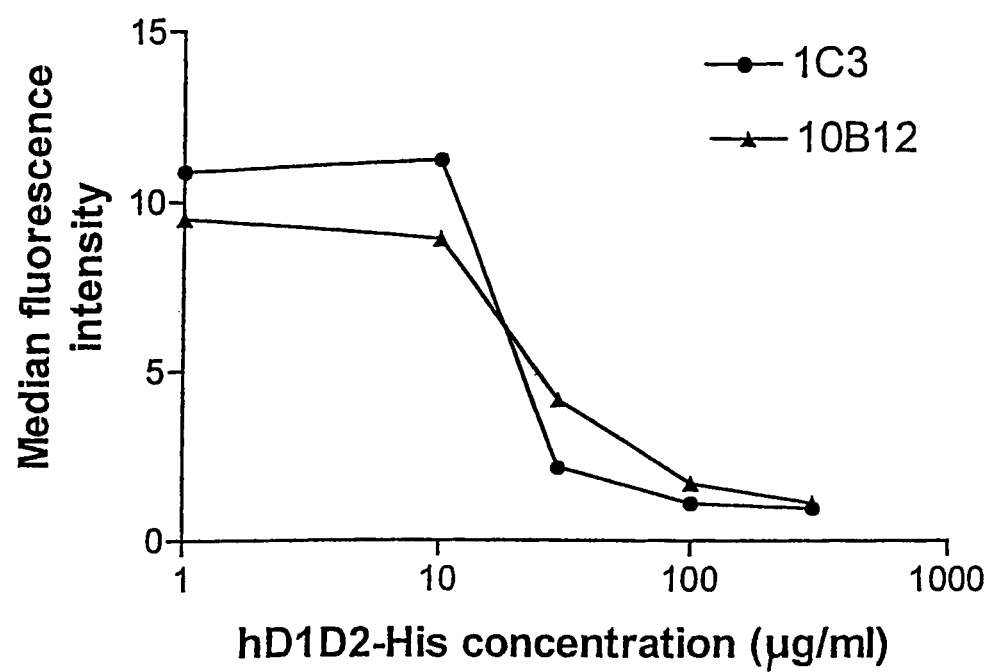

The inhibition of scFv binding to platelets by hD1D2 The binding of both scFvs 1C3 and 10B12 to platelets was inhibited by recombinant soluble hD1D2 (specifically hD1D2-His) in dose-dependent manner (FIG. 22). Binding of the control scFv 2F2, recognising GPIIbIIIa, was unaffected by the presence (at 300 µg/ml) of hD1D2.

Capacity of scFv 10B12 to Inhibit Static Platelet Adhesion to CRP and Collagen

Figure 20:
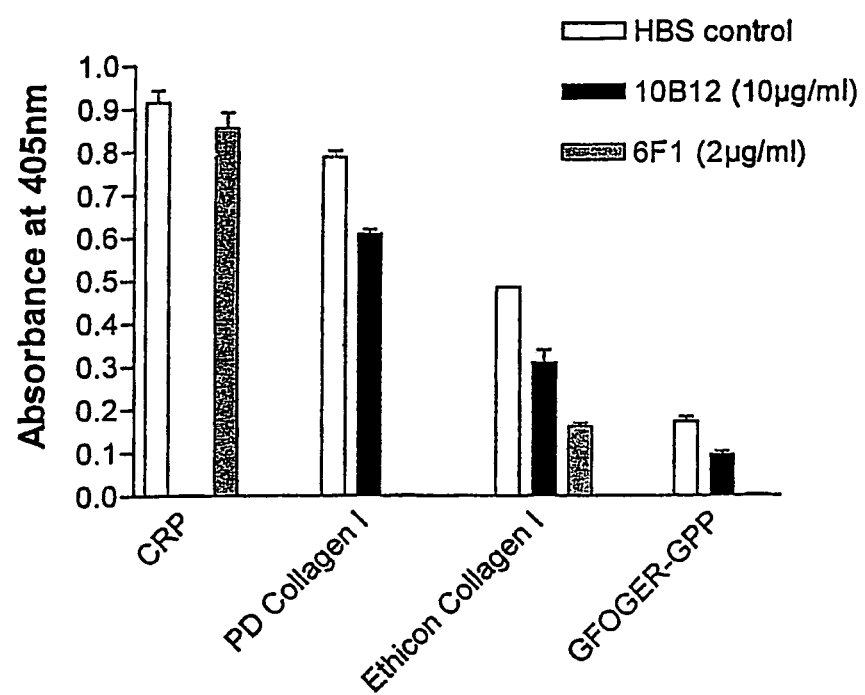
Figure 21:
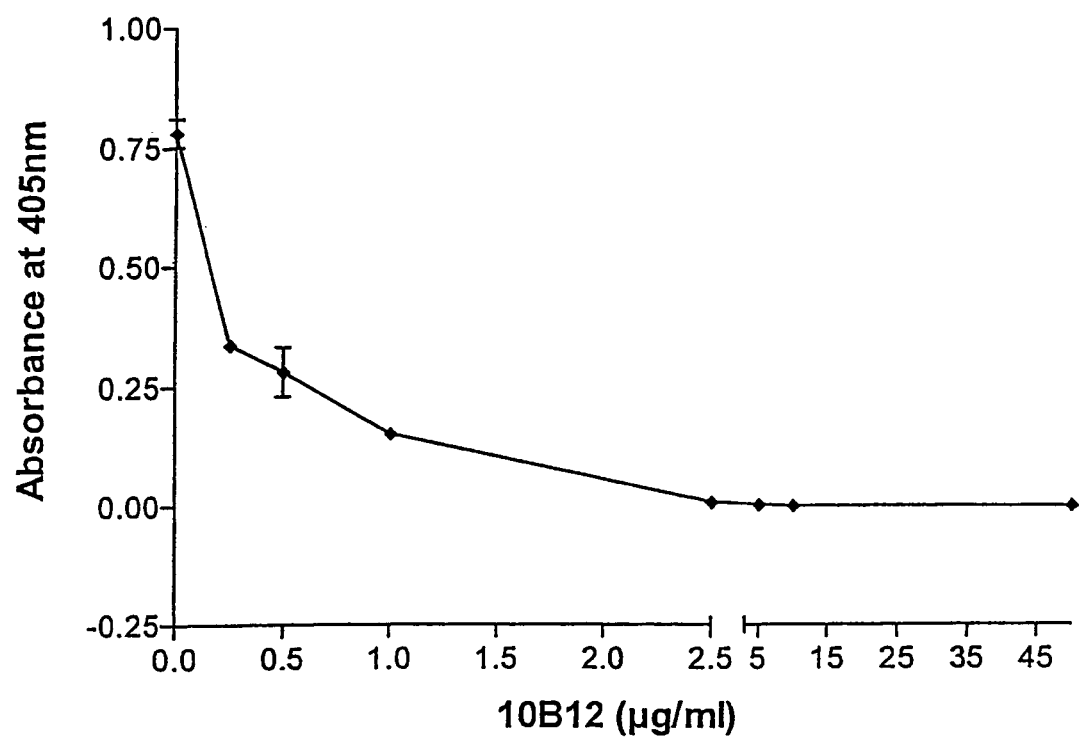

ScFv 10B12 was found to abolish platelet adhesion to CRP under static conditions, in a dose-dependent manner (FIG. 21). Attachment of platelets to CRP under static conditions was uniquely dependent on GPVI and not mediated by the adhesive collagen receptor $\alpha 2\beta 1$ (Knight et al, 1999), as confirmed by the inability of the monoclonal antibody (mAb) 6F1 against the $\alpha 2$ I domain to block this interaction (FIG. 20). Platelet adhesion to two forms of type 1 collagen and to the synthetic peptide GFOGER-GPP (Knight et al, 1998) was also measured. scFv 10B12 reduced platelet adhesion to each of these ligands also. It had been assumed that the adhesion to these ligands was only dependent on $\alpha 2\beta 1$ (since Ab 6F1 inhibits this interaction). However, the inventors now postulate that interaction of these ligands with GPVI in addition to $\alpha 2\beta 1$ may be required. The inventors suggest that the interaction with GPVI alters the activation state of $\alpha 2\beta 1$ resulting in an increased affinity for ligand.

Aggregometry

Figure 12:
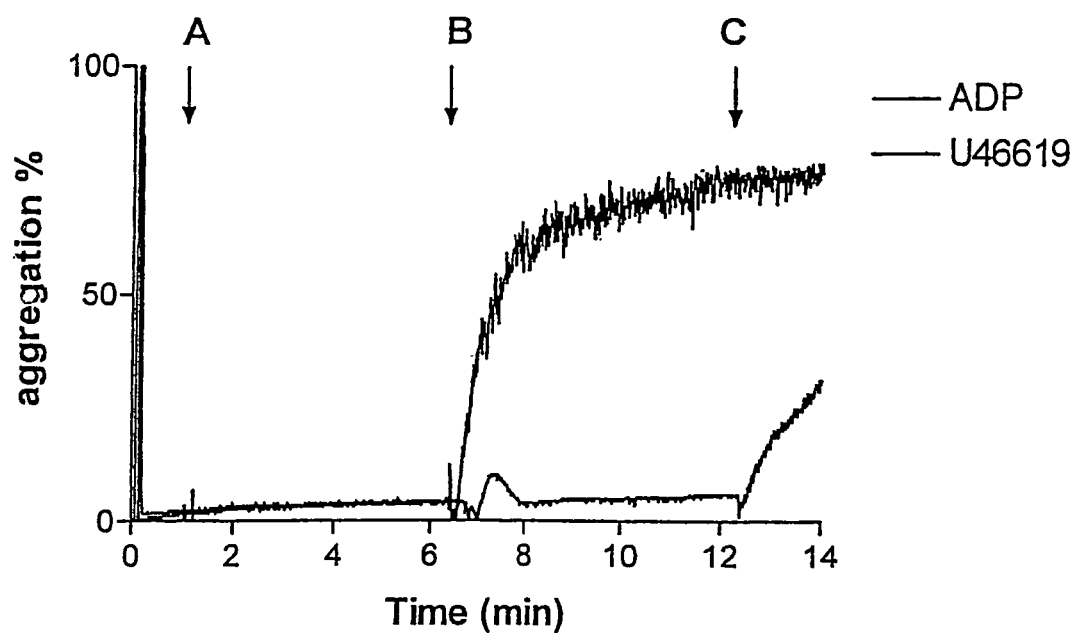
Figure 25:
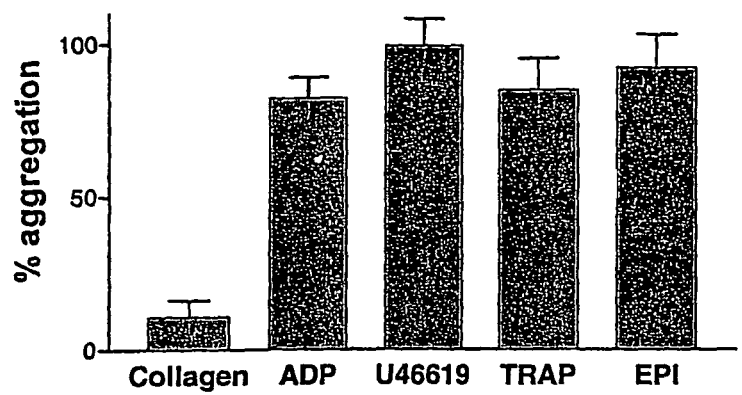

ScFv 10B12 at 50 µg/ml was found to completely inhibit platelet aggregation evoked by 1 µg/ml collagen fibres (FIG. 11a). Neither the control scFv 2D4 (anti-HLA-A2) nor scFv 1C3 produced measurable inhibition. The inhibitory capacity of scFv 10B12 was maintained at 10 µg/ml with the same agonist (FIG. 11b). However, when other agonists (ADP and U46619) were used, no inhibitory effect of scFv 10B12 was observed (FIG. 12 and FIG. 25). This confirms that scFv 10B12 is exerting a specific blockade on the collagen signalling pathway as the latter two agonists signal independently of GPVI. Taken together with the observations reported herein that scFv 10B12 binds specifically to hD1D2 and inhibits the binding of hD1D2 to CRP, the inventors conclude that scFv 10B12 is preventing collagen recognition of platelets solely by occupying part of the collagen binding site on GPVI.

Perfusion Studies

Figure 23:
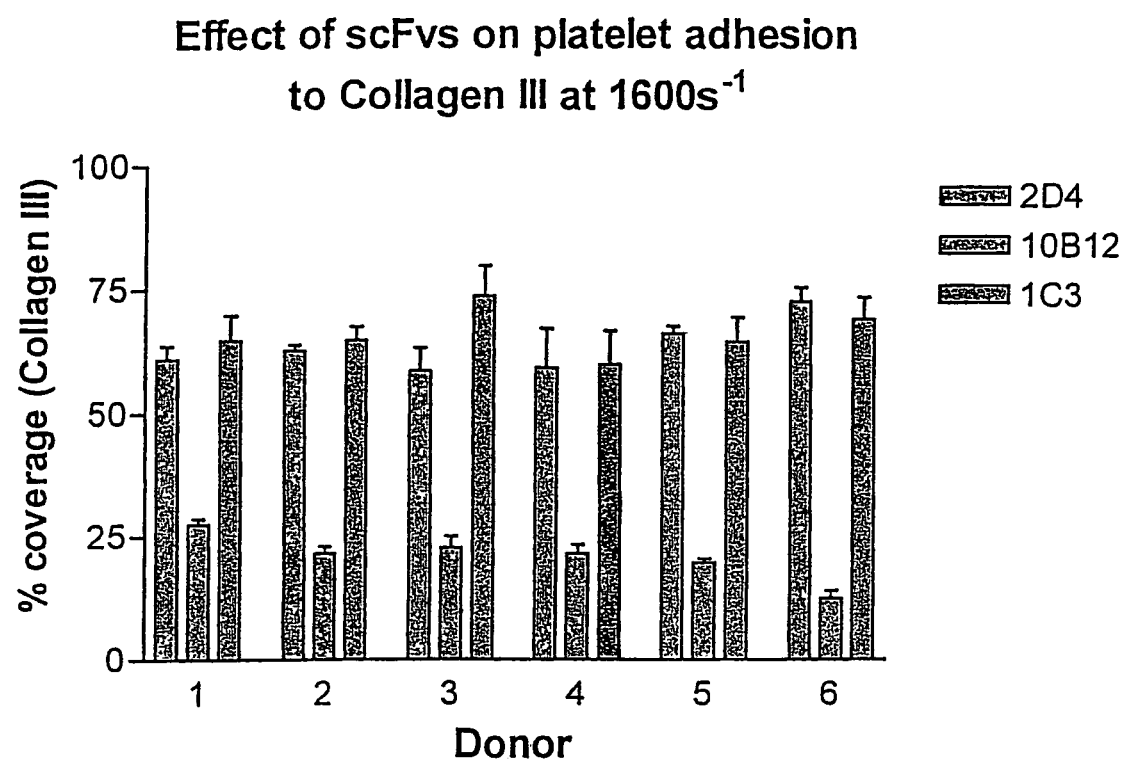

Collagen III is a potent agonist of platelet activation, which contains GPVI recognition sites (Knight et al, 1999), to which platelets will adhere under high shear rate (Saelman et al, 1994). The inventors have shown unequivocal inhibition of platelet adhesion to collagen III under flow by scFv 10B12. scFv 2D4 against HLA-A2 was completely inert and no significant difference in platelet adhesion was seen between HLA-A2 positive and negative platelets. Blood preincubated with scFv 1C3 contained platelets that were as effective in adhesion as blood treated with the negative control scFv 2D4 (FIG. 23).

Cross-Inhibition Studies Using a Resonant Mirror Biosensor

By covalently immobilising BSA-N9A to the surface of a biosensor cuvette, hD1D2-CaM could be attached by the high affinity interaction between CaM and N9A peptide, leaving hD1D2 in a favourable orientation to be recognised by scFvs. ScFvs were added sequentially to saturation, without washing. Additive binding was observed when scFv 1C3 and 10B12 were added to saturation versus a fixed amount of D1D2-CaM (FIG. 13). From the response obtained, with each scFv versus a known response of hD1D2, a 1:1 binding ratio of each scFv to D1D2-CaM is calculated (Table 1).

Figure 17:
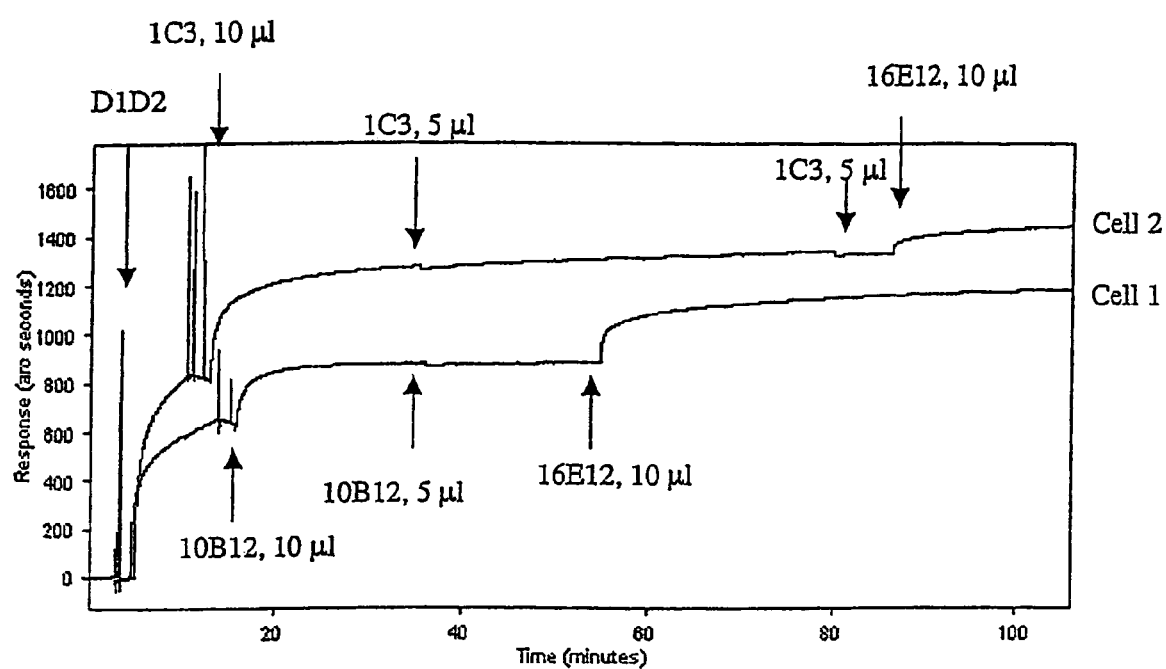

In another experiment either scFvs 1C3 or 10B12 was added to hD1D2-CaM (in separate cells), followed by scFv 16E12 (FIG. 17). Interestingly scFv 16E12 bound more readily to hD1D2-CaM pre-loaded by 10B12 than that pre-loaded with 1C3. From this the inventors conclude that 16E12 recognises an epitope which overlaps with the 1C3 epitope rather than the 10B12 epitope. This is consistent with the observation that 16E12 has no effect on the binding of hD1D2-CaM to CRP (since 10B12 is inhibitory and 1C3 is not; FIG. 10). Alternatively the observation may be explained by scFv 16E12 having a lower affinity.

The affinity of 1C3 and 10B12 was calculated from experiments conducted on scFvs purified to entirely the monomeric form by gel filtration chromatography just before the experiments. The calculated $K_D$ for purified, monomeric scFvs 10B12 and 1C3 are $7.9 \times 10^{-7}$ and $5.4 \times 10^{-7}$, respectively (FIG. 19). These are calculated as shown below.

The fastfit plot of $K_{on}$ vs scFv concentration for 1C3 (FIG. 19B) gave the following values:
Intercept=0.00111016±0.00204437
Correlation Coefficient=0.933656
Gradient=2053.14±454.739
$K_D$=Intercept/Gradient=0.00111016/2053.14=5.40713×$10^{-7}$ The fastfit plot of $K_{on}$ vs scFv concentration for 10B12 (FIG. 19D) gave the following values:
Intercept=0.00122054±0.000899749
Correlation Coefficient=0.973277
Gradient=1537.93±209.498
$K_D$=Intercept/Gradient=0.00122054/1537.93=7.93625×$10^{-7}$ DNA Sequencing of VH and VL Genes The nucleotide sequence of the VH and VL genes of the six scFvs against hD1D2 was determined. The nucleotide and translated protein sequence of the VH and VL chains of scFvs 10B12 and 1C3, and their CDR's, are presented in SEQ ID NO.s 1-20) The VH and VL genes have also been aligned to their most homologous germline genes, and replacement mutations, silent mutations and changes imprinted by the primers in the 5' end of the VH and VL genes identified. Mutation rates (number of replacements) were calculated, and are presented together with the V gene derivation in Table 2, where similar information is presented for scFvs 16E12, 8A1, 4H9 and 4D5. Amino acid annotation is according to Kabat (Kabat et al, 1991).

Clones from the CaT and the Marks library can be differentiated by two sequence characteristics. The codon AGC is used for the second serine in the linker between the VH and VL gene for CaT clones (approximately nucleotides 397-399, depending on the CDR3 length), compared to TCT for those of the Marks library, and also by the 3'-end of the VL gene. As expected 10B12 and 4D5 carried the "molecular signature" of the CaT library and the other clones 1C3, 8A1, 16E12 and 4H9 carried the ones from the Marks library.

Sequencing shows that a diverse repertoire of VH and VL genes is being used in the GPVI binders. Furthermore the level of somatic hypermutation of VH and VL genes in the majority of clones is low. This is most extreme for clone 8A1 for which the both V domains are encoded by genes in germline configuration.

The VH domains of scFvs 10B12 (the "inhibitor") and scFv 8A1 (an "enhancer") are both derived from the same VH germline gene from the VH3 gene family COS-3 (Table 2). The terms "inhibitor" and "enhancer" refer to the effects of the scFvs on hD1D2 binding to CRP (FIG. 10). In both clones the VH gene is in or in near germline configuration (8A1 and 10B12, respectively)-(Table 2). Clones 1C3 and 10B12 use both the JH3 gene.

The VH domain of clone 10B12 has some remarkable additional features. First, the two carboxy terminal VH gene encoded residues (amino acids 93 and 94) of the VH domain are not conserved. Although not unique, the K at the position 94 is generally well-conserved (Chothia et al., 1992). In 10B12 they have been changed to T and D, either as a consequence of VH and DJH gene recombination or by somatic hypermutation or by both. Secondly the CDR3 of the VH domain of scFv 10B12 has a remarkable high number of acidic residues (3 D, 1 E). The two scFvs 10B12 and 8A1 have different VL domains (L12a and DPL16, respectively). The DPL16 derived VL gene of scFv 10B12 has undergone significant somatic hypermutation with the majority of replacements in the VL-CDR1. Despite that both scFvs have COS-3 encoded VH domains they have striking differences in the their functional behaviour. This is best explained by the difference in epitope specificity of the two scFvs which will be based on the differences in the VH-CDR3 sequence and the different VL domains.

The nucleotide sequence of the VL gene of clone 1C3 showed evidence for a cross-over between the VL genes DPL5 and 2a2.272A12. Amino acids 1-23 were most likely encoded by DPL5 with only a single nucleotide mismatch. The nucleotides encoding the remaining residues of the VL domain align better to 2a2.272A12. VL domains encoded by two different VL gene segments have been reported and is best explained by cross-over resulting from the PCR amplification of the VL genes during repertoire cloning.

Sequence information has been submitted to the GenBank database under accession numbers: 10B12$V_H$, AF539528; 10B12$V_K$, AF539529; 1C3$V_H$, AF539530; 1C3$V_\lambda$, AF539531 (online October 2002).

Lysine 59 is Part of the Epitope of 10B12

In screening ELISA it was observed that 1C3, but not 10B12, binds to mD1D2. In contrast 10B12 shows some binding hD1, whilst 1C3 does not. These indicate that some critical contact residues in the 1C3 epitope are conserved between species, whereas 10B12 relies on residues which are exclusively human, some of which are on hD1.

Using the PSI-BLAST program at the National Center for Biotechnology Information (available on the internet at http:// www.ncibi.nlm.nih.gov/BLAST/ and findable using any search tool or browser using the terms "BLAST" and "NCBI"), hD1D2, mD1D2, hD1 and hD2 were submitted as separate queries versus the pdb, giving the same hits for all sequences: 1B6U, 1G0X, 1NKR, 2DL2 and 2DL1. Models were constructed from these using MODELLER software (Sali et al., 1995 *Proteins*, 23, 318-326) without subjective intervention. The same approach was used for the scFvs, with the structures 1AQK, 1MCW, 2CDO, 2MCG. Images were generated using GRASP program (Nicholls et al., 1991 *Proteins*, 11, 281-296). Surface colour was coded by electrostatic potential going from blue (potential of +13 kT/e) to red (−8 kT/e). Calculated with Poisson-Boltzmann solver within GRASP, using a uniform dielectric constant of 80 for the solvent, 2 for the protein interior, and ionic strength at zero. The probe radius used was 1.4 Å. Here, K and R have a single positive, D and E a single negative charge.

Other residues are neutral. K59 was mutated to E using the program O (Jones et al., 1991. *Acta Crystallogr* A, 47, 110-119), using the most preferred side-chain conformation from the rotomer database (Ponder and Richards, 1987 *J Mol Biol*, 193, 775-791).

Binding of both scFvs to 'the four mutant hD1D2 molecules was tested by ELISA. While the binding of 10B12 to R166S and R117P appeared quite unaffected (FIG. 24A), the binding to K59E was clearly decreased (40-63% inhibition between 2-20 μg/ml, p<0.001). Binding of 10B12 to the triple mutant was also reduced (28-50% inhibition over the same range, p<0.002). No corresponding trend was observed with 1C3 (FIG. 24B), where human to murine exchanges would not be expected to abolish the epitope. Binding of 1C3 to the triple mutant was not significantly different from hD1D2. Binding to K59E was slightly reduced (12-15% inhibition, $p<0.05$), but the largest reduction was seen with R117P (21% at 20 μg/ml, $p<0.01$).

From this data, it is concluded that lysine at position 59 in hD1 is clearly required for 10B12 binding to hD1D2 and that glutamate at this position in mD1D2 would be detrimental to 10B12 binding.

Modelling of the 10B12 Interface with hD1D2

Models of both scFvs were generated and their antigen binding sites viewed alongside the models of hD1D2 and K59E. Some observations were made for 10B12.

The highly acidic VH-CDR3 of 10B12 appears to form part of a negatively charged pocket in the antigen binding surface. This has some charge and shape complementarity with a basic multi-lobed patch on the apical surface of hD1D2, which may be at the centre of the 10B12 epitope. The basic patch on hD1 appears to be formed by K41, R46, K59 and R60, and less accessible R38. In this model, the K59E mutation seems to abolish the basic nature of the patch while the surrounding features are preserved. This would explain the reduced binding of 10B12 to K59E, relative to hD1D2. As mentioned earlier, 10B12 binds isolated hD1, but much more weakly than hD1D2, providing indication that residues outside D1 also contribute to the epitope. The binding model is compatible with this, as the footprint of the scFv would cover the interdomain hinge and extend to the apical surface of D2.

Advanced Perfusion System

Using the advanced perfusion system, platelet adhesion, activation and ensuing thrombus formation on a collagen surface was measured, in real time. Treatment of whole blood with scFv 10B12 did not significantly reduce the area covered by platelets, compared to untreated blood (FIG. 26). However, in blood treated with scFv 10B12, the adherent platelets were inhibited in two respects compared to untreated. Firstly, they showed a reduction in procoagulant expression (as measured by Annexin-V binding) dependent on the dose of scFv 10B12 (FIG. 26). Secondly, they showed a dramatic reduction in thrombus size with single platelets and small aggregates predominating and large aggregates completely absent (FIG. 27).

Thus, scFv 10B12 is antagonising. GPVI to inhibit the platelet activation process at the level of up-regulation of the fibrinogen receptor (which mediates aggregation) as well as the expression of the pro-thrombotic platelet surface (which gives rise to thrombin generation which enhances the coagulation cascade).

REFERENCES

Bellavite et al. Anal Biochem 1994;216:444-50

Bernatowicz and Matsueda Anal-Biochem. 1986; 155(1): 95-102.

Bonnerot et al. EMBO-J. 1998; 17(16): 4606-16.

de Bruin et al. Nat Biotechnol. 1999;17 (4):397-9.

Chothia et al. J Mol Biol 1992;227:799-817.

Clemetson Thromb Haemost 1995;74:111-6.

Coller Thromb Haemost 2001:86;427-443.

Cook and Tomlinson Immunol Today 1995;16:237-242.

Furihata et al. Arterioscler. Thromb. Vasc. Biol. (2001); 21: 1857-63.

Griffiths et al. EMBO J. 1994;13(14):3245-60.

Hames Chapter I: One-dimensional polyacrylamide gel electrophoresis. Gel electrophoresis of proteins. 1990; Eds Hames and Rickwood, Pub IRL Press, Oxford,. ISBN 0-19-963075-5.

Harrison Br J Haematol 2000; 111:733-44.

Hawkins et al. J. Mol. Biol. 1992; 226: 889-896.

Hughes-Jones et al. Br J Haematol 1994; 88:180-6.

Jandrot-Perrus et al. Blood 2000; 96: 1798-1807.

Kabat et al. Sequences of proteins of immunological interest. US Department of Health and Human Services, Public Health Service, National Institutes of Health. NIH Publication No. 91-3242, 5$^{th}$ edition, 1991.

Kehrel et al. Blood 1998;91:491-9.

Kunicki et al. Blood 1993;82:2693-703.

Kunicki et al. Blood 1997;89:1939-43.

Knight et al. Cardiovasc Res 1999;41:450-7

Knight et al. J Biol. Chem. 1998;273(50):33287-94.

Lapierre et al. Transfusion 1990;30(2):109-13

Marks et al. J Mol Biol 1991;222:581-97.

Moroi et al. J. Clin. Invest. 1989; 84: 1440-1445.

Montigiani et al. J Mol Biol 1996;258:6-13

Neri et al. Bio/technology (NY) 1995;13:373-7.

Nieswandt et al. J Biol Chem 2000;275(31):23998-4002

Nieswandt et al. J Exp Med 2001;193(4):459-69.

Onley et al. J Biol Chem 2000;275(32):24560-4.

Polgar et al. J Biol Chem 1997;272(21):13576-83.

Saelman et al. Blood. 1994 Mar. 1;83(5):1244-50.

Santoso et al. Blood. 1999;93(8):2449-53.

Siljander et al. Arterioscler-Thromb-Vasc-Biol. 2001; 21(4): 618-27.

Sixma et al. Throm. Res. 1998; 92(5): 43-6

Vaughan et al. Nat Biotechnol 1996;14(3):309-14.

van-der-Merwe et al. EMBO-J. 1993; 12(13): 4945-54.

Verkleij et al 1998 Blood; 91: 3808-3816.

Watson et al. Thromb. Haem. 2001; 86; 276-88.

TABLE 1

| | Minutes/ Response in Arc. Seconds⁻¹ (a.s.) | | | | | |
|---|---|---|---|---|---|---|
| | D1D2-CaM immobilised | | 1C3 scFv | | 10B12 scFv | |
| | Before | After | Before | After | Before | After |
| Cell 1 | 1.308 /−0.83 | 16.012 /733.3 | 16.012 /733.3 | 71.712 /1195.67 | 71.712 /1195.67 | 166.958 /1643.6 |
| Cell 2 | 2.010 /1.14 | 16.360 /1021.2 | 16.360 /1021.2 | 72.062 /1619.22 | 72.062 /1619.22 | 167.951 /2128.94 |

A known response of hD1D2-CaM was immobilised in each cell. Each scFv was then allowed to bind to saturation. The molar ratios of D1D2-CaM to each bound scFv are then calculated as follows: e.g. for Cell 1 the amount of D1D2-CaM immobilised is 733.3−(−0.83)=734.13 a.s.

The amount of 1C3 then bound at saturation is 1195.67−733.3=462.37 a.s.

The amount of 10B12 then bound after 1C3, also at saturation, is 1643.6−1195.67=447.93 a.s.

The ratios of 1C3: D1D2-CaM and 10B12: D1D2-CaM are 0.63 and 0.61 respectively.

This is very similar for each scFv and is close to the ratio of the calculated molecular masses (28.5 kDa for scFv and 40 kDa for D1D2-CaM) of 0.71. This confirms that binding of each scFv to hD1D2 is at a 1:1 ratio.

TABLE 2

Functional effect, V gene use, somatic mutation and VH-CDR3 length in human anti-GPVI scFvs

| ScFv clone | Cross-reactivity | CRP-rGPVI interaction | Aggregation inhibition | VH gene | No of replacements | VH-CDR3 length | VL gene | No of replacements |
|---|---|---|---|---|---|---|---|---|
| 10B12 | No* | Inhibitor | Inhibitor | COS-3/BHGH1+ | 0 | 16 | L12a/PCRdil16-5 | 8 |
| 1C3 | No* | Enhancer | Neutral | DP-73/V5-51 | 8 | 16 | 1b.366F5/DPL5 2a2.272A12/DPL11 | 5 |
| 16E12 | No** | Neutral | NT | DP-47/V3-2 | 5 | 20 | DPL16/VL3.1 | 10 |
| 8A1 | No*** | Enhancer | NT | COS-3/BHGH1+ | 0 | 12 | DPL16/VL3.1 | 0 |
| 4H9 | N.S.T. | NT | NT | DP-10/hv1051 . . . + | 0 | 14 | DPK6/Vb"+ | 10 |
| 4D5 | Yes | NT | NT | 2M27/11M27 . . . | 3 | 23 | 1b.366F5/DPL5 . . . + | 17 |

NT, not tested.
N.S.T., not sufficiently tested.
*On the basis of all assays presented herein, there is no cross-reactivity with other antigens.
**On the basis of FIGS. 1, 2 and 5, there is no cross-reactivity with other antigens.
***On the basis of FIGS. 1, 2 and 6, there is no cross-reactivity with other antigens.

```
GAGGTCCAGCTGGTACAGTCTGGGGGAGGCGTGGTCCAGCCTGGGGGGTCCCTGAGACTCTCCTG    SEQ ID NO. 1
TGCAGCGTCTGGATTCACCTTCAGTAGCTATGGCATGCACTGGGTCCGCCAGGCTCCAGGCAAGG
GGCTGGAGTGGGTGGCATTTATACGGTATGATGGAGTAATAAATACTATGCAGACTCCGTGAAG
GGCCGATTCACCATCTCCAGAGACAATTCCAAGAACACGCTGTATCTGCAAATGAACAGCCTGAG
AGCTGAGGACACGGCTGTGTATTACTGTACGGACGGATGGGCAGAGATGGCTACAACTGATGATG
CTTTTGATATTTGGGGCAGAGGGACAATGGTCACCGTC
```

```
EVQLVQSGGGVVQPGGSLRLSCAASGFTFSSYGMHWVRQAPGKGLEWVAFIRYDGSNKYYADSVK    SEQ ID NO. 2
GRFTISRDNSKNTLYLQMNSLRAEDTAVYYCTDGWAEMATTDDAFDIWGRGTMVTV
```

```
GACATCCAGATGACCCAGTCTCCTTCCACCCTGTCTGCATCTATTGGAGACAGTCACCATCAC    SEQ ID NO. 3
CTGCCGGGCCAGTGAGGGTATTTATCACTGGTTGGCCTGGTATCAGCAGAAGCCAGGGAAAGCCC
CTAAACTCCTGATCTATAAGGCCTCTAGTTTAGCCAGTGGGGCCCCATCAAGGTTCAGCGGCAGT
GGATCTGGGACAGATTTCACTCTCACCATCAGCAGCCTGCAGCCTGATGATTTTGCAACTTATTA
CTGCCAACAATATAGTAATTATCCGCTCACTTTCGGCGGAGGGACCAAGCTGGAGATCAAA
```

```
DIQMTQSPSTLSASIGDRVTITCRASEGIYHWLAWYQQKPGKAPKLLIYKASSLASGAPSRFSGS    SEQ ID NO. 4
GSGTDFTLTISSLQPDDFATYYCQQYSNYPLTFGGGTKLEIK
```

```
SYGMH                                                                SEQ ID NO. 5
```

```
FIRYDGSNKYYADSVKG                                                    SEQ ID NO. 6
```

```
GWAEMATTDDAFDI                                                       SEQ ID NO. 7
```

```
RASEGIYHWLA                                                          SEQ ID NO. 8
```

```
KASSLAS                                                              SEQ ID NO. 9
```

```
QQYSNYP                                                              SEQ ID NO. 10
```

```
CAGGTACAGCTGCAGCAGTCAGGGGCAGAGGTGAAAAAGCCCGGGGAGTCTCTGAAGATCTC      SEQ ID NO. 11
CTGTCAGGCTTCTGGATACAGCTTTTCCAGTTACTGGATCGCCTGGGTGCGCCAGATGCCCG
GGAAAGGCCTGGAGTTGATGGGGATCATCTATCCTGGTGACTCTGATGCCAGATACAGCCCG
TCCTTCCAAGGCCAGGTCACCTTCTCAGCCGACAAGTCCATAAACACCGCCTATTTGCAGTG
GAGCAGCCTGAAGGCCTCGGACACCGCCATGTATTATTGTGCAGACAAGGGAAAACTGGGA
GCTACTATTTTGGTGCTTTTGATGTCTGGGGCCAAGGGACAATGGTCACCGTCTCTTCA
```

```
QVQLQQSGAEVKKPGESLKISCQASGYSFSSYWIAWVRQMPGKGLELMGIIYPGDSDARYSP      SEQ ID NO. 12
SFQGQVTFSADKSINTAYLQWSSLKASDTAMYYCARQGKTGSYYFGAFDVWGQGTMVTVSS
```

| | |
|---|---|
| CAGTCTGTGTTGACGCAGCCGCCCTCAATGTCTGCGGCCCCAGGACAGAAGGTCACCATCTC<br>CTGCACTGGAACCAGCAGTGACGTTGGTGGTTATAACTATGTCTCCTGGTACCAACAGCACC<br>CAGGCAAAGCCCCCAAACTCATGCTTTTTGAGGTCAGTCATCGGCCCTCAGGGGTTTCTAAT<br>CGCTTCTCTGGCTCCAAGTCTGACAACACGGCCTCCCTGACCATCTCTGGGCTCCAGGCTGA<br>GGACGAGGCTGATTATTACTGCAGTTCATATACAGGCAGCAGCACTTGGGTGTTCGGCGGAG<br>GGACCAAGGTCACCGTCCTA | SEQ ID NO. 13 |
| QSVLTQPPSMSAAPGQKVTISCTGTSSDVGGYNYVSWYQQHPGKAPKLMLFEVSHRPSGVSN<br>RFSGSKSDNTASLTISGLQAEDEADYYCSSYTGSSTWVFGGGTKVTVL | SEQ ID NO. 14 |
| SYWIA | SEQ ID NO. 15 |
| IIYPGDSDARYSPSFQG | SEQ ID NO. 16 |
| QGKTGSYYFGAFDV | SEQ ID NO. 17 |
| TGTSSDVGGYNYVS | SEQ ID NO. 18 |
| EVSHRPS | SEQ ID NO. 19 |
| SSYTGSSTWV | SEQ ID NO. 20 |
| CRP (GCO(GPO)₁₀GCOG | SEQ ID NO. 21 |
| GPP10 (GCP(GPP)₁₀GCPG | SEQ ID NO. 22 |
| CAG GAA ACA GCT ATG AC | SEQ ID NO. 23 |
| GAA TTT TCT GTA TGA GG | SEQ ID NO. 24 |
| CTA TGC GGC CCC ATT CA | SEQ ID NO. 25 |

The invention claimed is:

1. A specific binding member that specifically binds human GPVI and which comprises a specific binding member that comprises (i) an antibody VH domain having the amino acid sequence of SEQ ID NO: 2; and (ii) an antibody VL domain comprising CDRs 1-3 and intervening framework regions.

2. A specific binding member that specifically binds human GPVI and which comprises a specific binding member that comprises (i) an antibody VL domain having the amino acid sequence of SEQ ID NO: 4; and (ii) an antibody VH domain comprising CDRs 1-3 and intervening framework regions.

3. A specific binding member that specifically binds human GPVI and which comprises a specific binding member that comprises (i) an antibody VH domain having the amino acid sequence of SEQ ID NO: 2; and (ii) an antibody VL domain comprising CDRs 1-3 and intervening framework regions, wherein the specific binding member binds GPVI with affinity equal to or better than the affinity of an GPVI antigen-binding site formed by the 10B12 VH domain (SEQ ID NO. 2) and the 10B12 VL domain (SEQ ID NO. 4), the affinity of the specific binding member and the affinity of the antigen-binding site being as determined under the same conditions.

4. A specific binding member that specifically binds human GPVI and which comprises a specific binding member that comprises (i) an antibody VH domain having the amino acid sequence of SEQ ID NO: 2; and (ii) an antibody VL domain comprising CDRs 1-3 and intervening framework regions, wherein the specific binding member inhibits collagen-induced platelet aggregation and/or the adhesion of platelets to Collagen-Related-Peptide (CRP).

5. The specific binding member according to claim 3 that inhibits collagen-induced platelet aggregation and/or the adhesion of platelets to Collagen-Related Peptide (CRP).

6. A specific binding member that specifically binds human GPVI and which comprises a specific binding member that comprises (i) an antibody VH domain having the amino acid sequence of SEQ ID NO. 2; and (ii) an antibody VL domain comprising CDRs 1-3 and intervening framework regions, wherein said binding member inhibits collagen-induced platelet aggregation under conditions of flow wherein whole blood is perfused over a collagen-coated surface, such that platelets within the blood have a shear rate of 1600 s$^{-1}$, and/or the adhesion of platelets to collagen under Collagen-Related peptide (CRP) under static conditions, with a potency equal to or better than the potency of a GPVI antigen-binding site formed by the 10B12 VH domain (SEQ ID NO. 2) and the 10B12 VL domain (SEQ ID NO. 4), the potency of the specific binding member and the potency of the antigen-binding site being as determined under the same conditions.

7. A specific binding member that specifically binds human GPVI and which comprises a specific binding member that comprises (i) an antibody VH domain having the amino acid sequence of SEQ ID NO. 2; and (ii) an antibody VL domain having the amino acid sequence of SEQ ID NO. 4, wherein said binding member inhibits collagen-induced platelet aggregation under conditions of flow wherein whole blood is perfused over a collagen-coated surface, such that platelets within the blood have a shear rate of 1600 s$^{-1}$, and/or the adhesion of platelets to collagen under Collagen-Related peptide (CRP) under static conditions, with a potency equal to or better than the potency of a GPVI antigen-binding site formed by the 10B12 VH domain (SEQ ID NO. 2) and the 10B12 VL domain (SEQ ID NO. 4), the potency of the specific binding member and the potency of the antigen-binding site being as determined under the same conditions.

8. A specific binding member that specifically binds human GPVI and which comprises a specific binding member that comprises (i) an antibody VH domain having the amino acid sequence of SEQ ID NO. 2; and (ii) an antibody VL domain comprising CDRs 1-3 and intervening framework regions, wherein the specific binding member comprises at least one of an scFv antibody molecule and an antibody constant region.

9. A specific binding member that specifically binds human GPVI and which comprises a specific binding member that comprises (i) an antibody VL domain having the amino acid sequence of SEQ ID NO. 4; and (ii) an antibody VH domain comprising CDRs 1-3 and intervening framework regions, wherein the specific binding member comprises at least one of an scFv antibody molecule and an antibody constant region.

10. A specific binding member that specifically binds human GPVI and which comprises a specific binding member that comprises (i) an antibody VL domain having the amino acid sequence of SEQ ID NO. 4; and (ii) an antibody VH domain comprising CDRs 1-3 and intervening framework regions, wherein the specific binding member binds GPVI with affinity equal to or better than the affinity of a GPVI antigen-binding site formed by the 10B12 VH domain (SEQ ID NO. 2) and the 10B12 VL domain (SEQ ID NO. 4), the affinity of the specific binding member and the affinity of the antigen-binding site being as determined under the same conditions.

11. A specific binding member that specifically binds human GPVI and which comprises a specific binding member that comprises (i) an antibody VL domain having the amino acid sequence of SEQ ID NO. 4; and (ii) an antibody VH domain comprising CDRs 1-3 and intervening framework regions, wherein the specific binding member inhibits collagen-induced platelet aggregation and/or the adhesion of platelets to Collagen-Related-Peptide (CRP).

12. A specific binding member that specifically binds human GPVI and which comprises a specific binding member that comprises (i) an antibody VL domain having the amino acid sequence of SEQ ID NO. 4; and (ii) an antibody VH domain comprising CDRs 1-3 and intervening framework regions, wherein said binding member inhibits collagen-induced platelet aggregation under conditions of flow wherein whole blood is perfused over a collagen-coated surface, such that platelets within the blood have a shear rate of 1600 s$^{-1}$, and/or the adhesion of platelets to collagen under Collagen-Related peptide (CRP) under static conditions, with a potency equal to or better than the potency of a GPVI antigen-binding site formed by the 10B12 VH domain (SEQ ID NO. 2) and the 10B12 VL domain (SEQ ID NO. 4), the potency of the specific binding member and the potency of the antigen-binding site being as determined under the same conditions.

13. A specific binding member that specifically binds human GPVI and which comprises: a specific binding member that comprises:
(i) an antibody VH domain that is selected from (a) the antibody 10B12 VH domain having the amino acid sequence of SEQ ID NO. 2, which includes 10B12 VH CDRs 1-3, and (b) an antibody VH domain comprising a VH CDR3 having the amino acid sequence of SEQ ID NO. 7 and a VH CDR1 having the amino acid sequence of SEQ ID NO. 5, and a VH CDR2 having the amino acid sequence of SEQ ID NO. 6, wherein the CDRs are together with intervening framework regions, and
(ii) an antibody VL domain that is selected from (a) the antibody 10B12 VL domain having the amino acid sequence of SEQ ID NO. 4, which includes 10B12 VL CDRs 1-3, and (b) an antibody VL domain comprising a VL CDR1 having the amino acid sequence of SEQ ID NO. 8, and a VL CDR2 having the amino acid sequence of SEQ ID NO. 9, and a VL CDR3 having the amino acid sequence of SEQ ID NO. 10, wherein the CDRs are together with intervening framework regions.

* * * * *

UNITED STATES PATENT AND TRADEMARK OFFICE
CERTIFICATE OF CORRECTION

| | | |
|---|---|---|
| PATENT NO. | : 8,853,368 B2 | |
| APPLICATION NO. | : 10/499266 | |
| DATED | : October 7, 2014 | |
| INVENTOR(S) | : Peter Alexander Smethurst et al. | |

It is certified that error appears in the above-identified patent and that said Letters Patent is hereby corrected as shown below:

On the title page item (56), col. 2, line 26, delete:
"Nieswandt, Bernard et al., "Expression and Function of the Mouse Collagen Receptor Glycoprotein VI is Strictly Dependent on Its Association with the FcRγ Chain," *J. Biol. Chem.* 275 (31):23998-24002, Aug. 4, 2000." should read, --Nieswandt, Bernard et al., "Expression and Function of the Mouse Collagen Receptor Glycoprotein VI Is Strictly Dependent on Its Association with the FcRγ Chain," *J. Biol. Chem.* 275 (31):23998-24002, Aug. 4, 2000.--.

On page 2, col. 1, line 62, under item (56) Other Publications delete:
"Hu et al., "Minibody: A Novel Engineered Anti-Carcinoembryonic Antigen Antibody Fragment (Single-Chain FV-$C_H3$) Which Exhibits Rapid, High-Level Targeting of Xenografts," *Cancer Research* 56:3055-3061, Jul. 1, 1996." should read, --Hu et al., "Minibody: A Novel Engineered Anti-Carcinoembryonic Antigen Antibody Fragment (Single-Chain Fv-$C_H3$) Which Exhibits Rapid, High-Level Targeting of Xenografts," *Cancer Research* 56:3055-3061, Jul. 1, 1996.--.

On page 3, col. 1, line 1, under item (56) Other Publications delete:
"Polgár et al., "Platelet Activation and Signal Transduction by Convulxin, a C-type Lectin from *Crotalus durissus* terrificus (Tropical Rattlesnake) Venom via the p62/GPVI Collagen Receptor," *The Journal of Biological Chemistry* 272(21):13576-13583, May 23, 1997." should read, --Polgár et al., "Platelet Activation and Signal Transduction by Convulxin, a C-type Lectin from *Crotalus durissus terrificus* (Tropical Rattlesnake) Venom via the p62/GPVI Collagen Receptor," *The Journal of Biological Chemistry* 272(21):13576-13583, May 23, 1997.--.

On page 3, col. 1, line 21, under item (56) Other Publications delete:
"Šali et al., "Evaluation of Comparative Protein Modeling by Modeller," *Proteins: Structure, Function, and Genetics* 23:318-326, 1995." should read, --Šali et al., "Evaluation of Comparative Protein Modeling by MODELLER," *Proteins: Structure, Function, and Genetics* 23:318-326, 1995.--.

Signed and Sealed this
Twenty-first Day of April, 2015

Michelle K. Lee
*Director of the United States Patent and Trademark Office*

CERTIFICATE OF CORRECTION (continued)
U.S. Pat. No. 8,853,368 B2

In the claims,

Column 54, Line 45:
"of SEQ ID NO. 5, and a VH CDR2having the amino acid" should read, --of SEQ ID NO. 5, and a VH CDR2 having the amino acid--.

Column 54, Line 54:
"of SEQ ID NO. 9, and a VL CDR3having the amino acid" should read, --of SEQ ID NO. 9, and a VL CDR3 having the amino acid--.